United States Patent
Duncan et al.

(10) Patent No.: US 11,555,053 B2
(45) Date of Patent: *Jan. 17, 2023

(54) CRYSTALLINE SALT FORMS

(71) Applicant: Stealth BioTherapeutics Inc., Needham, MA (US)

(72) Inventors: Scott M. Duncan, Bedford, MA (US); Martin P. Redmon, Boston, MA (US)

(73) Assignee: Stealth BioTherapeutics Inc., Needham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/866,164

(22) Filed: May 4, 2020

(65) Prior Publication Data

US 2021/0047368 A1 Feb. 18, 2021

Related U.S. Application Data

(63) Continuation of application No. 16/084,168, filed as application No. PCT/US2017/021790 on Mar. 10, 2017, now Pat. No. 10,683,326.

(60) Provisional application No. 62/307,095, filed on Mar. 11, 2016.

(51) Int. Cl.
 *C07K 5/09* (2006.01)
 *A61K 38/00* (2006.01)

(52) U.S. Cl.
 CPC ............ *C07K 5/0817* (2013.01); *A61K 38/00* (2013.01); *C07B 2200/13* (2013.01)

(58) Field of Classification Search
 CPC .......... A61K 38/00; A61P 27/02; A61P 43/00; C07B 2200/13; C07K 5/0817; C07K 5/1019
 See application file for complete search history.

(56) References Cited

U.S. PATENT DOCUMENTS

| | | | |
|---|---|---|---|
| 5,312,899 A | 5/1994 | Schiller | |
| 9,549,963 B2 | 1/2017 | Liu et al. | |
| 9,982,014 B2 | 5/2018 | Hirai et al. | |
| 10,676,506 B2 | 6/2020 | Duncan | |
| 10,683,326 B2 | 6/2020 | Duncan et al. | |
| 10,975,118 B2* | 4/2021 | Duncan | C07K 5/1019 |
| 11,034,724 B2 | 6/2021 | Duncan | |
| 11,261,213 B2 | 3/2022 | Duncan | |
| 2011/0177047 A1 | 7/2011 | Liu et al. | |
| 2012/0178762 A1 | 7/2012 | Redman-Furey et al. | |
| 2012/0329730 A1 | 12/2012 | Szeto et al. | |
| 2013/0059784 A1 | 3/2013 | Wilson | |
| 2014/0044689 A1 | 2/2014 | Liu et al. | |
| 2015/0359838 A1 | 12/2015 | Szeto et al. | |
| 2016/0264623 A1 | 9/2016 | Hirai et al. | |
| 2018/0044378 A1 | 2/2018 | Duncan et al. | |
| 2019/0202861 A1 | 7/2019 | Duncan et al. | |
| 2019/0233474 A1 | 8/2019 | Duncan | |
| 2019/0382442 A1 | 12/2019 | Duncan et al. | |
| 2020/0283476 A1* | 9/2020 | Duncan | C07K 5/06086 |
| 2020/0369724 A1* | 11/2020 | Duncan | C07K 5/1019 |
| 2021/0047368 A1 | 2/2021 | Duncan et al. | |
| 2021/0061853 A1 | 3/2021 | Duncan | |
| 2021/0292362 A1 | 9/2021 | Duncan | |

FOREIGN PATENT DOCUMENTS

| | | |
|---|---|---|
| CN | 102428086 A | 4/2012 |
| CN | 103003283 A | 3/2013 |
| CN | 104244964 A | 12/2014 |
| WO | WO-2010/125004 A1 | 11/2010 |
| WO | WO-2011/156473 A1 | 12/2011 |
| WO | WO-2013/126597 A1 | 8/2013 |
| WO | WO-2015/084649 A1 | 6/2015 |
| WO | WO-2016/001042 A1 | 1/2016 |
| WO | WO-2016/007921 A1 | 1/2016 |

OTHER PUBLICATIONS

International Search Report and Written Opinion for International Application No. PCT/US17/21790 dated Jun. 5, 2017.
Dai et al., "Mitochondrial Targeted Antioxidant Peptide Ameliorates Hypertensive Cardiomyopathy," J Am Coll Cardiol, 58(1): 73-82 (2011).
Sabbah et al., "Chronic Therapy with Elamipretide (MTP-131), a Novel Mitochondria-Targeting Peptide, Improves Left Ventricular and Mitochondrial Function in Dogs with Advanced Heart Failure," Circ Heart Fail, 9(2): 1-10 (2016).
Sabbah et al., "Long-term therapy with Bendavia (MTP-131), a novel mitochondria-targeting peptide, normalizes functional mitochondrial abnormalities in left ventricular myocardium of dogs with heart failure," Mitochondrion, 13(6): 912 (2013).
Yang et al., "Role of mitochondria in the pathogenesis and treatment of glaucoma," National Medical Journal of China (English), 22: 4358-4365 (2013).
Carpino et al., "Rapid, continuous solution phase synthesis: application to peptides of pharmaceutical interest," Organic Process Research and Development, 7: 28-37 (2003).
Dolca et al., "Mictochondrial targeting with antioxidant peptide ss-31 prevents mitochondrial depolarization, reduces islet cell apoptosis, increases islet cell yield, and improves posttransplantation function," Journal of the American Society of Nephrology, 18:213-222 (2007).
Peng et al., "Site-specific chemical modifications of recombinant proteins produced in mammalian cells by using the genetically encoded aldehyde tag," Proceedings of the National Academy of Sciences of the United States of America, 106(9): 3000-3005 (2009).

* cited by examiner

*Primary Examiner* — Marcela M Cordero Garcia

(74) *Attorney, Agent, or Firm* — Dana M. Gordon; Foley Hoag LLP

(57) ABSTRACT

Disclosed are various crystalline salt forms of D-Arg-Dmt-Lys-Phe-NH$_2$.

8 Claims, 36 Drawing Sheets

CRYSTALLINE SALT FORMS

RELATED APPLICATIONS

This application is a continuation of U.S. patent application Ser. No. 16/084,168, filed Jan. 11, 2019; which is the U.S. 371 national phase of International Patent Application No. PCT/US2017/021790, filed Mar. 10, 2017; which claims the benefit of priority to U.S. Provisional Patent Application Ser. No. 62/307,095, filed Mar. 11, 2016.

BACKGROUND

Through oxidative phosphorylation, mitochondria convert nutrients and oxygen into adenosine triphosphate (ATP), the chemical transporter of energy in most aerobic organisms. The electron transport chain (ETC) of the mitochondria represents the primary source of ATP, as well as a source of reactive oxygen species (ROS). Mitochondrial dysfunction results in less ATP production and, as a result, insufficient energy to maintain the cell. Such dysfunction also results in excessive ROS production, spiraling cellular injury, and ultimately apoptosis of the cell. Mitochondrial dysfunction, is a key element believed to be at the root of a variety of serious, debilitating diseases.

Natural antioxidants such as coenzyme Q and vitamin E have been shown to provide some protection of the cell from damage induced by elevated ROS levels associated with mitochondrial dysfunction. However, antioxidants or oxygen scavengers have also been shown to reduce ROS to unhealthy levels and may not reach the ETC in sufficient concentrations to correct the mitochondrial imbalance. Therefore, there is a need for novel compounds that can selectively target the ETC, restore efficient oxidative phosphorylation, and, thereby, address mitochondrial disease and dysfunction.

DETAILED DESCRIPTION

Figure 1:
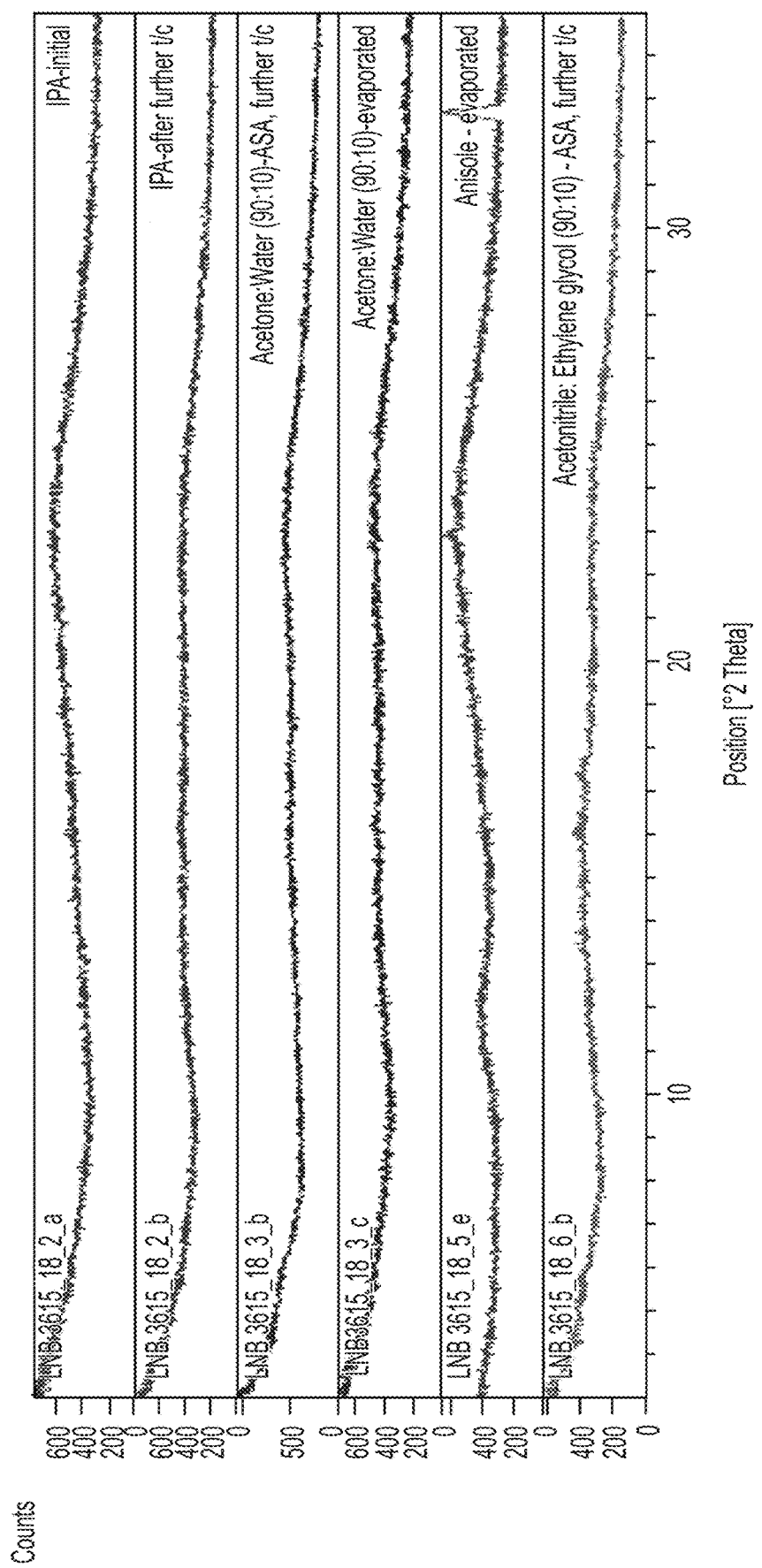
FIG. 1 depicts a XRPD pattern of a hydrochloride salt of Compound I.

The present invention features salts of Compound I

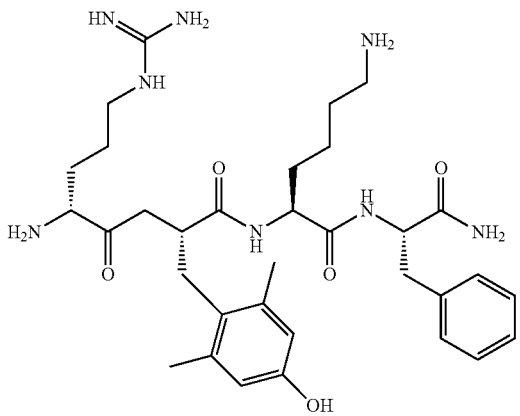 [SMILES: Cc1cc(O)cc(C)c1C[C@H](CC(=O)[C@H](N)CCCNC(=N)N)C(=O)N[C@@H](CCCCN)C(=O)N[C@@H](Cc1ccccc1)C(N)=O]

(I; MTP-131; D-Arg-Dmt-Lys-Phe-NH$_2$). Compound 1 has been shown to affect the mitochondrial disease process by helping to protect organs from oxidative damage caused by excess ROS production and to restore normal ATP production.

A crystalline form of a salt of Compound I can be used to modulate/improve the physicochemical properties of the compound, including but not limited to solid state properties (e.g., crystallinity, hygroscopicity, melting point, or hydration), pharmaceutical properties (e.g., solubility/dissolution rate, stability, or compatibility), as well as crystallization characteristics (e.g., purity, yield, or morphology).

In certain embodiments, the present invention provides a pharmaceutical preparation comprising a crystalline salt of Compound (I) and one or more pharmaceutically acceptable excipients. In certain embodiments, the pharmaceutical preparations may be for use in treating or preventing a condition or disease as described herein.

In certain embodiments, the polymorph of the crystalline salt is characterized by powder X-ray diffraction (XRPD). θ represents the diffraction angle, measured in degrees. In certain embodiments, the diffractometer used in XRPD measures the diffraction angle as two times the diffraction angle θ. Thus, in certain embodiments, the diffraction patterns described herein refer to X-ray intensity measured against angle 2θ.

In certain embodiments, a crystalline salt of Compound (I) is not solvated (e.g., the crystal lattice does not comprise molecules of a solvent). In certain alternative embodiments, a crystalline salt of Compound (I) is solvated. In some cases, the solvent is water.

In one aspect, the invention features a crystalline form of Compound I which has characteristic peaks in the powder X-ray diffraction (XRPD) pattern as shown in any one of FIGS. 1-26.

In another aspect, the invention features a crystalline form of Compound I which has characteristic peaks in the powder X-ray diffraction (XRPD) pattern at values of two theta (° 2θ) as shown in any one of Tables 1-20.

The relative intensity, as well as the two theta value, of each peak in Tables 1-20, as well as FIGS. 1-26, may change or shift under certain conditions, although the crystalline form is the same. One of ordinary skill in the art should be able to readily determine whether a given crystalline form is the same crystalline form as described in one of Tables 1-20, as well as FIGS. 1-26 by comparing their XRPD data.

In another aspect, the invention features a crystalline form of Compound I which has characteristic peaks in the powder X-ray diffraction (XRPD) pattern at values of two theta (° 2θ) as shown in any one of Tables 11-18.

In another aspect, the invention features a crystalline form of Compound I which has characteristic peaks in the powder X-ray diffraction (XRPD) pattern at values of two theta (° 2θ) as shown in any one of Tables 5, 6, 9 and 10.

In another aspect, the invention features a crystalline form of Compound I which has characteristic peaks in the powder X-ray diffraction (XRPD) pattern at values of two theta (° 2θ) as shown in any one of Tables 1-2, 3-4, 7-8, 19 and 20.

Figure 3:
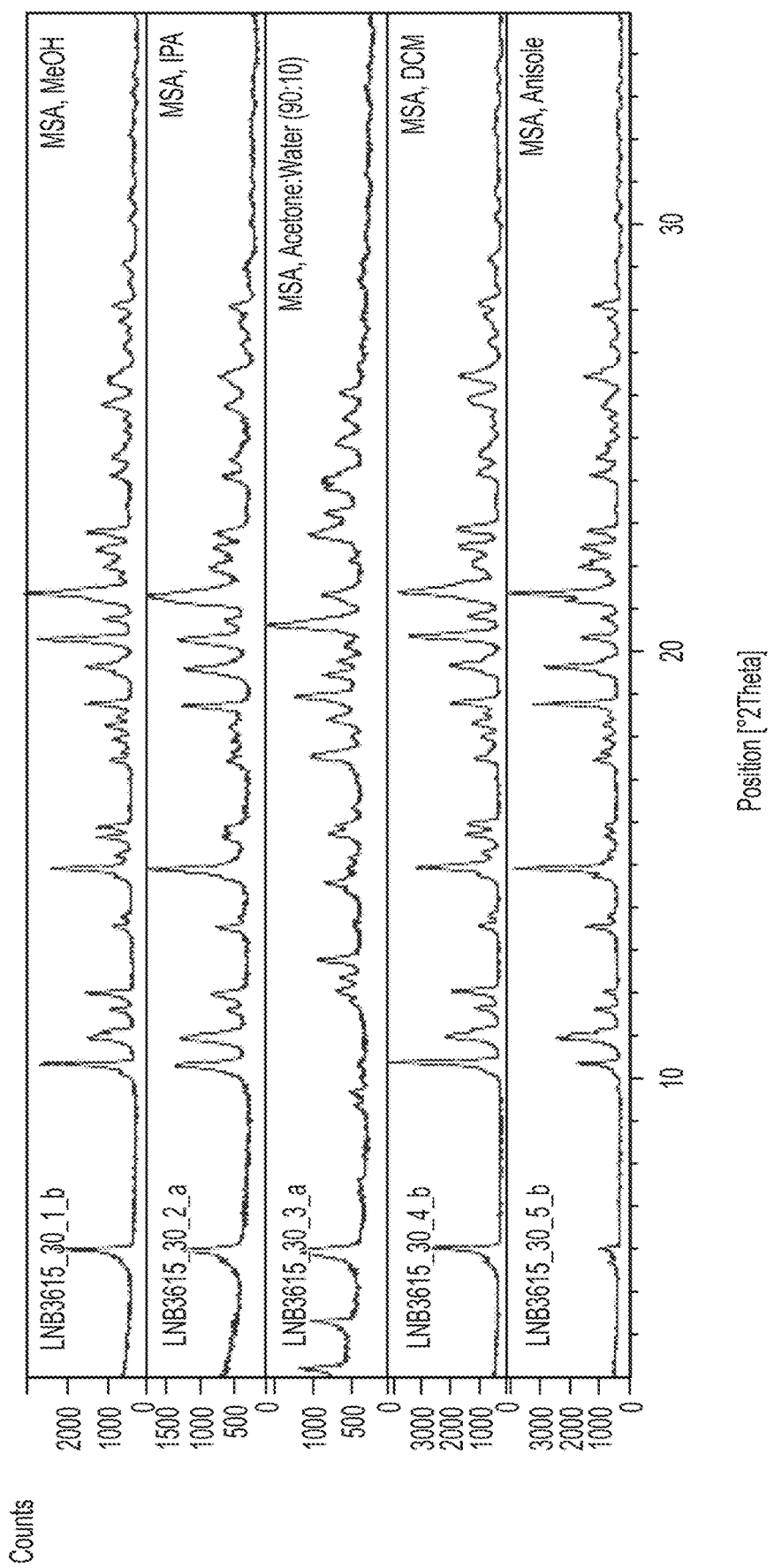
FIG. 3 depicts a XRPD pattern of a mesylate salt of Compound I.

In yet another aspect, the invention features a crystalline form of a mesylate salt of Compound I which has characteristic peaks in the powder X-ray diffraction (XRPD) pattern as shown in FIG. 3.

In another aspect, the invention features a crystalline form of a mesylate salt Compound I which has characteristic peaks in the powder X-ray diffraction (XRPD) pattern at values of two theta (° 2θ) of 6.0, 10.4, 11.0, 12.0, 14.9, 19.3, 20.4, and 21.4.

In another aspect, the invention features a crystalline form of a mesylate salt of Compound I which has characteristic peaks in the powder X-ray diffraction (XRPD) pattern at values of two theta (° 2θ) of 6.0, 10.4, 11.0, 12.0, 14.9, 15.7, 18.8, 19.3, 20.4, 20.8, 21.2, 21.4, 21.6, 22.0, 22.5, 22.9, 25.9, and 26.4.

Figure 11:
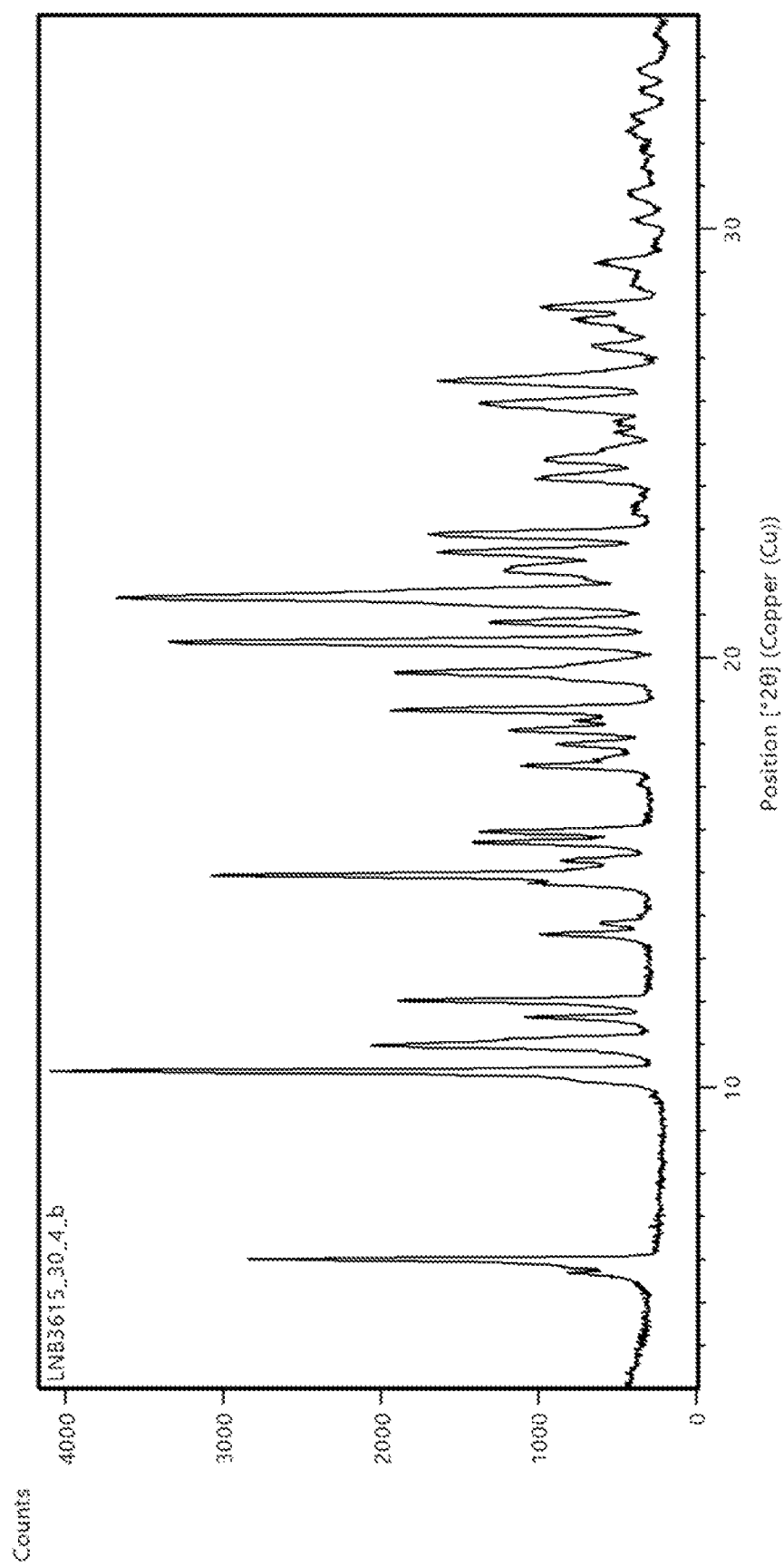
FIG. 11 depicts a XRPD pattern of a mesylate salt of Compound I Pattern 1 (Dichloromethane).

In yet another aspect, the invention features a crystalline form of a mesylate salt of Compound I which has characteristic peaks in the powder X-ray diffraction (XRPD) pattern as shown in FIG. 11.

In yet another aspect, the invention features a crystalline form of a mesylate salt of Compound I which has characteristic peaks in the powder X-ray diffraction (XRPD) pattern at values of two theta (° 2θ) as shown in Table 5.

In another aspect, the invention features a crystalline form of a mesylate salt of Compound I which has characteristic peaks in the powder X-ray diffraction (XRPD) pattern at values of two theta (° 2θ) of 3.2, 4.3, 6.0, 12.8, 17.5, 18.9, 20.6, 21.4, and 22.7.

In another aspect, the invention features a crystalline form of a mesylate salt of Compound I which has characteristic peaks in the powder X-ray diffraction (XRPD) pattern at values of two theta (° 2θ) of 3.2, 4.3, 6.0, 12.0, 12.4, 12.8, 14.6, 15.8, 15.9, 17.5, 18.4, 18.9, 19.4, 19.8, 20.1, 20.6, 21.4, 22.7, 23.2, 23.8, 24.8, 25.4, and 26.1.

Figure 12:
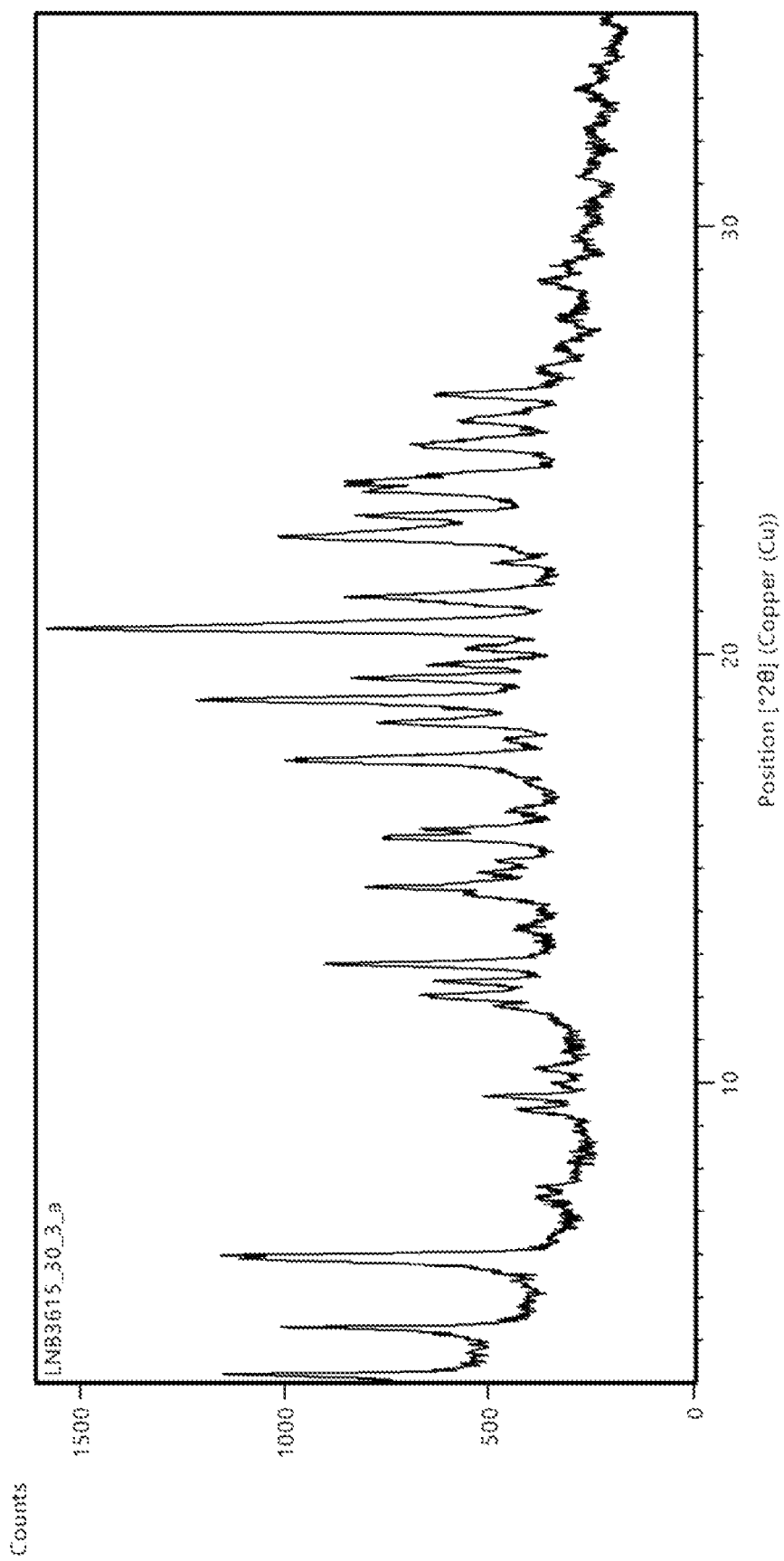
FIG. 12 depicts a XRPD pattern of a mesylate salt of Compound I Pattern 2 (Acetone:water (90:10 v/v)).

In yet another aspect, the invention features a crystalline form of a mesylate salt of Compound I which has characteristic peaks in the powder X-ray diffraction (XRPD) pattern as shown in FIG. 12.

In yet another aspect, the invention features a crystalline form of a mesylate salt of Compound I which has characteristic peaks in the powder X-ray diffraction (XRPD) pattern at values of two theta (° 2θ) as shown in Table 6.

Figure 5:
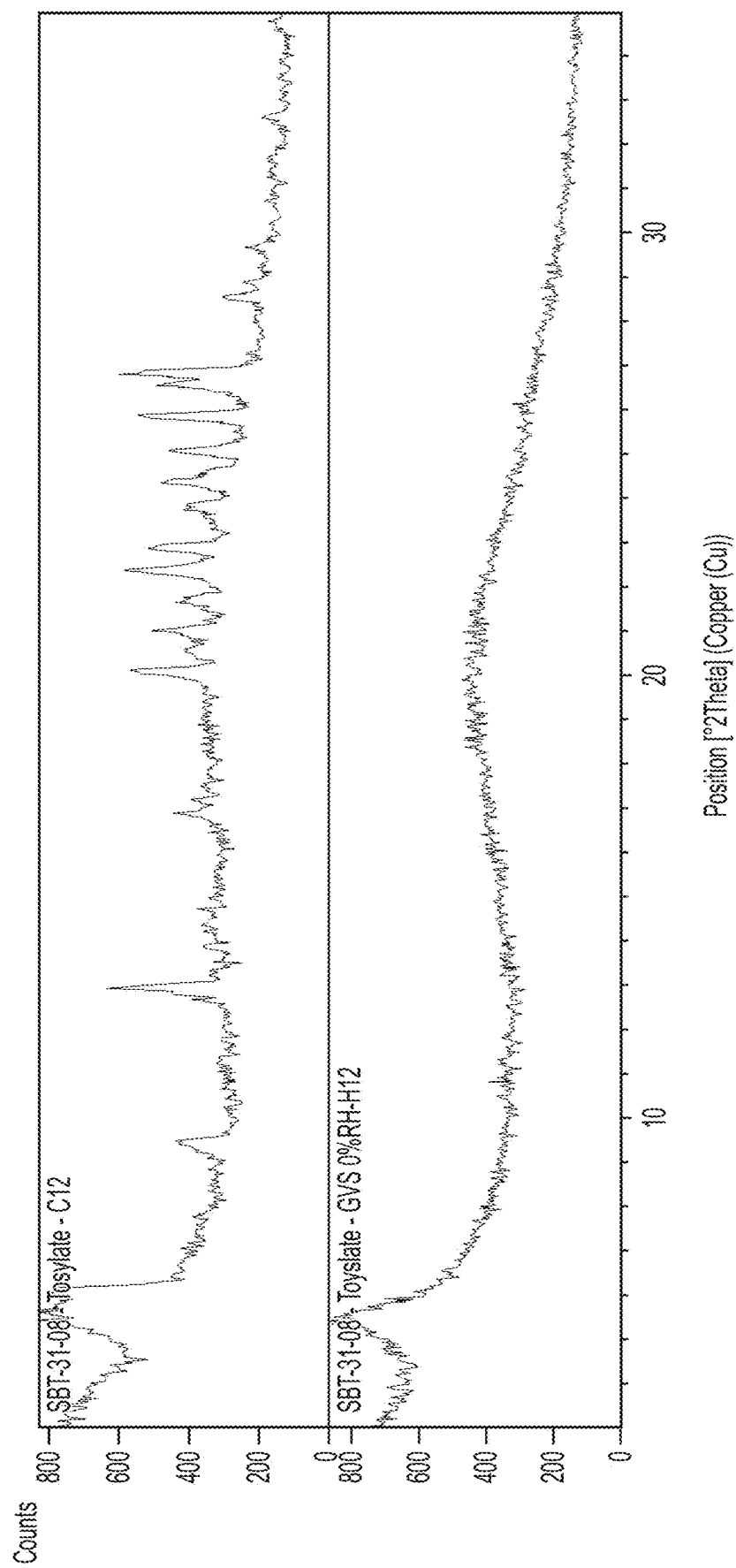
FIG. 5 depicts a XRPD pattern of a tosylate salt of Compound I.

In yet another aspect, the invention features a crystalline form of a mesylate salt of Compound I which has characteristic peaks in the powder X-ray diffraction (XRPD) pattern as shown in FIG. 5.

In another aspect, the invention features a crystalline form of a tosylate salt of Compound I which has characteristic peaks in the powder X-ray diffraction (XRPD) pattern at values of two theta (° 2θ) of 11.6, 12.2, 13.4, 15.4, 17.0, 20.2, 22.4, 22.7, and 23.1.

In another aspect, the invention features a crystalline form of a tosylate salt of Compound I which has characteristic peaks in the powder X-ray diffraction (XRPD) pattern at values of two theta (° 2θ) of 6.3, 11.6, 12.2, 13.4, 14.7, 15.4, 16.1, 17.0, 18.9, 20.2, 22.4, 22.7, and 23.1.

Figure 9:
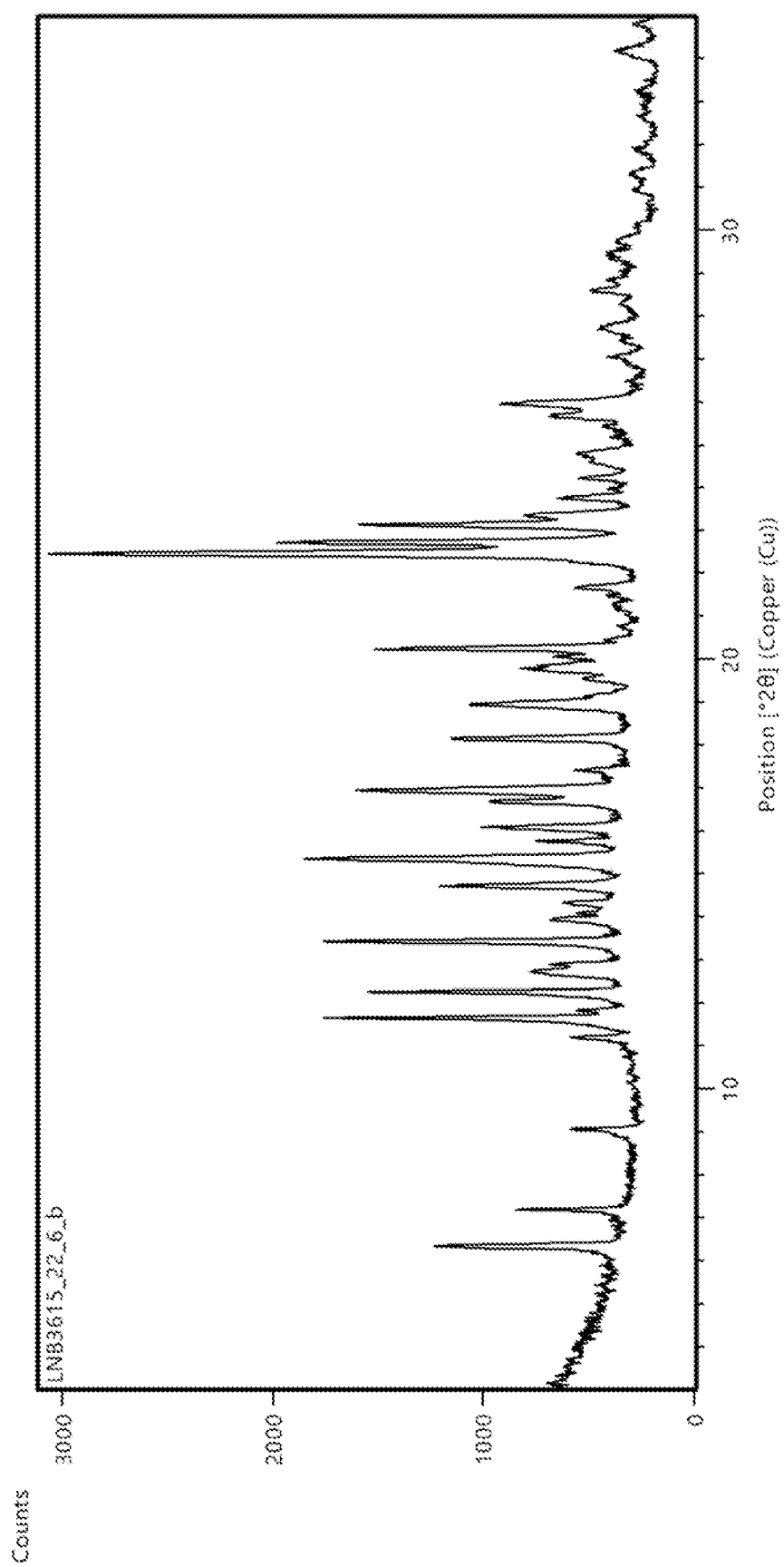
FIG. 9 depicts a XRPD pattern of a tosylate salt of Compound I Pattern 1 (Acetonitrile:ethyleneglycol (90:10 v/v)).

In yet another aspect, the invention features a crystalline form of a tosylate salt of Compound I which has characteristic peaks in the powder X-ray diffraction (XRPD) pattern as shown in FIG. 9.

In yet another aspect, the invention features a crystalline form of a tosylate salt of Compound I which has characteristic peaks in the powder X-ray diffraction (XRPD) pattern at values of two theta (° 2θ) as shown in Table 3.

In another aspect, the invention features a crystalline form of a tosylate salt of Compound I which has characteristic peaks in the powder X-ray diffraction (XRPD) pattern at values of two theta (° 2θ) of 6.5, 12.0, 13.0, 13.3, 15.7, 17.3, 19.4, 20.5, and 23.1.

In another aspect, the invention features a crystalline form of a tosylate salt of Compound I which has characteristic peaks in the powder X-ray diffraction (XRPD) pattern at values of two theta (° 2θ) of 6.5, 11.6, 11.8, 12.0, 13.0, 13.3, 15.0, 15.7, 15.9, 17.3, 19.4, 19.6, 20.5, 22.4, 22.8, 23.1, and 23.7.

Figure 10:
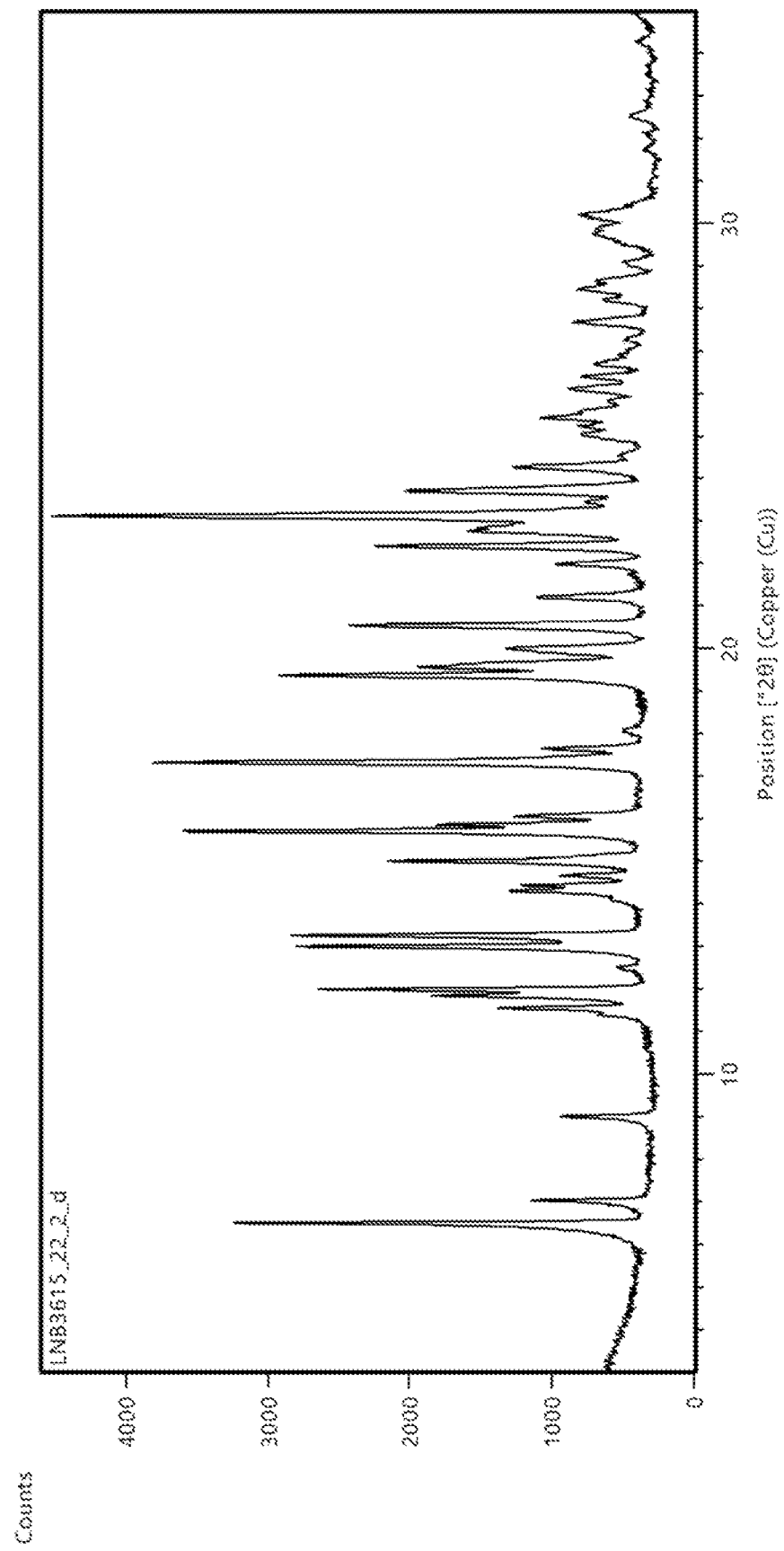
FIG. 10 depicts a XRPD pattern of a tosylate salt of Compound I Pattern 2 (2-propanol).

In yet another aspect, the invention features a crystalline form of a tosylate salt of Compound I which has characteristic peaks in the powder X-ray diffraction (XRPD) pattern as shown in FIG. 10.

In yet another aspect, the invention features a crystalline form of a tosylate salt of Compound I which has characteristic peaks in the powder X-ray diffraction (XRPD) pattern at values of two theta (° 2θ) as shown in Table 4.

Figure 6:
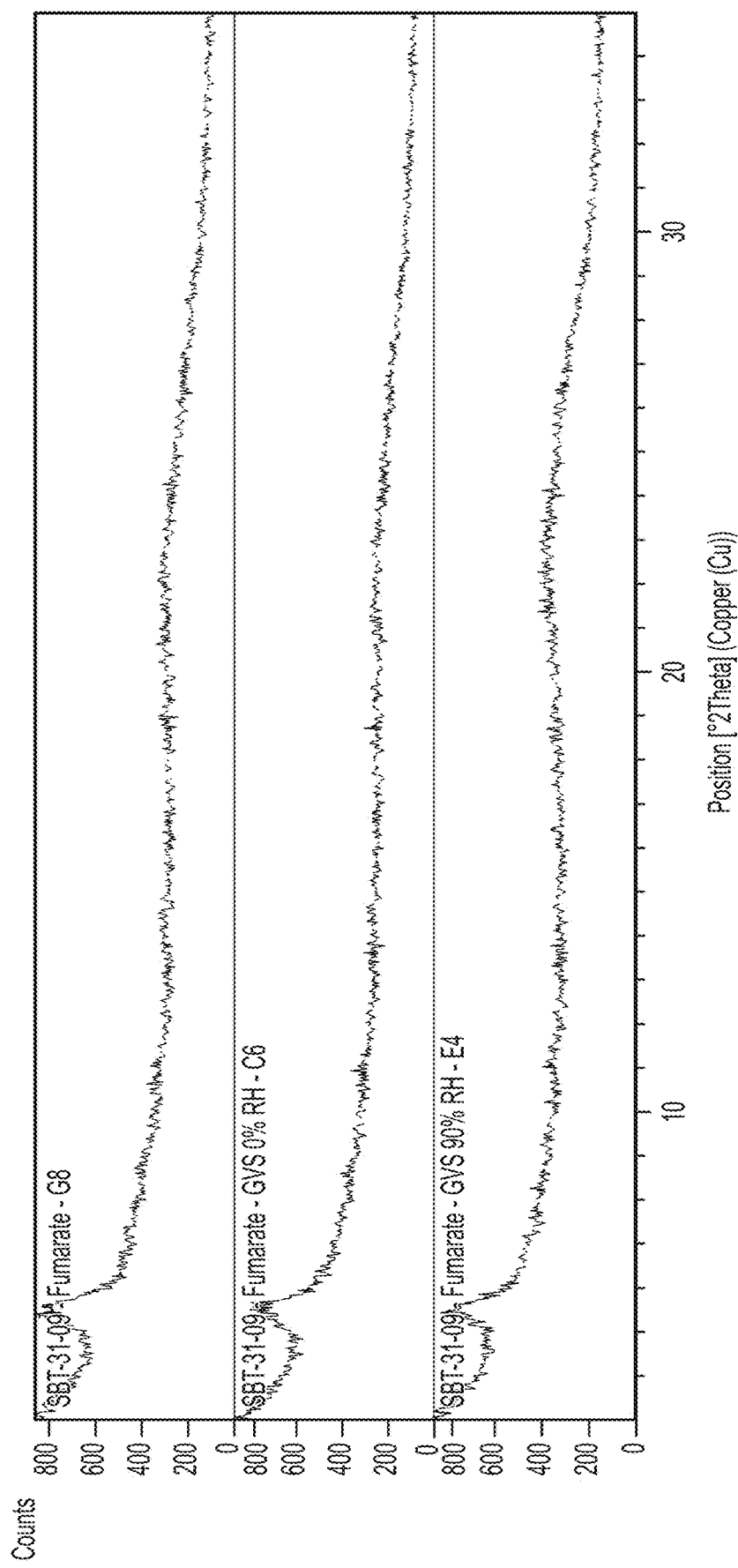
FIG. 6 depicts a XRPD pattern of a fumarate salt of Compound I.

In yet another aspect, the invention features a crystalline form of a fumarate salt of Compound I which has characteristic peaks in the powder X-ray diffraction (XRPD) pattern as shown in FIG. 6.

In another aspect, the invention features a crystalline form of a fumarate salt of Compound I which has characteristic peaks in the powder X-ray diffraction (XRPD) pattern at values of two theta (° 2θ) of 3.6, 12.0, 16.0, 21.2, 23.0, 23.3, 24.7, 24.9, and 25.7.

In another aspect, the invention features a crystalline form of a fumarate salt of Compound I which has characteristic peaks in the powder X-ray diffraction (XRPD) pattern at values of two theta (° 2θ) of 3.6, 7.2, 11.1, 12.0, 13.2, 16.0, 17.9, 18.3, 19.0, 19.4, 21.2, 23.0, 23.3, 24.7, 24.9, 25.7, 26.1, and 28.6.

Figure 17:
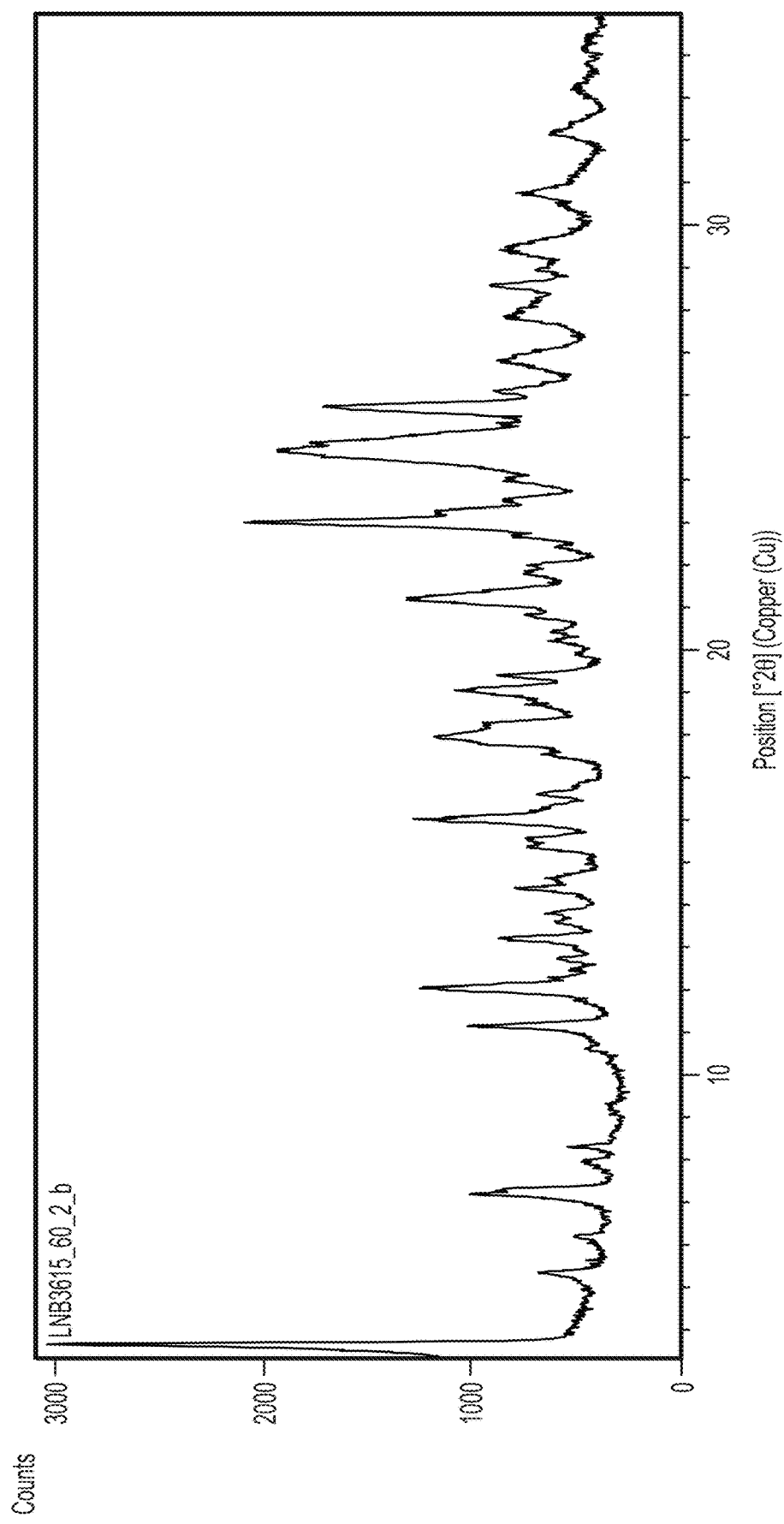
FIG. 17 depicts experimental a XRPD pattern of a fumarate salt of Compound I Pattern 1 (2-propanol).

In yet another aspect, the invention features a crystalline form of a fumarate salt of Compound I which has characteristic peaks in the powder X-ray diffraction (XRPD) pattern as shown in FIG. 17.

In yet another aspect, the invention features a crystalline form of a fumarate salt of Compound I which has characteristic peaks in the powder X-ray diffraction (XRPD) pattern at values of two theta (° 2θ) as shown in Table 11.

In another aspect, the invention features a crystalline form of a fumarate salt of Compound I which has characteristic peaks in the powder X-ray diffraction (XRPD) pattern at values of two theta (° 2θ) of 4.2, 11.3, 11.7, 12.4, 14.8, 17.0, 17.2, 20.7, 22.6, 23.3, 23.6, 24.1, 24.5, and 25.0.

In another aspect, the invention features a crystalline form of a fumarate salt of Compound I which has characteristic peaks in the powder X-ray diffraction (XRPD) pattern at values of two theta (° 2θ) of 4.2, 5.3, 10.3, 11.3, 11.7, 12.0, 12.4, 12.7, 13.0, 13.3, 14.8, 15.5, 15.8, 16.1, 17.0, 17.2, 18.1, 20.7, 21.2, 22.0, 22.3, 22.6, 23.3, 23.6, 24.1, 24.5, 25.0, 25.6, 26.0, and 28.6.

Figure 18:
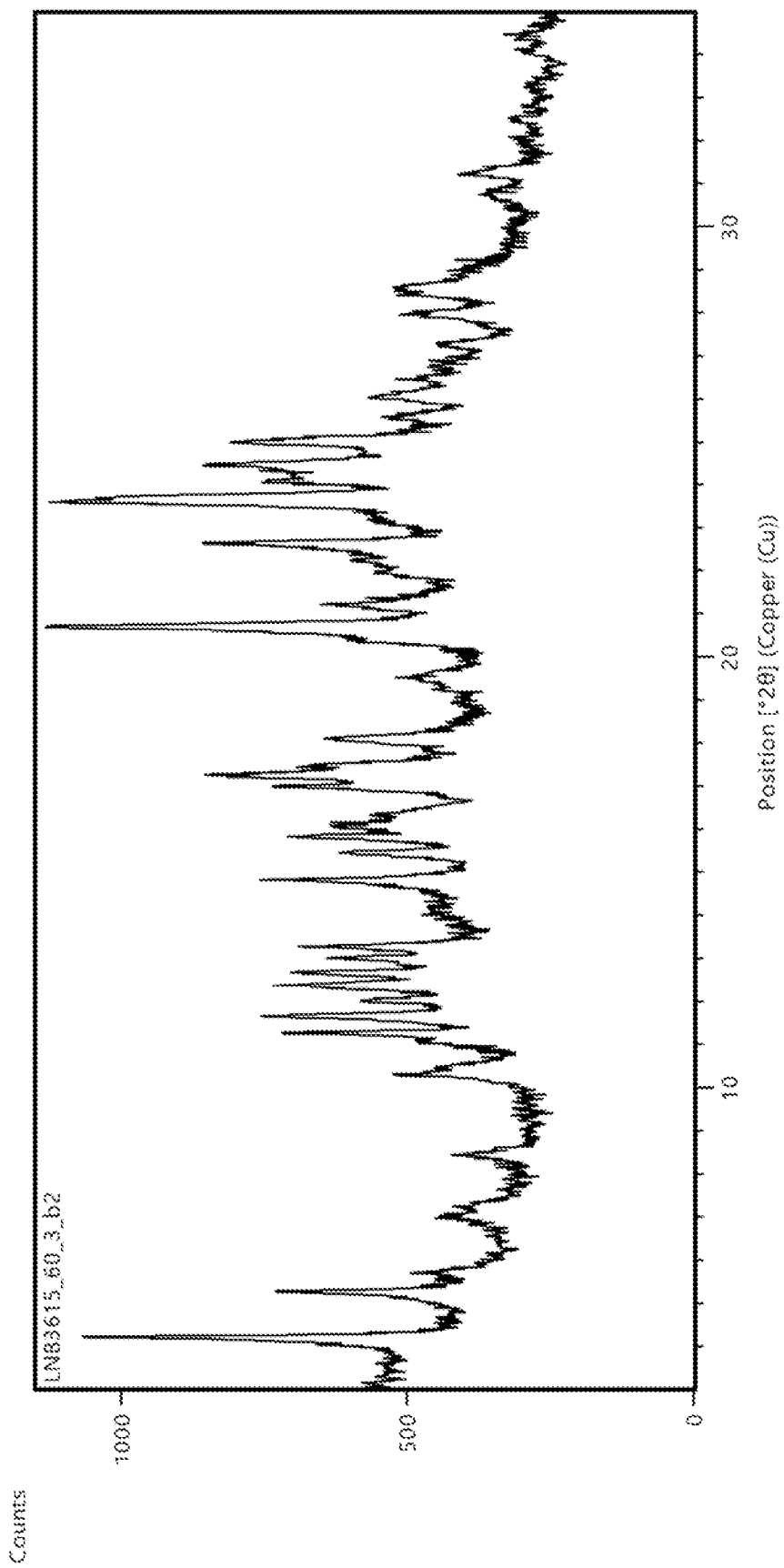
FIG. 18 depicts a XRPD pattern of a fumarate salt of Compound I Pattern 2 (Acetone:water (90:10 v/v)).

In yet another aspect, the invention features a crystalline form of a fumarate salt of Compound I which has characteristic peaks in the powder X-ray diffraction (XRPD) pattern as shown in FIG. 18.

In yet another aspect, the invention features a crystalline form of a fumarate salt of Compound I which has characteristic peaks in the powder X-ray diffraction (XRPD) pattern at values of two theta (° 2θ) as shown in Table 12.

In another aspect, the invention features a crystalline form of a fumarate salt of Compound I which has characteristic peaks in the powder X-ray diffraction (XRPD) pattern at values of two theta (° 2θ) of 4.6, 11.2, 14.6, 19.9, 20.5, 24.2, 24.6, and 25.2.

In another aspect, the invention features a crystalline form of a fumarate salt of Compound I which has characteristic peaks in the powder X-ray diffraction (XRPD) pattern at values of two theta (° 2θ) of 4.6, 11.2, 14.6, 19.3, 19.9, 20.3, 20.5, 22.8, 23.1, 23.3, 23.6, 24.2, 24.3, 24.6, 25.2, 25.6, 26.5, and 27.3.

Figure 19:
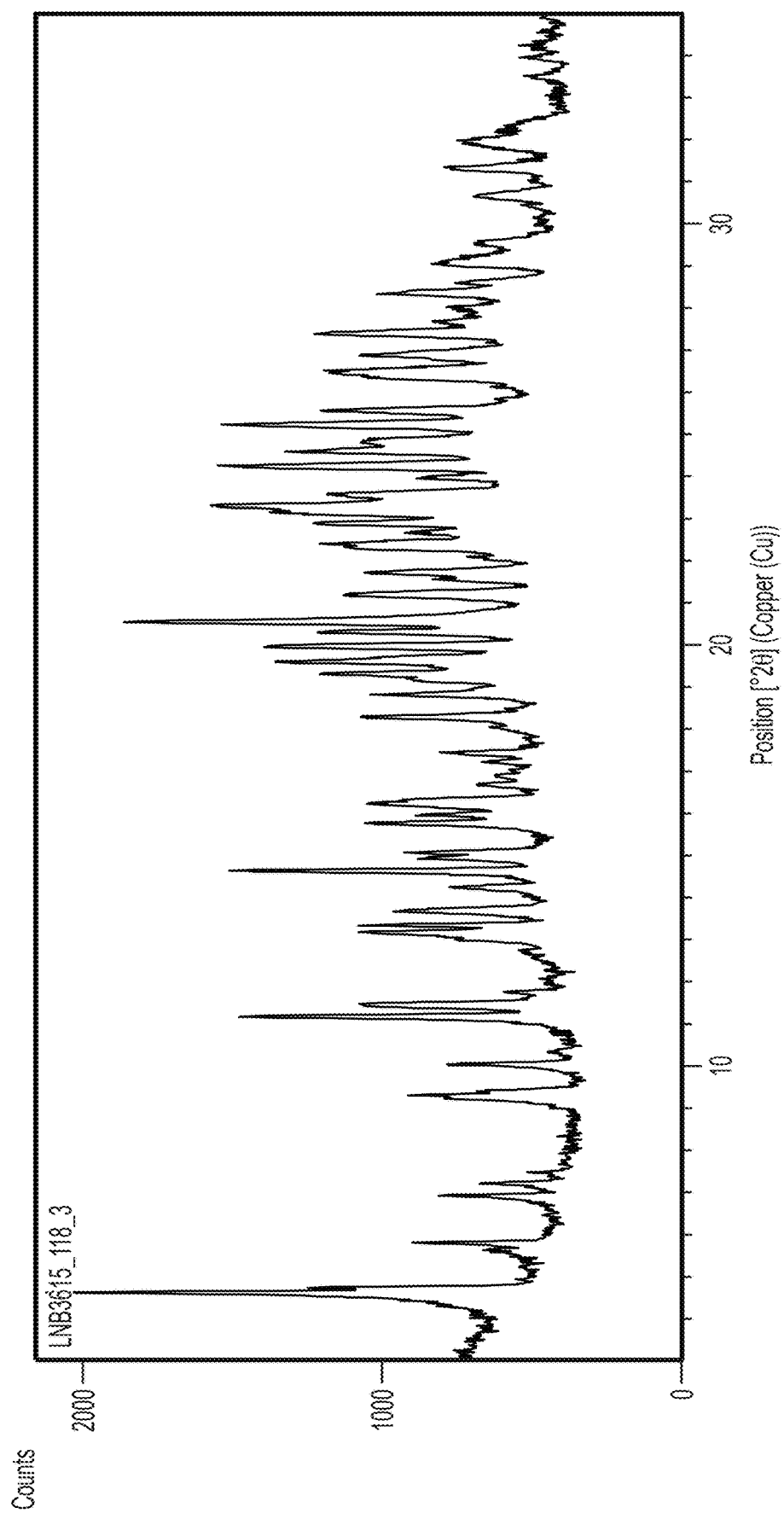
FIG. 19 depicts a XRPD pattern of a fumarate salt of Compound I Pattern 3 (2-propanol/water (re-preparations)).

In yet another aspect, the invention features a crystalline form of a fumarate salt of Compound I which has characteristic peaks in the powder X-ray diffraction (XRPD) pattern as shown in FIG. 19.

In yet another aspect, the invention features a crystalline form of a fumarate salt of Compound I which has characteristic peaks in the powder X-ray diffraction (XRPD) pattern at values of two theta (° 2θ) as shown in Table 13.

In another aspect, the invention features a crystalline form of a fumarate salt of Compound I which has characteristic peaks in the powder X-ray diffraction (XRPD) pattern at values of two theta (° 2θ) of 11.4, 14.0, 19.6, 19.8, 22.9, 23.2, 24.3, and 24.5.

In another aspect, the invention features a crystalline form of a fumarate salt of Compound I which has characteristic peaks in the powder X-ray diffraction (XRPD) pattern at values of two theta (° 2θ) of 11.4, 13.3, 14.0, 16.0, 16.2, 19.6, 19.8, 21.6, 22.4, 22.9, 23.2, 23.6, 24.3, 24.5, 25.6, and 26.6.

Figure 20:
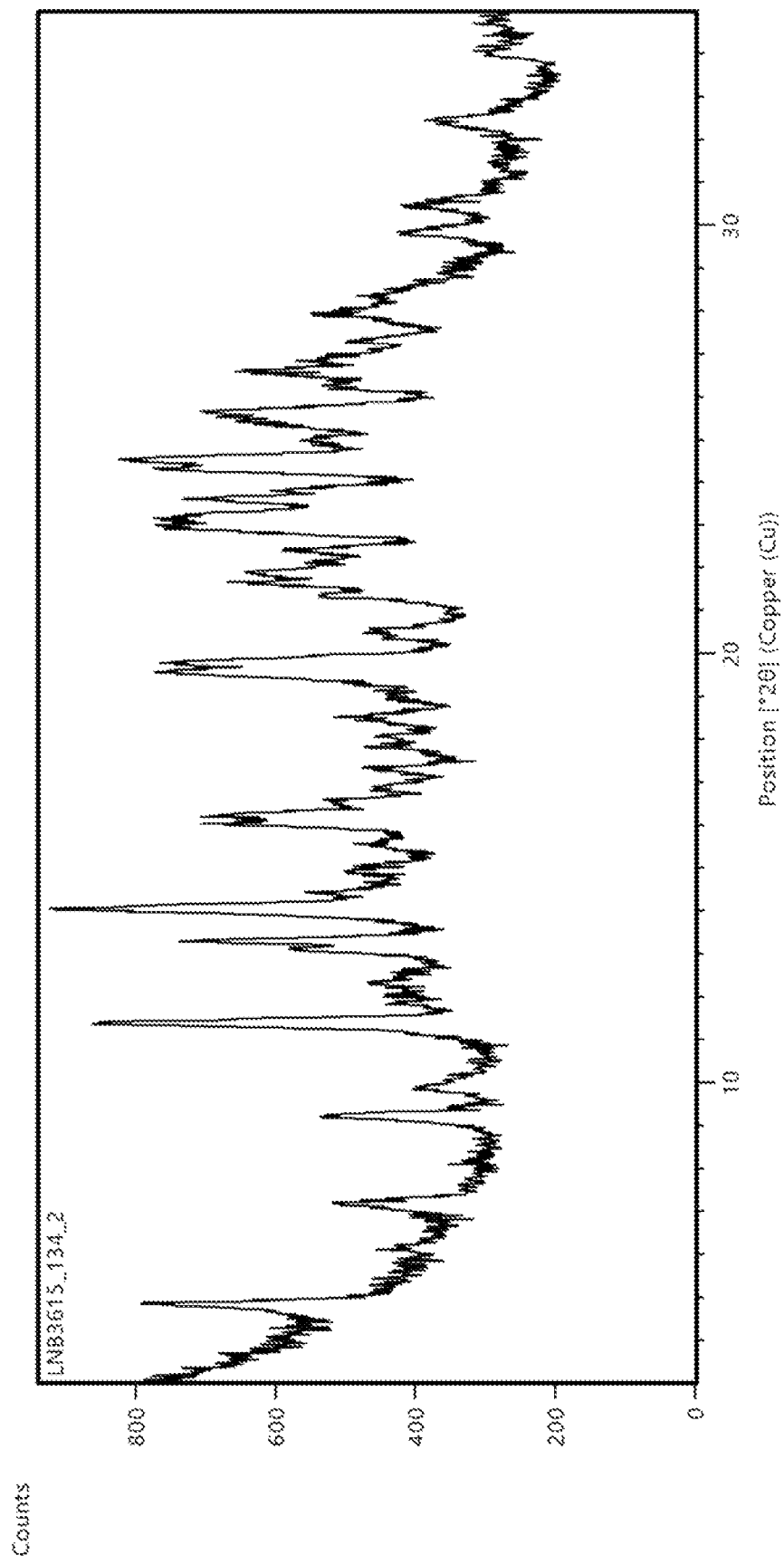
FIG. 20 depicts a XRPD pattern of a fumarate salt of Compound I Pattern 4 (2-propanol/water (scale-up)).

In yet another aspect, the invention features a crystalline form of a fumarate salt of Compound I which has characteristic peaks in the powder X-ray diffraction (XRPD) pattern as shown in FIG. 20.

In yet another aspect, the invention features a crystalline form of a fumarate salt of Compound I which has characteristic peaks in the powder X-ray diffraction (XRPD) pattern at values of two theta (° 2θ) as shown in Table 14.

In another aspect, the invention features a crystalline form of a fumarate salt of Compound I which has characteristic peaks in the powder X-ray diffraction (XRPD) pattern at values of two theta (° 2θ) of 12.3, 21.0, 23.2, 24.0, 24.7, 25.0, 25.4, 26.0, 26.4, and 27.5.

In another aspect, the invention features a crystalline form of a fumarate salt of Compound I which has characteristic peaks in the powder X-ray diffraction (XRPD) pattern at values of two theta (° 2θ) of 6.6, 12.0, 12.3, 13.1, 13.6, 16.1, 19.6, 20.5, 21.0, 21.5, 23.2, 24.0, 24.7, 25.0, 25.4, 26.0, 26.4, 27.5, 28.0, and 28.7.

Figure 21:
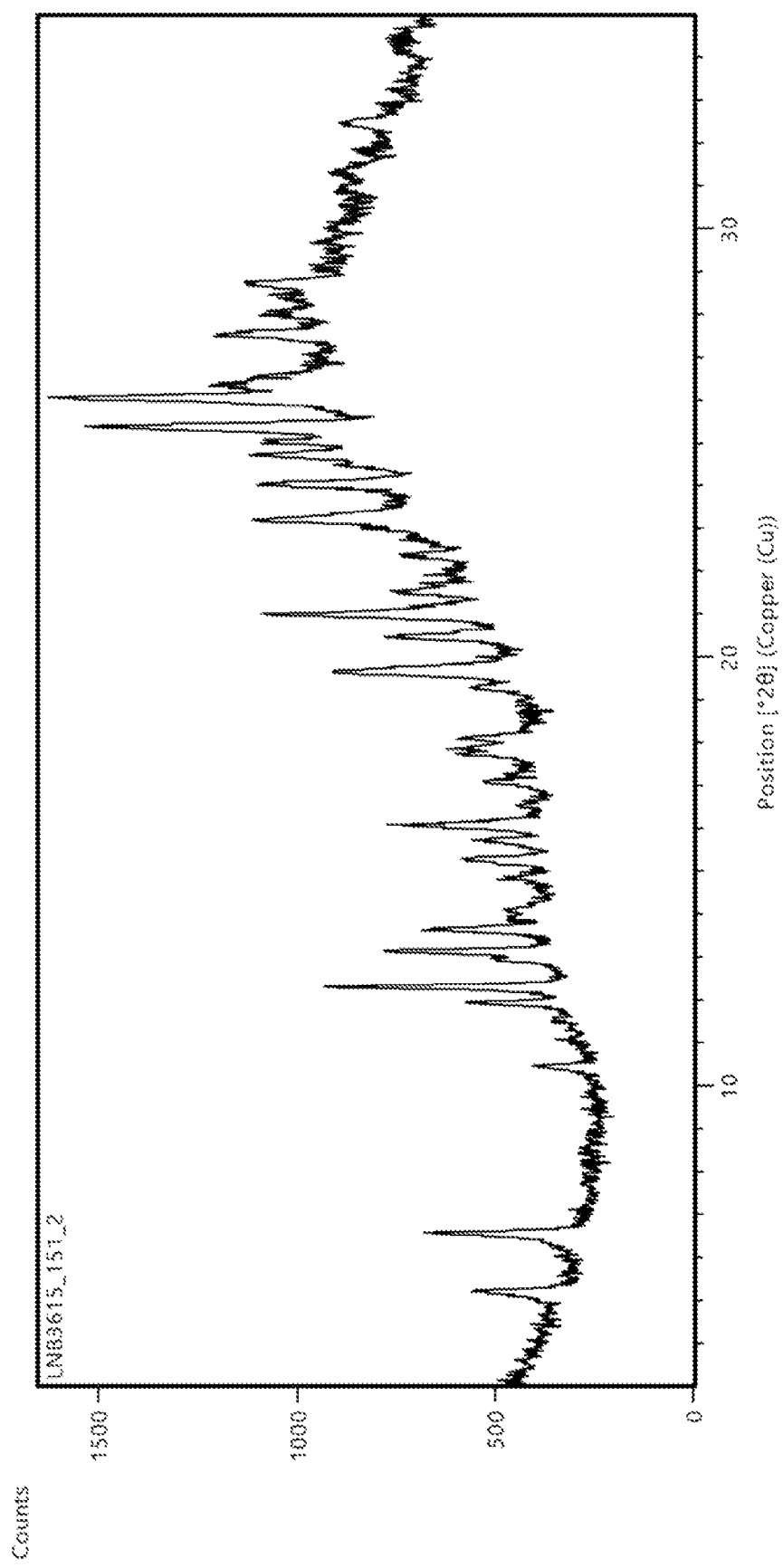
FIG. 21 depicts a XRPD pattern of a fumarate salt of Compound I Pattern 5 (Pattern 4 after slurrying in water).

In yet another aspect, the invention features a crystalline form of a fumarate salt of Compound I which has characteristic peaks in the powder X-ray diffraction (XRPD) pattern as shown in FIG. 21.

In yet another aspect, the invention features a crystalline form of a fumarate salt of Compound I which has characteristic peaks in the powder X-ray diffraction (XRPD) pattern at values of two theta (° 2θ) as shown in Table 15.

In another aspect, the invention features a crystalline form of a fumarate salt of Compound I which has characteristic peaks in the powder X-ray diffraction (XRPD) pattern at values of two theta (° 2θ) of 21.5, 22.2, 23.1, 23.9, 24.1, 24.6, 25.2, and 26.0.

In another aspect, the invention features a crystalline form of a fumarate salt of Compound I which has characteristic peaks in the powder X-ray diffraction (XRPD) pattern at values of two theta (° 2θ) of 13.4, 16.3, 18.5, 21.5, 22.2, 23.1, 23.6, 23.9, 24.1, 24.6, 25.2, 26.0, 26.9, and 28.9.

Figure 22:
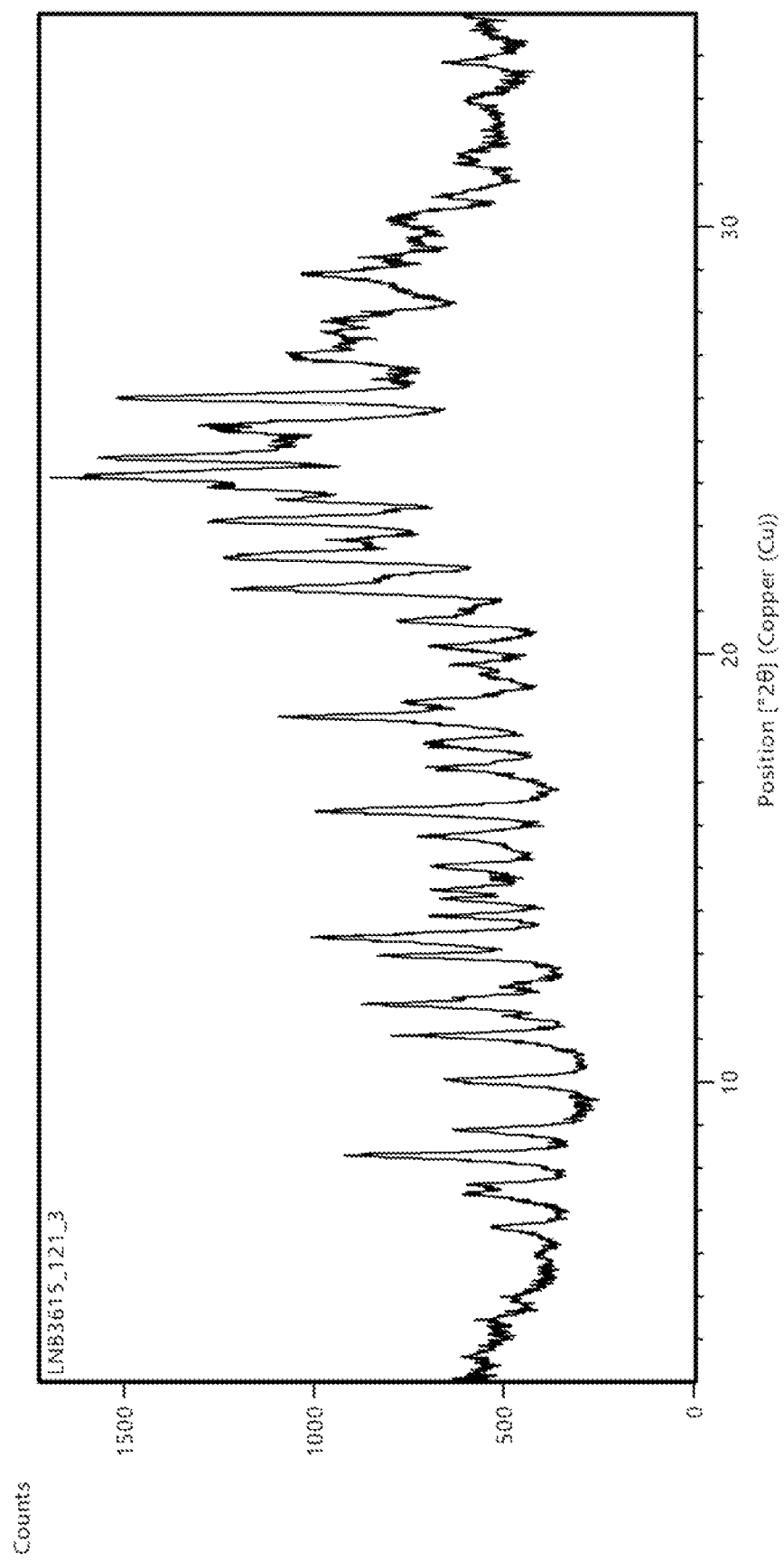
FIG. 22 depicts a XRPD pattern of a fumarate salt of Compound I Pattern 6 (Acetonitrile during re-preparations).

In yet another aspect, the invention features a crystalline form of a fumarate salt of Compound I which has characteristic peaks in the powder X-ray diffraction (XRPD) pattern as shown in FIG. 22.

In yet another aspect, the invention features a crystalline form of a fumarate salt of Compound I which has characteristic peaks in the powder X-ray diffraction (XRPD) pattern at values of two theta (° 2θ) as shown in Table 16.

In another aspect, the invention features a crystalline form of a fumarate salt of Compound I which has characteristic peaks in the powder X-ray diffraction (XRPD) pattern at values of two theta (° 2θ) of 6.6, 12.3, 13.6, 16.0, 19.2, 19.6, 20.4, 21.0, 21.1, 22.3, 23.2, 24.0, 25.3, and 26.0.

In another aspect, the invention features a crystalline form of a fumarate salt of Compound I which has characteristic peaks in the powder X-ray diffraction (XRPD) pattern at values of two theta (° 2θ) of 6.6, 12.3, 13.6, 16.0, 17.7, 18.1, 19.2, 19.6, 20.4, 21.0, 21.1, 22.3, 23.2, 24.0, 24.6, 25.0, 25.3, 26.0, 26.3, and 27.4.

Figure 23:
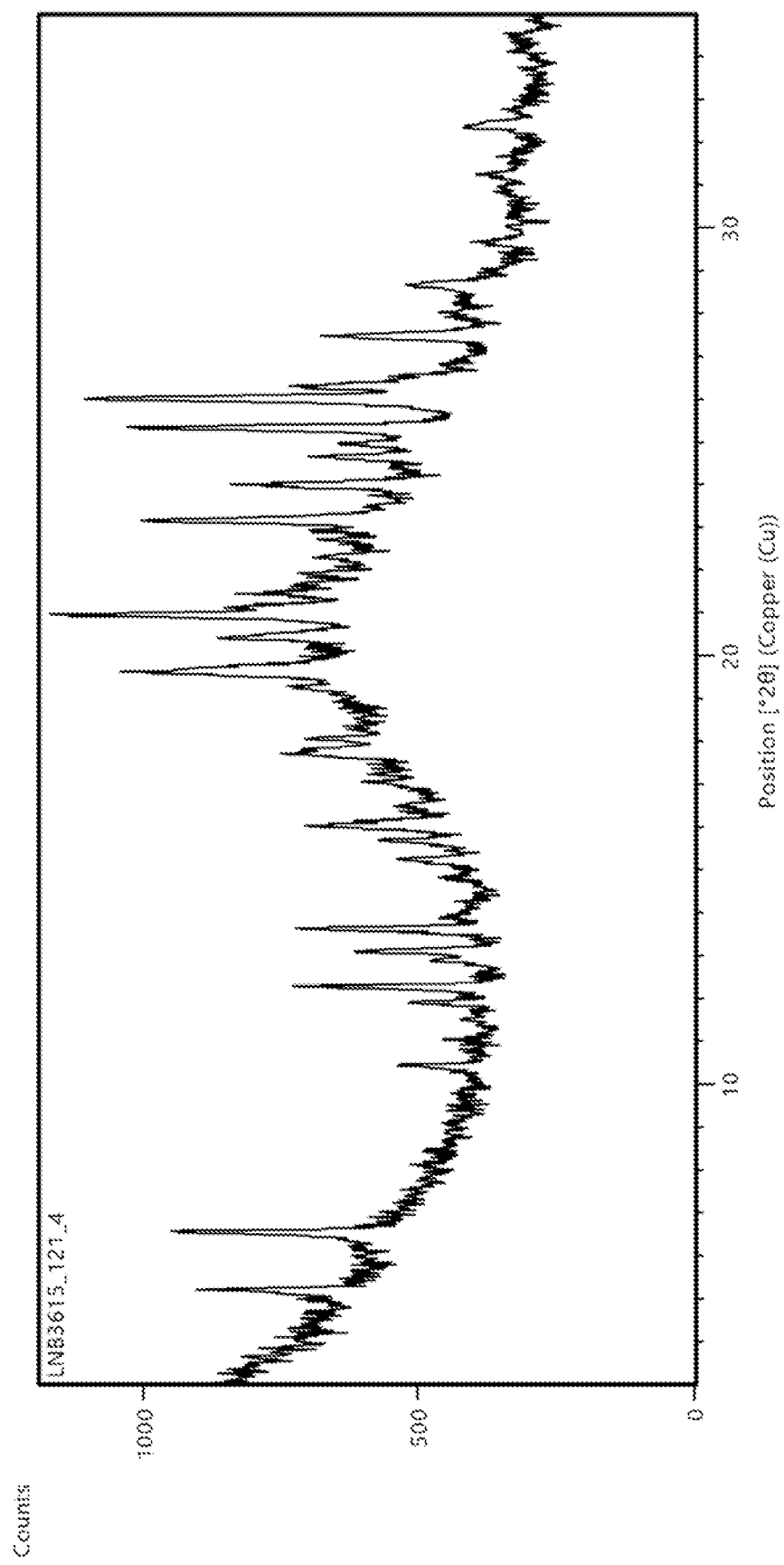
FIG. 23 depicts a XRPD pattern of a fumarate salt of Compound I Pattern 7 (1-butanol during re-preparations).

In yet another aspect, the invention features a crystalline form of a fumarate salt of Compound I which has characteristic peaks in the powder X-ray diffraction (XRPD) pattern as shown in FIG. 23.

In yet another aspect, the invention features a crystalline form of a fumarate salt of Compound I which has characteristic peaks in the powder X-ray diffraction (XRPD) pattern at values of two theta (° 2θ) as shown in Table 17.

In yet another aspect, the invention features a crystalline form of a fumarate salt of Compound I which has characteristic peaks in the powder X-ray diffraction (XRPD) pattern at values of two theta (° 2θ) of 13.2, 20.3, 22.7, 21.4, 21.9, 23.6, 24.0, 24.4, and 25.6.

In another aspect, the invention features a crystalline form of a fumarate salt of Compound I which has characteristic peaks in the powder X-ray diffraction (XRPD) pattern at values of two theta (° 2θ) of 9.4, 11.2, 13.2, 18.6, 20.3, 21.4, 21.7, 21.9, 22.7, 23.2, 23.6, 24.0, 24.4, 25.6, 26.8, and 28.5.

Figure 24:
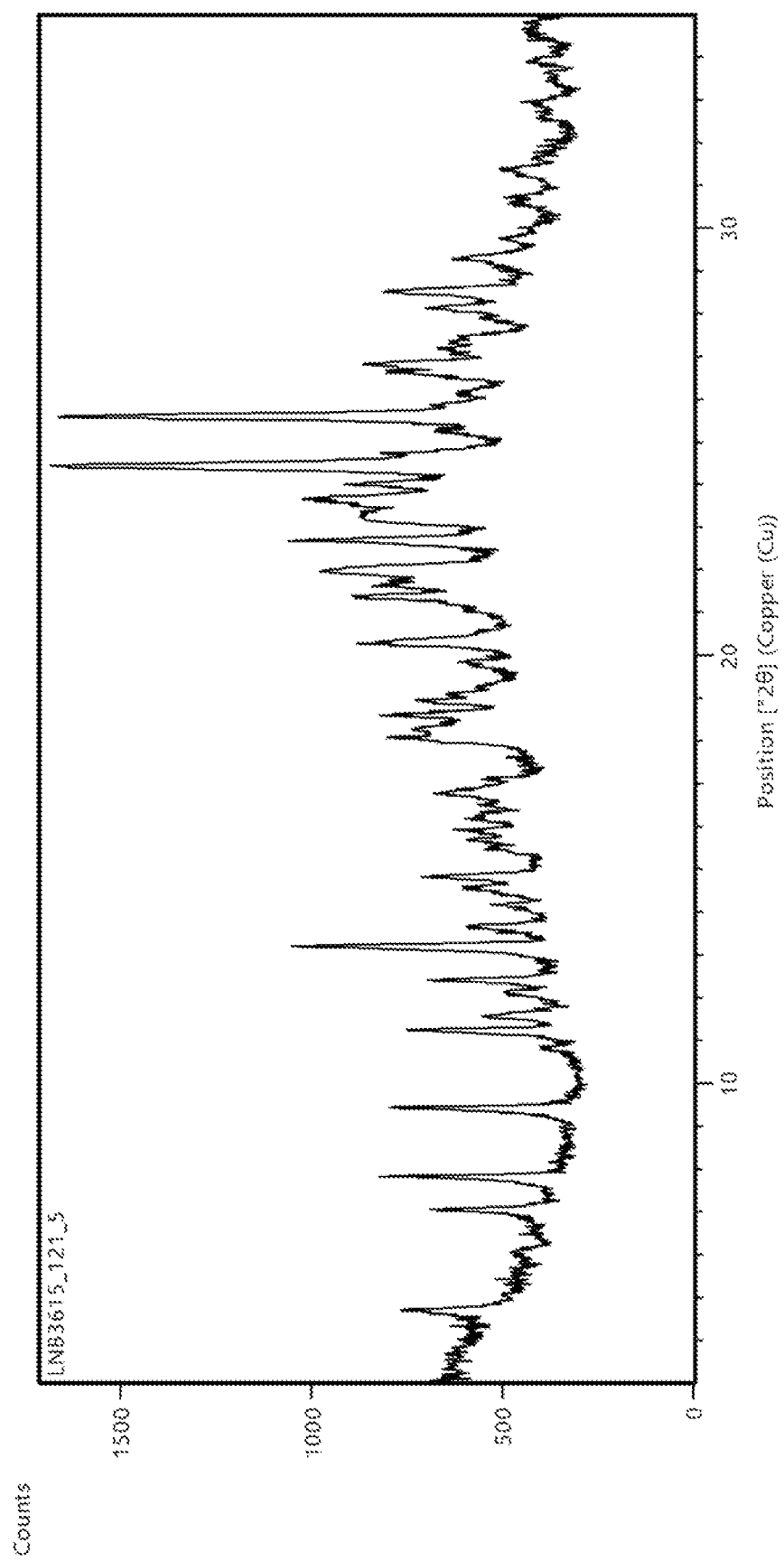
FIG. 24 depicts a XRPD pattern of a fumarate salt of Compound I Pattern 8 (1-propanol during re-preparations).

In yet another aspect, the invention features a crystalline form of a fumarate salt of Compound I which has characteristic peaks in the powder X-ray diffraction (XRPD) pattern as shown in FIG. 24.

In yet another aspect, the invention features a crystalline form of a fumarate salt of Compound I which has characteristic peaks in the powder X-ray diffraction (XRPD) pattern at values of two theta (° 2θ) as shown in Table 18.

In another aspect, the invention features a crystalline form of a cholesteryl sulfate salt of Compound I which has characteristic peaks in the powder X-ray diffraction (XRPD) pattern at values of two theta (° 2θ) of 5.0, 5.8, 11.9, 12.3, 12.6, 16.1, 16.8, and 17.0.

In another aspect, the invention features a crystalline form of a cholesteryl sulfate salt of Compound I which has characteristic peaks in the powder X-ray diffraction (XRPD) pattern at values of two theta (° 2θ) of 5.0, 5.8, 10.5, 11.9, 12.3, 12.6, 13.2, 16.1, 16.8, 17.0, and 19.1.

Figure 7:
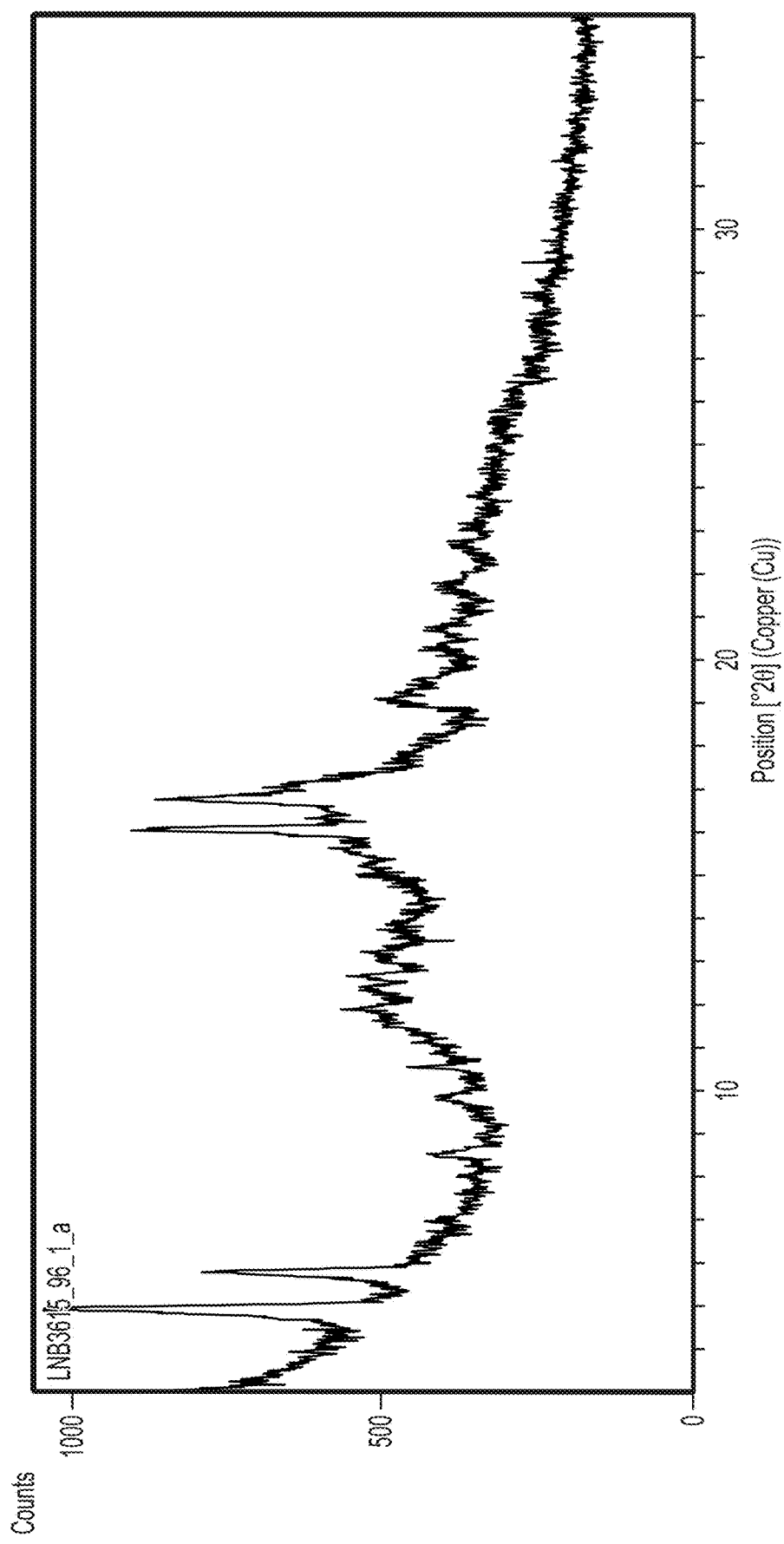
FIG. 7 depicts a XRPD pattern of a cholesteryl sulfate Pattern 1 (Methanol).

In yet another aspect, the invention features a crystalline form of a cholesteryl sulfate salt of Compound I which has characteristic peaks in the powder X-ray diffraction (XRPD) pattern as shown in FIG. 7.

In yet another aspect, the invention features a crystalline form of a cholesteryl sulfate salt of Compound I which has characteristic peaks in the powder X-ray diffraction (XRPD) pattern at values of two theta (° 2θ) as shown in Table 1.

In another aspect, the invention features a crystalline form of a cholesteryl sulfate salt of Compound I which has characteristic peaks in the powder X-ray diffraction (XRPD) pattern at values of two theta (° 2θ) of 7.4, 12.4, 13.1, 15.6, 16.3, 17.7, and 19.8.

In another aspect, the invention features a crystalline form of a cholesteryl sulfate salt of Compound I which has characteristic peaks in the powder X-ray diffraction (XRPD) pattern at values of two theta (° 2θ) of 7.4, 12.4, 13.1, 13.4, 14.4, 15.6, 16.3, 17.7, 19.5, and 19.8.

Figure 8:
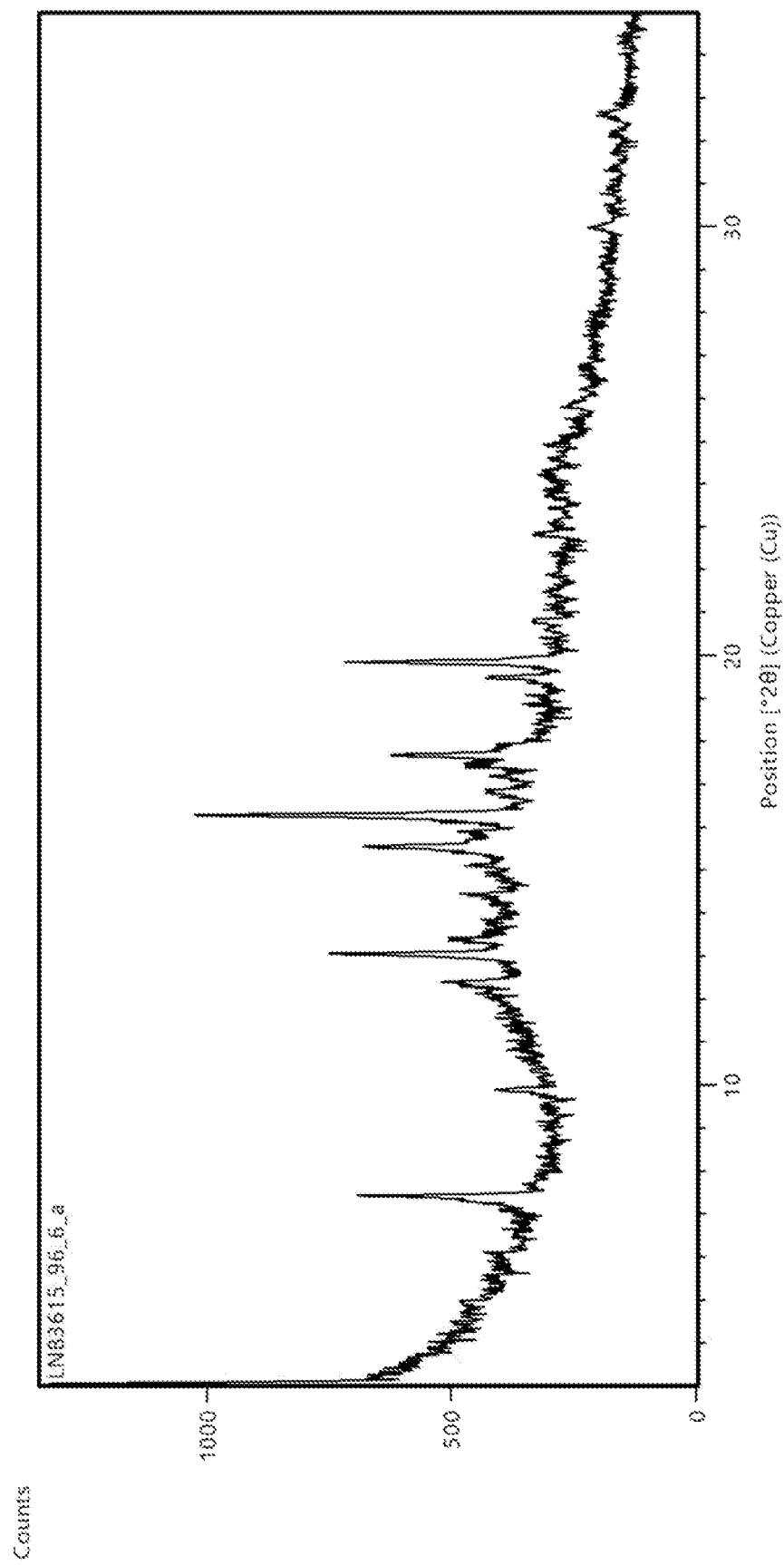
FIG. 8 depicts a XRPD pattern of a cholesteryl sulfate Pattern 2 (Acetonitrile:Ethylene glycol (90:10 v/v)).

In yet another aspect, the invention features a crystalline form of a cholesteryl sulfate salt of Compound I which has characteristic peaks in the powder X-ray diffraction (XRPD) pattern as shown in FIG. 8.

In yet another aspect, the invention features a crystalline form of a cholesteryl sulfate salt of Compound I which has characteristic peaks in the powder X-ray diffraction (XRPD) pattern at values of two theta (° 2θ) as shown in Table 2.

In another aspect, the invention features a crystalline form of an oxalate salt of Compound I which has characteristic peaks in the powder X-ray diffraction (XRPD) pattern at values of two theta (° 2θ) of 5.0, 7.3, 13.4, 17.3, 21.3, 22.5, 22.9, and 24.7.

In another aspect, the invention features a crystalline form of an oxalate salt of Compound I which has characteristic peaks in the powder X-ray diffraction (XRPD) pattern at values of two theta (° 2θ) of 5.0, 7.3, 12.2, 13.2, 13.4, 15.0, 16.2, 17.3, 18.6, 20.1, 21.3, 22.5, 22.9, 23.3, 24.4, and 24.7.

Figure 13:
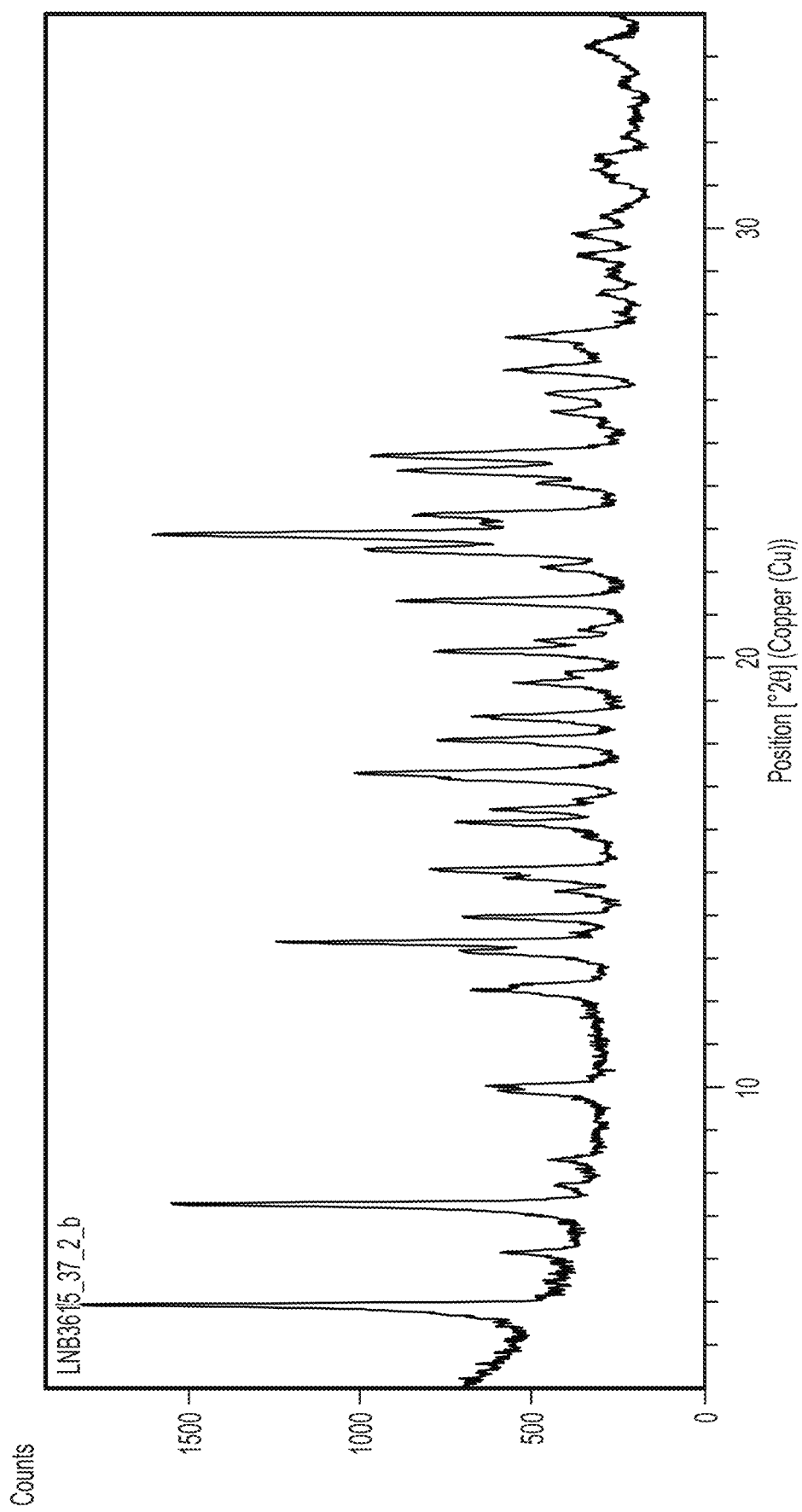
FIG. 13 depicts a XRPD pattern of an oxalate salt of Compound I Pattern 1 (2-propanol).

In yet another aspect, the invention features a crystalline form of an oxalate salt of Compound I which has characteristic peaks in the powder X-ray diffraction (XRPD) pattern as shown in FIG. 13.

In yet another aspect, the invention features a crystalline form of an oxalate salt of Compound I which has characteristic peaks in the powder X-ray diffraction (XRPD) pattern at values of two theta (° 2θ) as shown in Table 7.

In another aspect, the invention features a crystalline form of an oxalate salt of Compound I which has characteristic peaks in the powder X-ray diffraction (XRPD) pattern at values of two theta (° 2θ) of 3.8, 4.3, 8.1, 19.8, 20.7, 22.3, 24.9, and 25.6.

In another aspect, the invention features a crystalline form of an oxalate salt of Compound I which has characteristic peaks in the powder X-ray diffraction (XRPD) pattern at values of two theta (° 2θ) of 3.8, 4.3, 7.0, 8.1, 18.2, 18.3, 19.1, 19.8, 20.3, 20.7, 21.1, 22.3, 22.8, 23.2, 23.5, 24.0, 24.6, 24.9, and 25.6.

Figure 14:
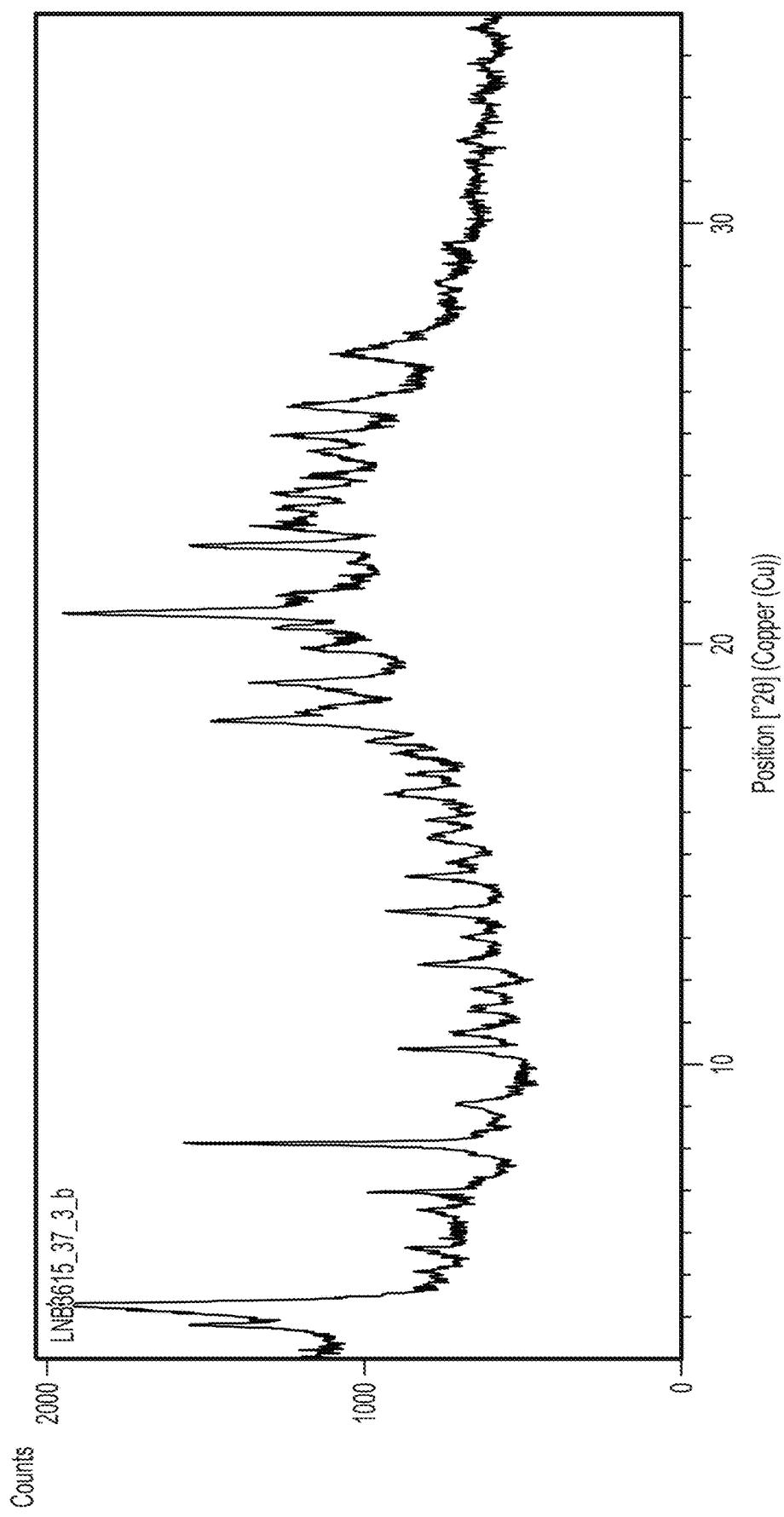
FIG. 14 depicts a XRPD pattern of an oxalate salt of Compound I Pattern 2 (Acetone:water (90:10 v/v)).

In yet another aspect, the invention features a crystalline form of an oxalate salt of Compound I which has characteristic peaks in the powder X-ray diffraction (XRPD) pattern as shown in FIG. 14.

In yet another aspect, the invention features a crystalline form of an oxalate salt of Compound I which has characteristic peaks in the powder X-ray diffraction (XRPD) pattern at values of two theta (° 2θ) as shown in Table 8.

In another aspect, the invention features a crystalline form of an esylate salt of Compound I which has characteristic peaks in the powder X-ray diffraction (XRPD) pattern at values of two theta (° 2θ) of 5.4, 9.8, 10.8, 18.8, 19.7, 21.1, 21.8, and 22.3.

In another aspect, the invention features a crystalline form of an esylate salt of Compound I which has characteristic peaks in the powder X-ray diffraction (XRPD) pattern at values of two theta (° 2θ) of 5.4, 9.8, 10.8, 11.8, 14.4, 15.1, 15.6, 17.2, 17.7, 18.8, 19.0, 19.7, 21.1, 21.5, 21.8, and 22.3.

Figure 15:
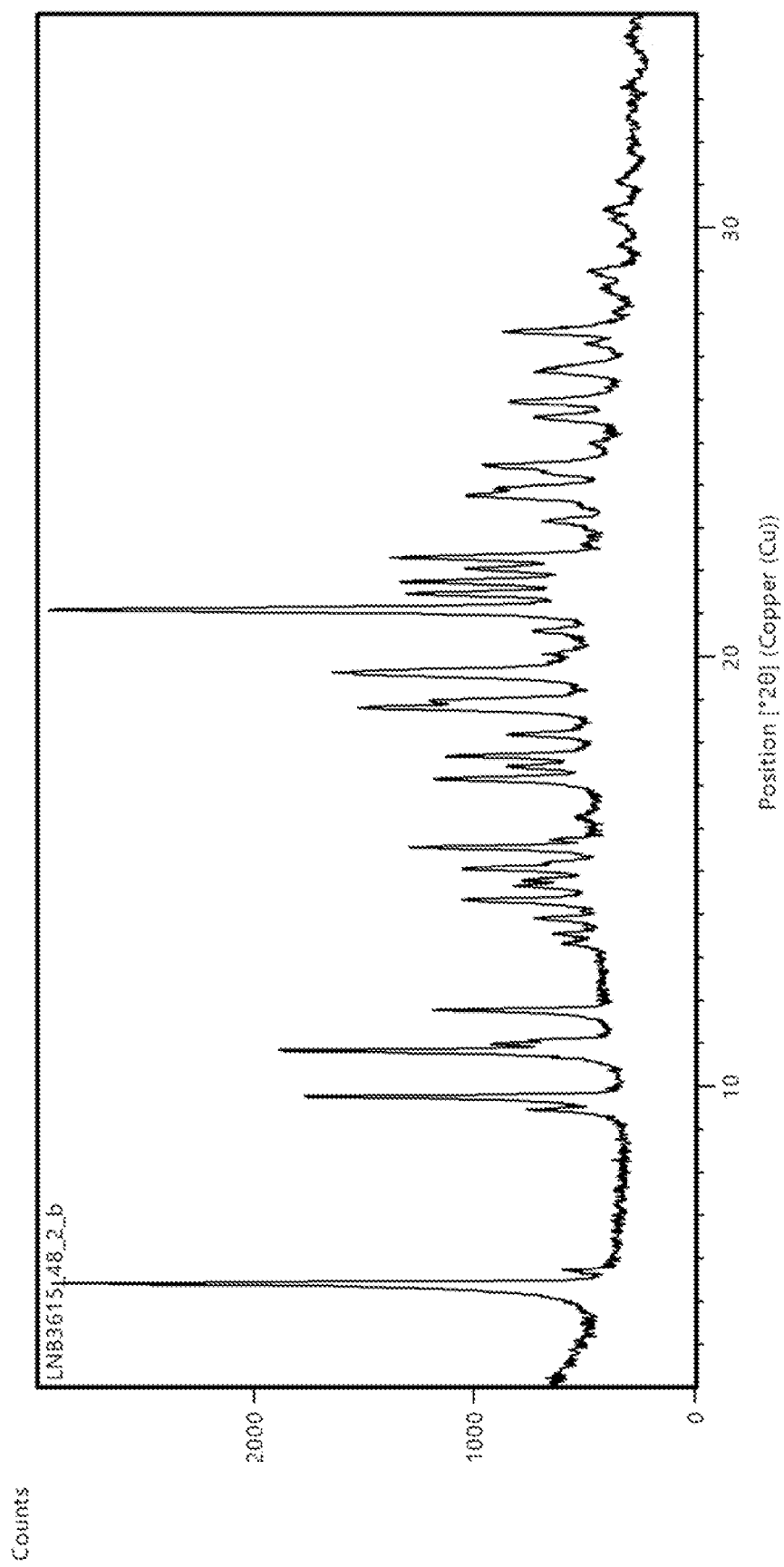
FIG. 15 depicts a XRPD pattern of an esylate salt of Compound I Pattern 1 (2-Propanol).

In yet another aspect, the invention features a crystalline form of an esylate salt of Compound I which has characteristic peaks in the powder X-ray diffraction (XRPD) pattern as shown in FIG. 15.

In yet another aspect, the invention features a crystalline form of an esylate salt of Compound I which has characteristic peaks in the powder X-ray diffraction (XRPD) pattern at values of two theta (° 2θ) as shown in Table 9.

In another aspect, the invention features a crystalline form of an esylate salt of Compound I which has characteristic peaks in the powder X-ray diffraction (XRPD) pattern at values of two theta (° 2θ) of 5.4, 10.8, 11.0, 14.5, 17.3, 18.7, 19.6, 21.0, 21.4, and 22.1.

In another aspect, the invention features a crystalline form of an esylate salt of Compound I which has characteristic peaks in the powder X-ray diffraction (XRPD) pattern at values of two theta (° 2θ) of 5.4, 9.7, 10.8, 11.0, 14.5, 15.0, 16.0, 17.3, 17.7, 18.7, 19.6, 21.0, 21.4, 22.1, and 24.0.

Figure 16:
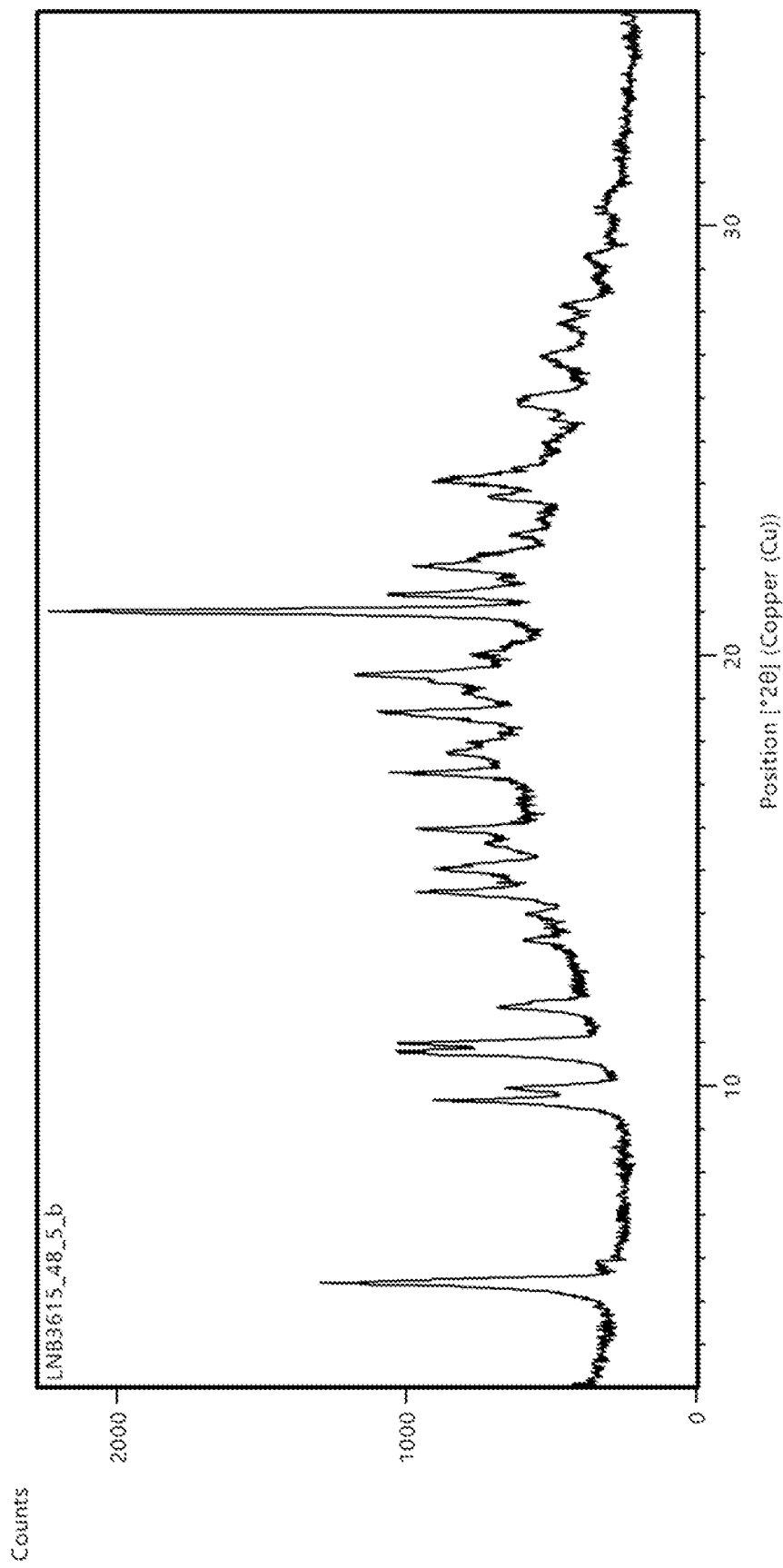
FIG. 16 depicts a XRPD pattern of an esylate salt of Compound I Pattern 2 (Anisole).

In yet another aspect, the invention features a crystalline form of an esylate salt of Compound I which has characteristic peaks in the powder X-ray diffraction (XRPD) pattern as shown in FIG. 16.

In yet another aspect, the invention features a crystalline form of an esylate salt of Compound I which has characteristic peaks in the powder X-ray diffraction (XRPD) pattern at values of two theta (° 2θ) as shown in Table 10.

In another aspect, the invention features a crystalline form of a benzoate salt of Compound I which has characteristic peaks in the powder X-ray diffraction (XRPD) pattern at values of two theta (° 2θ) of 5.1, 10.2, 13.2, 14.0, 20.4, 21.9 and 25.3.

In another aspect, the invention features a crystalline form of a benzoate salt of Compound I which has characteristic peaks in the powder X-ray diffraction (XRPD) pattern at values of two theta (° 2θ) of 5.1, 10.2, 11.9, 13.2, 13.8, 14.0, 16.0, 16.7, 20.4, 21.9, 23.1, 23.5, 24.5, and 25.3.

Figure 25:
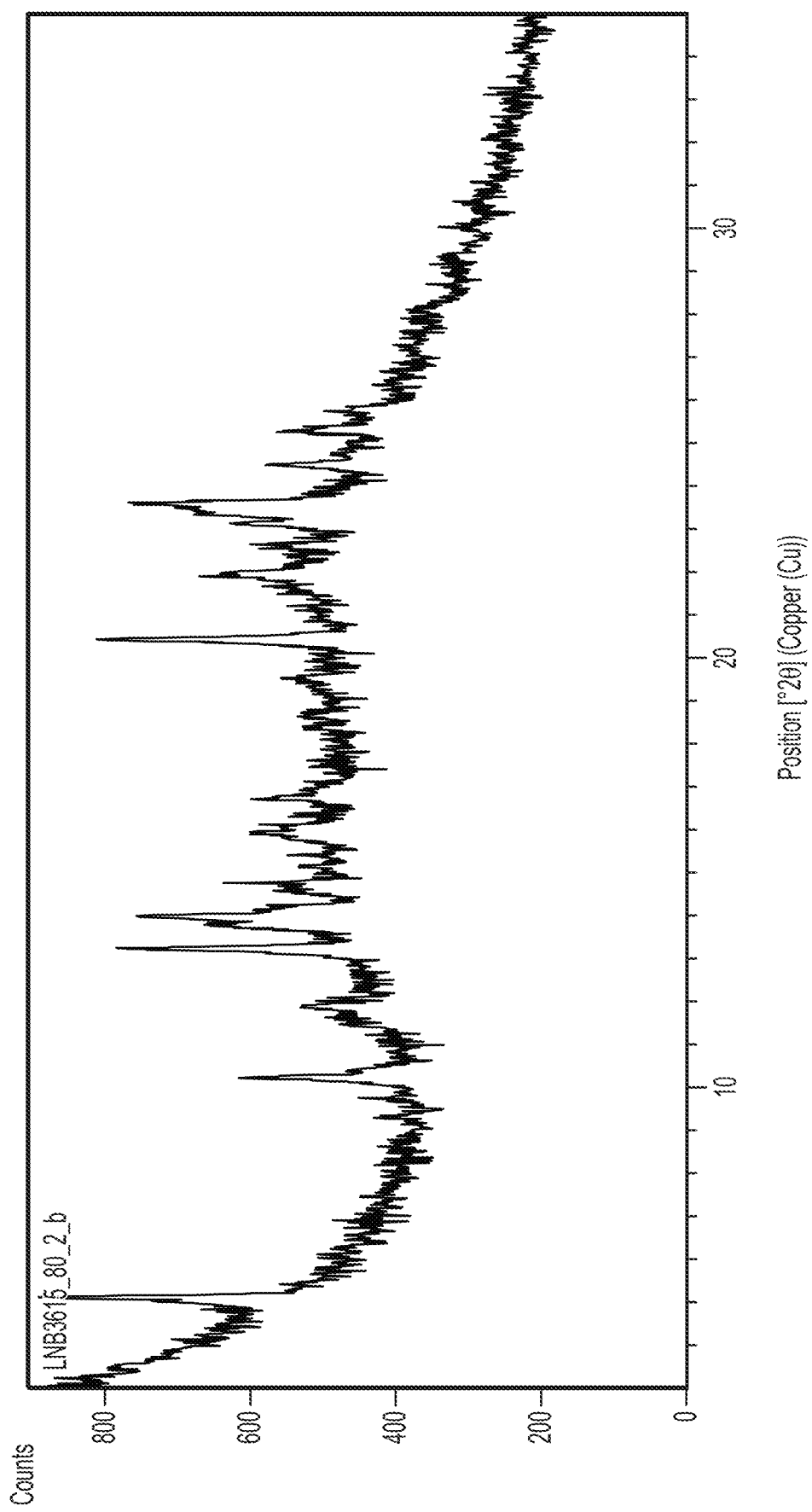
FIG. 25 depicts a XRPD pattern of a benzoate salt of Compound I Pattern 1 (2-propanol).

In yet another aspect, the invention features a crystalline form of a benzoate salt of Compound I which has characteristic peaks in the powder X-ray diffraction (XRPD) pattern as shown in FIG. 25.

In yet another aspect, the invention features a crystalline form of a benzoate salt of Compound I which has characteristic peaks in the powder X-ray diffraction (XRPD) pattern at values of two theta (° 2θ) as shown in Table 19.

In another aspect, the invention features a crystalline form of a succinate salt of Compound I which has characteristic peaks in the powder X-ray diffraction (XRPD) pattern at values of two theta (° 2θ) of 4.2, 5.1, 6.6, 9.9, 14.1, 18.0, and 24.1.

In another aspect, the invention features a crystalline form of a succinate salt of Compound I which has characteristic peaks in the powder X-ray diffraction (XRPD) pattern at values of two theta (° 2θ) of 4.2, 5.1, 6.6, 8.0, 9.9, 10.3, 13.1, 14.1, 14.6, 17.6, 18.0, 18.5, 19.0, 19.9, 20.8, 22.2, 22.4, 23.4, and 24.1.

Figure 26:
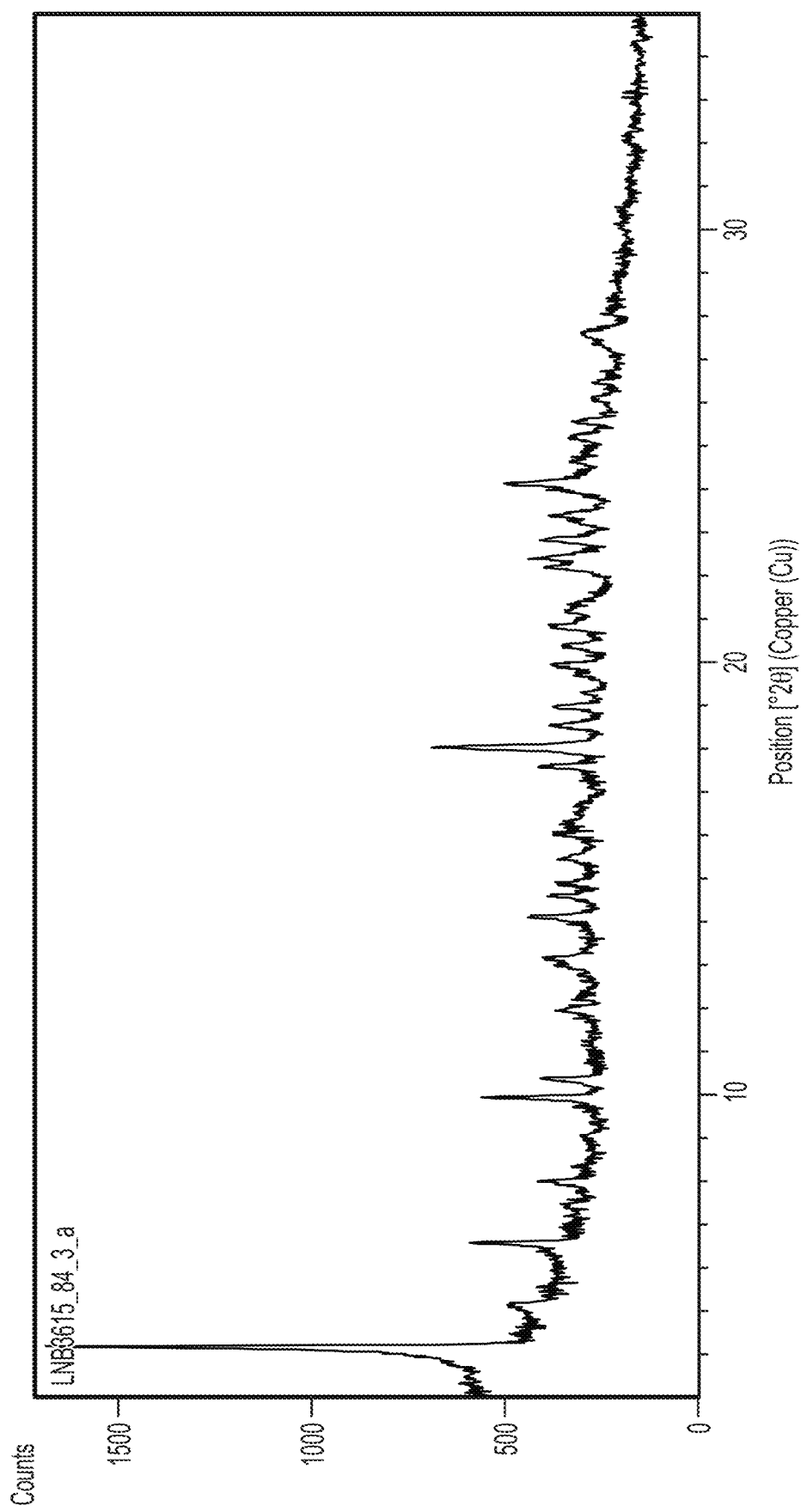
FIG. 26 depicts a XRPD pattern of a succinate salt of Compound I Pattern 1 (Acetone:Water (90:10 v/v)).
Figure 27:
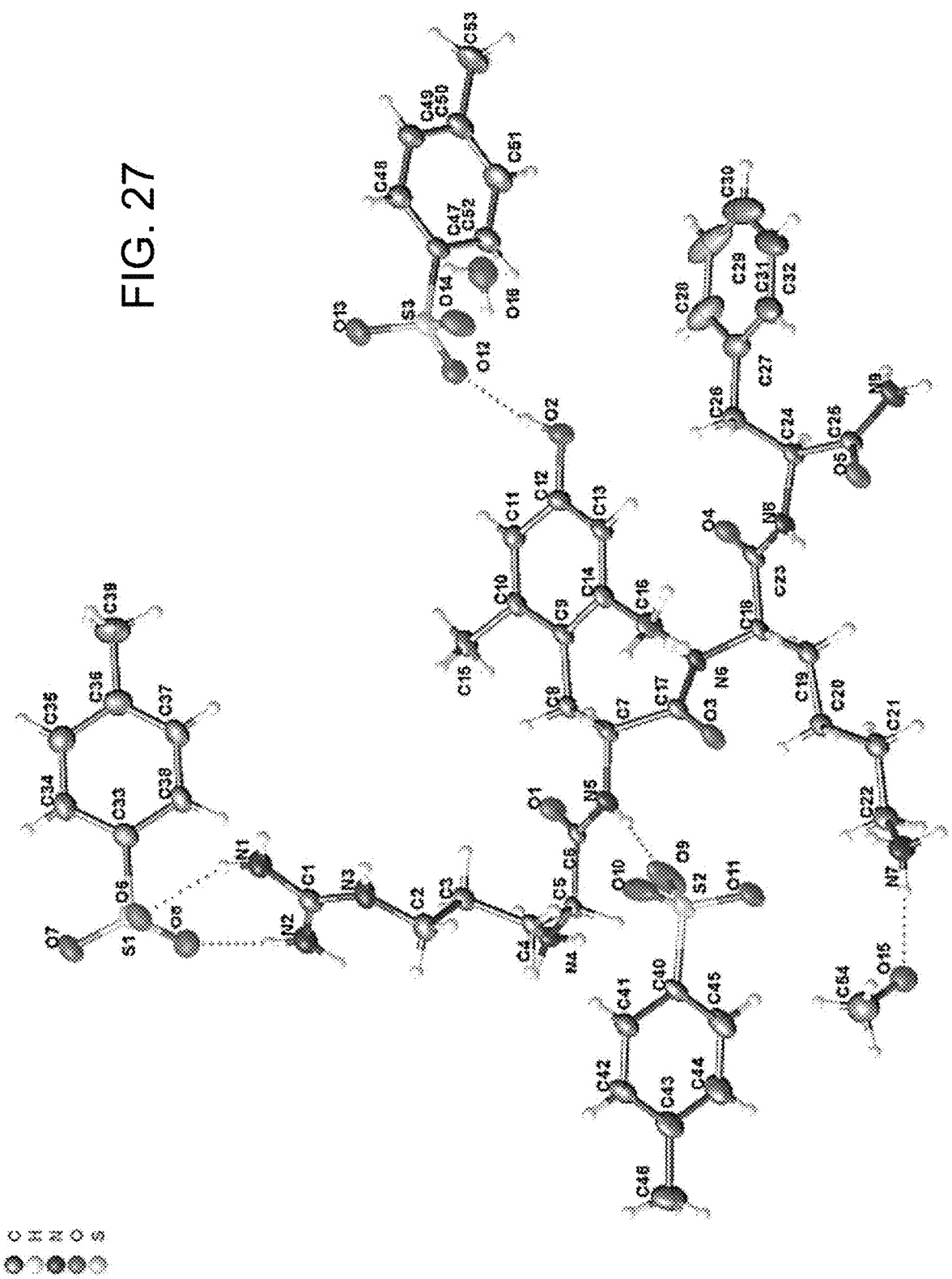
FIG. 27 depicts a view of MTP-131 tosylate, Pattern 2 asymmetric unit with atom labelling. All non-hydrogen atoms are shown with thermal ellipsoids set at the 50% probability level.
Figure 28:
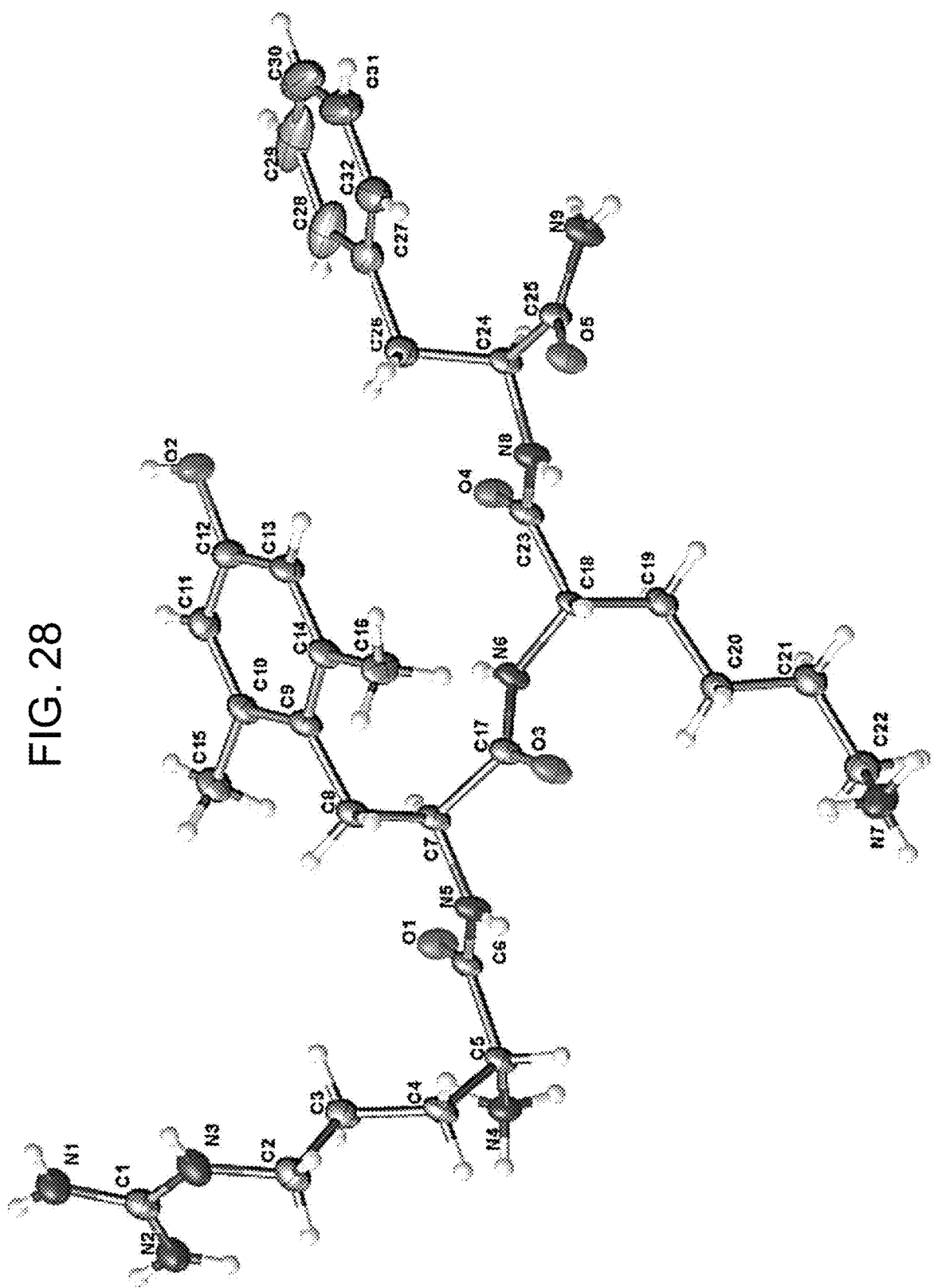
FIG. 28 depicts a view of MTP-131 parent molecule with atom labels. All non-hydrogen atoms are shown with thermal ellipsoids set at the 50% probability level.
Figure 29:
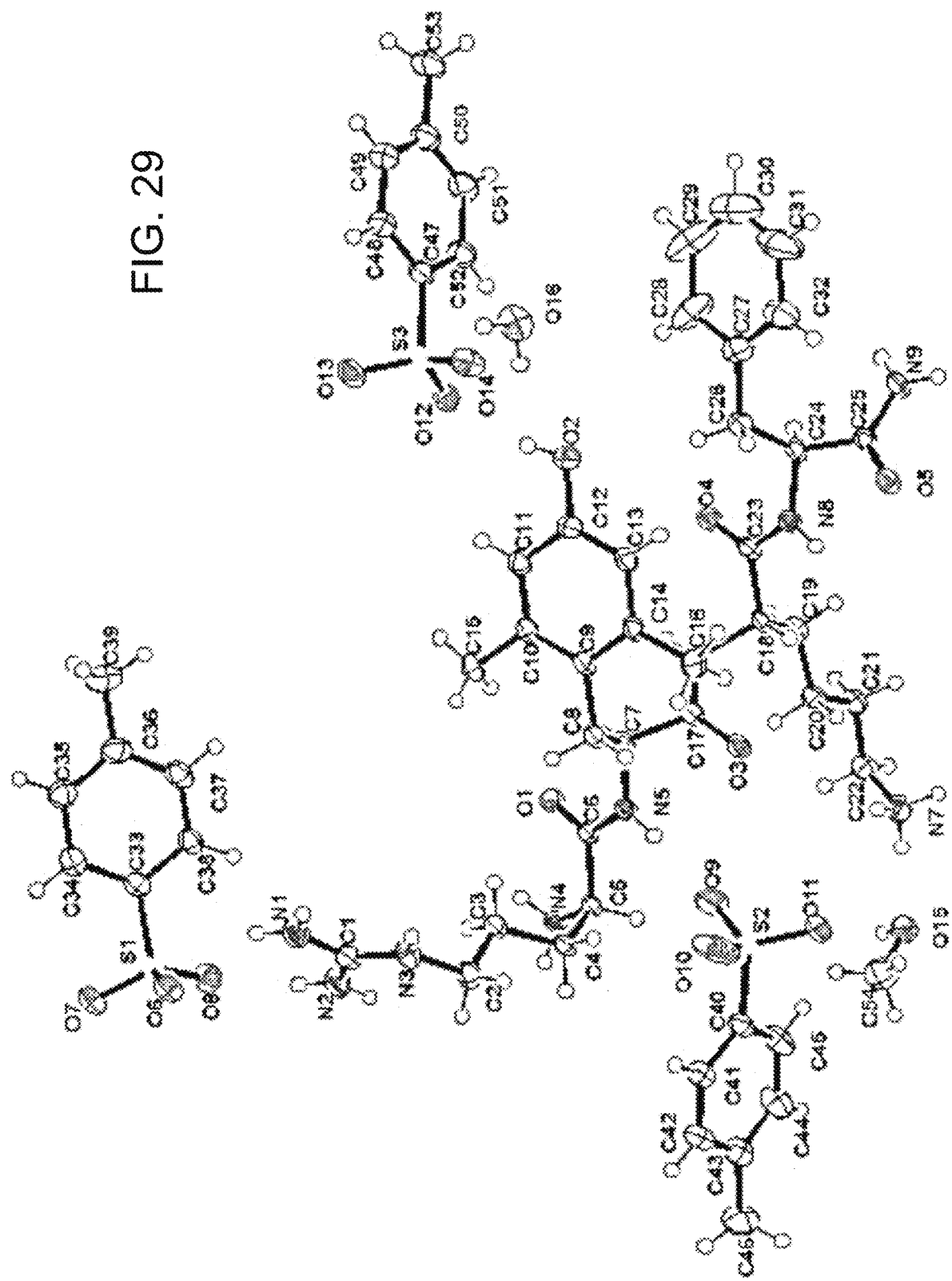
FIG. 29 depicts an ORTEP view of MTP-131 tosylate, Pattern 2 asymmetric unit with atom labels. All non-hydrogen atoms are shown with thermal ellipsoids set at the 50% probability level.

In yet another aspect, the invention features a crystalline form of a succinate salt of Compound I which has characteristic peaks in the powder X-ray diffraction (XRPD) pattern as shown in FIG. 26.

In yet another aspect, the invention features a crystalline form of a succinate salt of Compound I which has characteristic peaks in the powder X-ray diffraction (XRPD) pattern at values of two theta (° 2θ) as shown in Table 20.

In yet another aspect, the invention features a crystalline form of a hydrochloride salt of Compound I which has characteristic peaks in the powder X-ray diffraction (XRPD) pattern as shown in FIG. 1.

Figure 2:
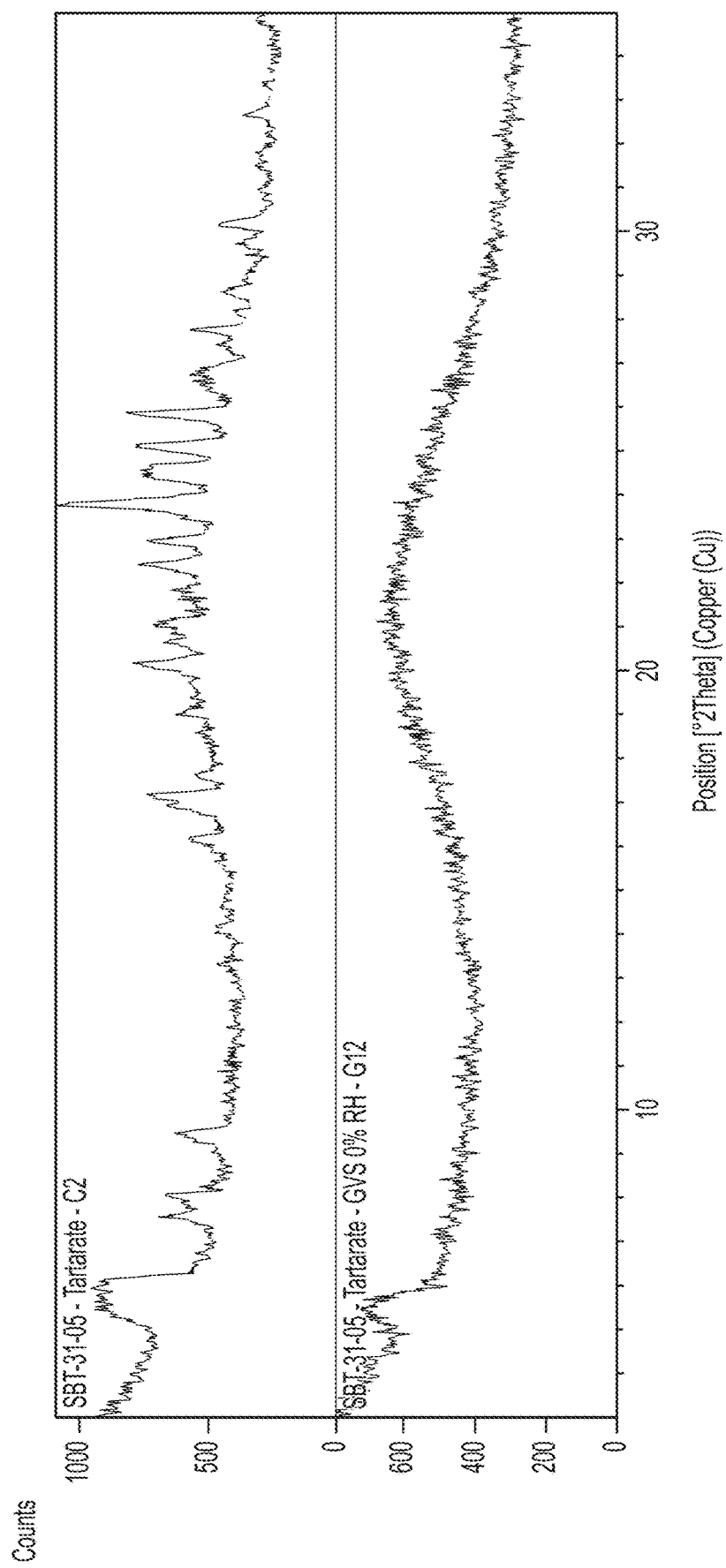
FIG. 2 depicts a XRPD pattern of a tartrate salt of Compound I.

In yet another aspect, the invention features a crystalline form of a tartrate salt of Compound I which has characteristic peaks in the powder X-ray diffraction (XRPD) pattern as shown in FIG. 2.

Figure 4:
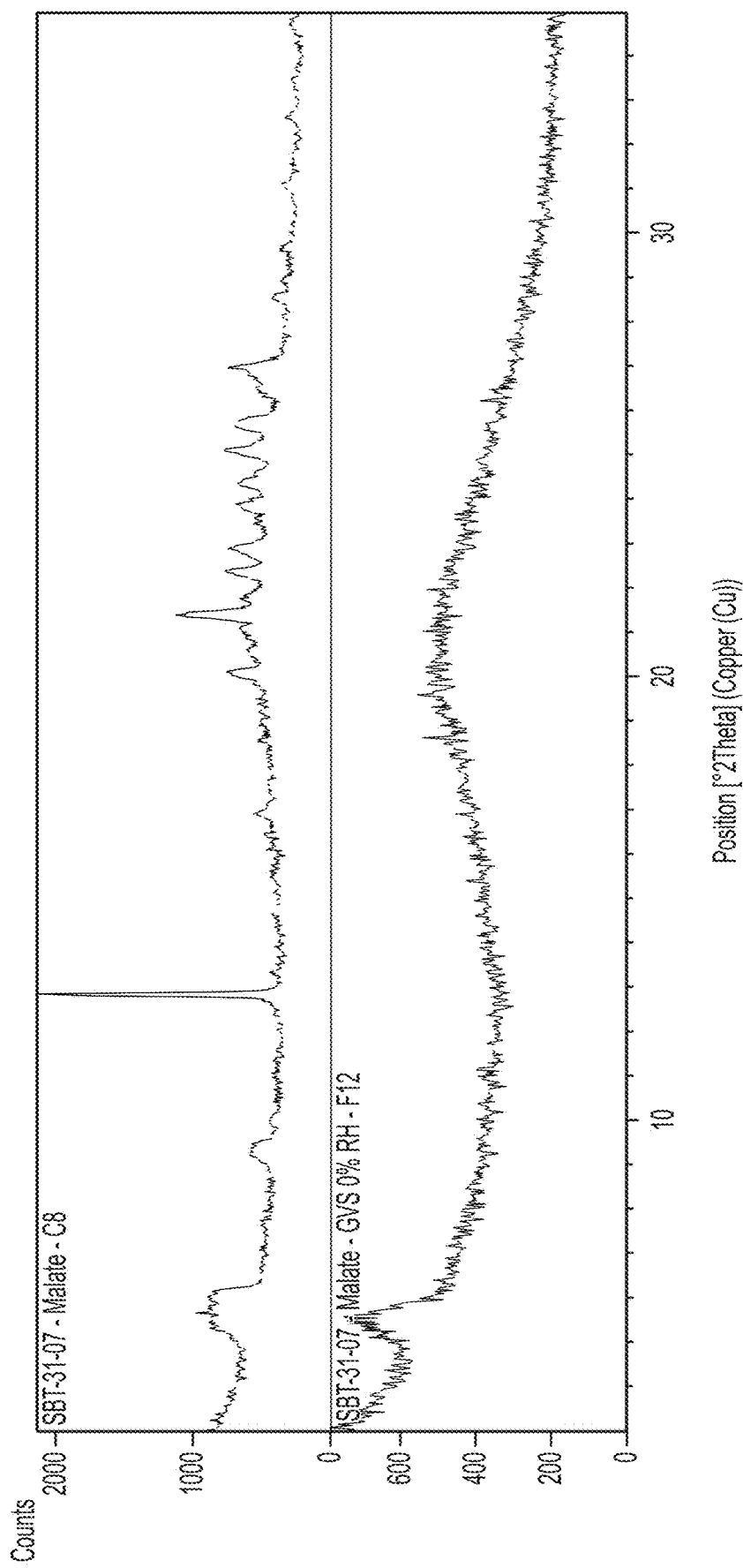
FIG. 4 depicts a XRPD pattern of a malate salt of Compound I.

In yet another aspect, the invention features a crystalline form of a malate salt of Compound I which has characteristic peaks in the powder X-ray diffraction (XRPD) pattern as shown in FIG. 4.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

In one embodiment, the present invention features a crystalline form of Compound I which has characteristic peaks in the powder X-ray diffraction (XRPD) pattern as shown in any one of FIGS. 1-26 and which is substantially pure. For example, the crystalline form can be at least 90% pure, preferably at least 95% pure, or more preferably at least 98%.

In another embodiment, the present invention features a crystalline form of Compound I which has characteristic peaks in the powder X-ray diffraction (XRPD) pattern at values of two theta (° 2θ) as shown in any one of Tables 1-20 and which is substantially pure. For example, the crystalline form can be at least 90% pure, preferably at least 95% pure, or more preferably at least 98%.

Methods of Making the Crystalline Salts

In certain embodiments, the invention relates to a method for the preparation of a crystalline salt of a compound having the structure of formula (I), comprising a) providing a freebase mixture of a compound of formula (I) in a first organic solvent; b) contacting the freebase mixture with a reagent solution comprising an acid and optionally a second organic solvent under conditions sufficient to form a mixture comprising a salt of the compound of formula (I); and c) crystallizing the salt of the compound of formula (I) from the mixture comprising a salt of the compound of formula (I).

In certain embodiments, the invention relates to a method for the preparation of a crystalline salt of a compound having the structure of formula (I), comprising a) providing a first salt mixture of a compound of formula (I) in a first organic solvent; b) contacting the first salt mixture with a reagent solution comprising an acid and optionally a second organic solvent under conditions sufficient to form a mixture comprising a second salt of the compound of formula (I); and c) crystallizing the second salt of the compound of formula (I) from the mixture comprising a second salt of the compound of formula (I).

In certain embodiments, the invention relates to a method for the preparation of a crystalline salt of a compound having the structure of formula (I), comprising a) providing a first mixture comprising a protected form of a compound of formula (I) in a first organic solvent; b) contacting the first mixture with a reagent solution comprising an acid and optionally a second organic solvent under conditions sufficient to deprotect the protected form of the compound of formula (I) and to form a mixture comprising a salt of the compound of formula (I); and c) crystallizing the salt of the compound of formula (I) from the mixture comprising a salt of the compound of formula (I).

In certain embodiments, the mixture comprising a salt of the compound of formula (I) formed in step b) is a solution. In certain embodiments, the mixture formed in step b) is a slurry or a suspension.

In certain embodiments, the mixture comprising the salt of the compound of formula (I) is a solution, and the step of crystallizing the salt from the mixture comprises bringing the solution to supersaturation to cause the salt of the compound of formula (I) to precipitate out of solution.

In certain embodiments, bringing the mixture comprising the salt of a compound of formula (I) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the salt of a compound of formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the salt crystals, e.g., by filtering the crystals, by decanting fluid from the crystals, or by any other suitable separation technique. In further embodiments, the preparation method further comprises washing the crystals.

In certain embodiments, the preparation method further comprises inducing crystallization. The method can also comprise the step of drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, the freebase mixture of a compound of formula (I) in a first organic solvent is a slurry. In certain embodiments, the freebase mixtures of a compound of formula (I) in a first organic solvent is a solution.

In certain embodiments, the first organic solvent and the second organic solvent, if present, comprise acetone, anisole, methanol, 1-butanol, 2-butanone, iso-butanol, tert-butanol, sec-butanol, cyclopentyl methylester (CPME), benezotrifluoride (BTF), 1-propanol, 2-propanol (IPA), water, dichloromethane, anisole, acetonitrile, ethylene glycol, tert-butyl methyl ether (t-BME), DMSO, ethylene glycol, toluene, tetrahydrofuran (THF), heptane, acetonitrile, N,N-dimethylacetamide (DMA), dimethylformamide (DMF), dimethylsulfoxide (DMSO), 1,4-dioxane, 2-ethoxy ethanol, heptane, isopropyl acetate, methyl acetate, 2-methyl THF, methyl isobutyl ketone (MIBK), 1-propanol, ethanol, ethyl acetate, hexanes, methyl acetate, isopropyl acetate, methylethyl ketone, 1,4-dioxane, methyl cyclohexane, N-methyl-2-pyrrolidone (NMP), or any combination thereof.

In certain embodiments, the first organic solvent and the second organic solvent, if present, are the same. In alterative embodiments, the first organic solvent and the second organic solvent, if present, are different.

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is ethanol.

In certain embodiments, washing the crystals comprises washing the crystalline compound of formula (I) with a solvent or a mixture of one or more solvents, which are described above. In certain embodiments, the solvent or mixture of solvents is cooled prior to washing.

Pharmaceutical Compositions

In certain embodiments, the present invention relates to pharmaceutical compositions comprising a crystalline compound or salt of a compound of formula (I) and one or more pharmaceutically acceptable excipients.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. Although the dosage could vary depending on the symptoms, age and body weight of the patient, the nature and severity of the disorder to be treated or prevented, the route of administration and the form of the drug, in general, a daily dosage of from 0.01 to 3000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is sterile and pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration or penetration of the corneal epithelium.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts", J. Pharm. Sci. 66: 1-19.).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Other representative salts include the copper and iron salts. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually or buccally); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin, microcrystalline cellulose, or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or antioxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively, or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, vaginal rings for sustained-release (e.g., polymeric vaginal rings) creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, intravitreal and intrasternal injection and infusion. Pharmaceutical compositions suitable for parenteral administration comprise one or more active compounds in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, metacresol, benzoic acid and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous, intravitreal or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of metabolism or excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect or the maximally tolerated dose. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, Cu, Fe or other metal salts.

The pharmaceutically acceptable acid addition salts can also exist as various solvates, such as with water, methanol, ethanol, dimethylformamide, dichloromethane, acetonitrile, acetone, ethyl acetate, cyclopentyl methyl ether and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Materials and Methods
X-Ray Diffraction

As used herein, XRPD data can be collected using a PANalytical X'Pert Pro X-ray Diffractometer, scanning the samples between 3 and 35° 2-theta. Material was loaded into a 96-well plate with Kapton or Mylar polymer film as the base. The samples were then loaded into the plate holder of a PANalytical X'Pert Pro X-ray Diffractometer running in transmission mode and analyzed, using the following experimental conditions:
  Raw Data Origin: XRD measurement (*.XRDML)
  Scan Axis: Gonio
  Start Position [° 2θ]: 3.0066
  End Position [° 2θ]: 34.9866
  Step Size [° 2θ]: 0.0130
  Scan Step Time [s]: 18.8700
  Scan Type: Continuous
  PSD Mode: Scanning
  PSD Length [° 2θ]: 3.35
  Offset [° 2θ]: 0.0000
  Divergence Slit Type: Fixed
  Divergence Slit Size [° ]: 1.0000
  Specimen Length [mm]: 10.00
  Measurement Temperature [° C.]: 25.00
  Anode Material: Cu
  K-Alpha1 [Å]: 1.54060
  K-Alpha2 [Å]: 1.54443
  K-Beta [Å]: 1.39225
  K-A2/K-A1 Ratio: 0.50000
  Generator Settings: 40 mA, 40 kV
  Diffractometer Type: 0000000011154173
  Diffractometer Number: 0
  Goniometer Radius [mm]: 240.00
  Dist. Focus-Diverg. Slit [mm]: 91.00
  Incident Beam Monochromator: No
  Spinning: No
Polarized Light Microscopy (PLM)

The presence of birefringence was determined using an Olympus BX50 polarizing microscope, equipped with a Motic camera and image capture software (Motic Images Plus 2.0). Material was dispersed in silicone oil prior to image capture. All images were recorded using the 20× objective, unless otherwise stated.

Thermogravimetric/Differential Thermal Analysis (TG/DTA)

Approximately 5 mg of material was weighed into an open aluminum pan and loaded into a Seiko TGA6200 simultaneous thermogravimetric/differential thermal analyzer (TG/DTA) and held at room temperature. The sample was then heated at a rate of 10° C./min from 20° C. to 300° C. during which time the change in sample weight was recorded along with any differential thermal events (DTA). Nitrogen was used as the purge gas, at a flow rate of 300 cm3/min.

Differential Scanning Calorimetry (DSC)

Approximately 5 mg of material was weighed into an aluminum DSC pan and sealed nonhermetically with a pierced aluminum lid. The sample pan was then loaded into a Seiko DSC6200 (equipped with a cooler) and held at 20° C. Once a stable heat-flow response was obtained, the sample and reference were heated to ca. 190° C. at a scan rate of 10° C./min and the resulting heat flow response monitored. Nitrogen was used as the purge gas, at a flow rate of 50 cm3/min.

Karl Fischer Coulometric Titration (KF)

Approximately 10-15 mg of solid material was accurately weighed into a glass weigh-boat. The solid was then manually introduced into the titration cell of a Mettler Toledo C30 Compact Titrator. The weigh-boat was back-weighed after the addition of the solid and the weight of the added solid entered on the instrument. The titration was initiated once the sample had fully dissolved in the cell. The water content was calculated automatically by the instrument as a percentage and the data printed.

$^1$H Nuclear Magnetic Resonance Spectroscopy (1H NMR)

$^1$H-NMR spectroscopic experiments were performed on a Bruker AV500 (frequency: 500 MHz). Experiments were performed in D20 and each sample was prepared to ca. 10 mM concentration.

Dynamic Vapor Sorption (DVS)

Approximately 10 mg of sample was placed into a mesh vapor sorption balance pan and loaded into a DVS-1 dynamic vapor sorption balance by Surface Measurement Systems. The sample was subjected to a ramping profile from 40-90% relative humidity (RH) at 10% increments, maintaining the sample at each step until a stable weight had been achieved (99.5% step completion). After completion of the sorption cycle, the sample was dried using the same procedure to 0% RH and then a second sorption cycle back to 40% RH. The weight changes during the sorption/desorption cycles were plotted, allowing the hygroscopic nature of the sample to be determined. XRPD analysis was then carried out on the remaining solid.

Gravimetric Vapor Sorption (GVS)

Approximately 10-20 mg of sample was placed into a mesh vapor sorption balance pan and loaded into an IGASorp Moisture Sorption Analyzer balance by Hiden Analytical. The sample was subjected to a ramping profile from 5-90% relative humidity (RH) at 10% increments, maintaining the sample at each step until a stable weight had been achieved (98% step completion). After completion of the sorption cycle, the sample was dried using the same procedure to 0% RH, and finally taken back to 40% RH. The weight changes during the sorption/desorption cycles were plotted, allowing the hygroscopic nature of the sample to be determined. XRPD analysis was then carried out on the remaining solid.

High Performance Liquid Chromatography-Ultraviolet Detection (HPLC-UV)
  Column: Aeris Peptide C18 3.6 Pm 250×4.6 mm column
  Mobile Phase A: 0.1% TFA in $H_2O$
  Mobile Phase B: 0.1% TFA in acetonitrile
  Diluent: $H_2O$: acetonitrile (90:10 v/v)
  Flow Rate: 1.0 mL/min
  Runtime: 36 minutes
  Column Temperature: 40° C.
  Autosampler Temperature: 5° C.
  Injection Volume: 30 μL
  Detection: 220 nm
  Sample Concentration: 0.4 mg/mL
  Gradient program:

| Time/min | Solvent B (%) |
| --- | --- |
| 0.00 | 2 |
| 25.00 | 40 |
| 25.10 | 100 |
| 26.90 | 100 |
| 27.00 | 2 |
| 36.00 | 2 |

Ion Chromatography (IC)
  Column: Dionex IonPac AS14A-5Pm, 3×150 mm
  Guard Column: Dionex IonPac AG14A-5Pm, 3×30 mm
  Mobile Phase: 8 mM $Na_2CO_3$/1 mM $NaHCO_3$
  Diluent: Purified water
  Flow Rate: 0.5 mL/min
  Runtime: 15 minutes
  Detector suppression: 50 mA, water regenerant as required
  Column Temperature: 30° C.
  Injection Volume: 25 μL (sample volume may be adjusted as required)
  Sample Concentration: 0.4 mg/mL in water Stability Testing
  Approximately 30 mg of the tosylate and fumarate salts were subjected to 7-day stability testing under the following conditions:
  40° C./75% RH
  80° C.
  Ambient temperature and light
  After 7 days under the stated conditions, XRPD and HPLC analysis was carried out on the resultant solid material.

Salt Disproportionation Studies
  Salt disproportionation studies were carried out on the tosylate and fumarate salts using the following procedure:
  Approximately 30 mg of salt was slurried in 300 μL of deionized water.
  Slurries were stirred at 20° C. for 30 min then measured pH before leaving to stir overnight.
  After stirring slurries at 20° C. for 20 h, pH was re-measured.
  Solid material isolated by centrifugation and analyzed by XRPD.

Stability Testing
  Approximately 30 mg of the tosylate and fumarate salts were subjected to 7-day stability testing under the following conditions:
  40° C./75% RH
  80° C.
  Ambient temperature and light
  After 7 days under the stated conditions, XRPD and HPLC analysis was carried out on the resultant solid material.

Hydration Studies
  Hydration studies were carried out on the tosylate and fumarate salts using the following procedure:
  Approximately 15-40 mg of salt was slurried in 200-500 μL of IPA/water, adding the solvent in 100 μL aliquots until a mobile slurry was achieved.
  3 different water activities (aw), determined using the Wilson equation, were used: 0.368 (0.2% water), 0.608 (7.3% water) and 0.911 (67.9% water). IPA was dried over 3A molecular sieves before use.
  Slurries were stirred at 20° C. for 25 h then solid material was isolated by centrifugation and analyzed by XRPD.

TABLE A

Experimental Details for Hydration Studies

| Salt | $a_w$ | Mass of Salt (mg) | Solvent Volume (μL) |
| --- | --- | --- | --- |
| Tosylate | 0.368 | 25 | 500 |
|  | 0.608 | 25 | 500 |
|  | 0.911 | 40 | 200 |
| Fumarate | 0.368 | 15 | 400 |
|  | 0.608 | 25 | 400 |
|  | 0.911 | 41 | 500 |

Thermodynamic Solubility Studies
  Thermodynamic solubility studies at 3 different pH values were carried out on the tosylate and fumarate salts using the following procedure:
  Approximately 30 mg of salt was slurried in the appropriate buffer solution, adding the solvent in 100 μL aliquots until a mobile slurry was achieved.
  3 different buffers prepared: pH 1.2, pH 4.5 and pH 6.8.
  Stirred at 20° C. then checked pH and adjusted if necessary.
  Stirred at 20° C. for 1.5 h then added more solid, if required, to create slurries. pH checked again and adjusted if necessary.
  Stirred at 20° C. for 22 h then checked pH and readjusted to required values and left for a further 2 h so that reactions stirred at 20° C. for 24 h total.
  Solid material isolated by centrifugation and analyzed by XRPD.
  Solutions analyzed by HPLC for concentration.

pH 1.2 Buffer Preparation:
  25 mL of 0.2 M potassium chloride solution and 42.50 mL of 0.2 M hydrochloric acid solution were diluted to 100 mL using deionized water. The pH was adjusted as required, using either potassium chloride or hydrochloric acid solution.

pH 4.5 Buffer Preparation:
  25 mL of 0.2 M potassium hydrogen phthalate solution and 2.50 mL of 0.2 M sodium hydroxide solution were diluted to 100 mL using deionized water. The pH was adjusted as required, using either potassium hydrogen phthalate or sodium hydroxide solution.

pH 6.8 Buffer Preparation:
  25 mL of 0.2 M potassium phosphate monobasic solution and 11.20 mL of 0.2 M sodium hydroxide solution were diluted to 100 mL using deionized water. The pH was adjusted as required, using either potassium phosphate monobasic or sodium hydroxide solution.

Example 1. Primary Salt Screen

Six solvent systems were selected for the primary salt screen: methanol, 2-propanol, acetone:water (90:10 v/v), dichloromethane, anisole and acetonitrile:ethylene glycol (90:10 v/v). Based on the calculated (and measured) pKa values for the received material, 24 counterions were selected for the primary salt screen (Table B), to be carried out alongside 6 blank experiments using the received acetate salt.

TABLE B

Selected Counterions for Primary Salt Screen

| | | | pKa | | | | |
|---|---|---|---|---|---|---|---|
| No. | Acid | Class | 1 | 2 | 3 | LogP | MW |
| 1 | Hydrochloric acid | 1 | −6.10 | | | | 36.46 |
| 2 | Sulfuric | 1 | −3.00 | 1.92 | | −1.03 | 98.08 |
| 3 | Cholesteryl sulfate (sodium | | −3.00 | | | 4.45 | 466.72 |
| 4 | p-Toluenesulfonic acid | 2 | −1.34 | | | 0.93 | 190.22 |
| 5 | Methanesulfonic acid | 2 | −1.20 | | | −1.89 | 96.10 |
| 6 | Naphthalene-2-sulfonic acid | | | | | | |
| 7 | Benzenesulfonic acid | 2 | 0.70 | | | 0.47 | 158.18 |
| 8 | Oxalic | 2 | 1.27 | 4.27 | | −1.19 | 90.04 |
| 9 | Maleic | 1 | 1.92 | 6.23 | | −0.01 | 116.07 |
| 10 | Phosphoric acid | 1 | 1.96 | 7.12 | 12.32 | −2.15 | 98.00 |
| 11 | Ethanesulfonic acid | 2 | 2.05 | | | −1.36 | 110.13 |
| 12 | L-Glutamic acid | 1 | 2.19 | 4.25 | | −1.43 | 147.13 |
| 13 | 1-Hydroxy-2-naphthoic | 2 | 2.70 | 13.50 | | 3.29 | 188.17 |
| 14 | L-Tartaric acid | 1 | 3.02 | 4.36 | | −1.43 | 150.09 |
| 15 | Fumaric | 1 | 3.03 | 4.38 | | −0.01 | 116.07 |

TABLE B-continued

Selected Counterions for Primary Salt Screen

| | | | pKa | | | | |
|---|---|---|---|---|---|---|---|
| No. | Acid | Class | 1 | 2 | 3 | LogP | MW |
| 16 | Citric | 1 | 3.13 | 4.76 | 6.40 | −1.72 | 192.12 |
| 17 | D-Glucuronic acid | 1 | 3.18 | | | −1.49 | 194.14 |
| 18 | L-Malic | 1 | 3.46 | 5.10 | | −1.26 | 134.09 |
| 19 | Hippuric acid | 1 | 3.55 | | | 0.31 | 179.17 |
| 20 | Benzoic | 2 | 4.19 | | | 1.89 | 122.12 |
| 21 | Succinic acid | 1 | 4.21 | 5.64 | | −0.59 | 118.09 |
| 22 | Adipic | 1 | 4.44 | 5.44 | | 0.08 | 146.14 |
| 23 | Deoxycholic acid | | 4.76 | | | 3.8 | 392.57 |
| 24 | Lauric | 1 | 4.90 | | | 4.6 | 200.32 |

The primary salt screen was carried out on 35 mg scale in a glovebag under nitrogen using >3 equivalents of the counterions in the appropriate solvent. The contents of the vials were temperature cycled from 30 to 5° C. Any solids were isolated and analyzed by XRPD.

Approximately 35 mg of received material was weighed into each vial, in a glovebag under nitrogen. If amorphous material or counterion isolated, material was returned to vial and solids re-dissolved through addition of an appropriate solvent. Further temperature cycling was then employed, followed by anti-solvent addition and evaporation if required. Solids, if present, were isolated by centrifugation and analyzed by XRPD. Crystalline material was further analyzed by PLM, TG/DTA and subjected to stability testing for 72 hours at 40° C./75% RH, with post-stability XRPD and HPLC analysis.

TABLE C

Summary of Crystalline Hits from Primary Salt Screen

| Counterion/Solvent | Crystallinity by XRPD | Morphology by PLM | Same XRPD, post-stability | Purity by HPLC |
|---|---|---|---|---|
| p-TsOH, MeOH | P1, moderate | unclear | yes | 80.6 |
| p-TsOH, IPA | P2, good | needles | no, P1 | 98.9 |
| p-TsOH, MeCN/EG | P1, good | plates/rods | nd | nd |
| MSA, MeOH | P1, good | unclear | new form | 91.1 |
| MSA, IPA | P1, good | unclear | new form | 97.2 |
| MSA, acetone/water | P2, good | unclear | new form | 99.2 |
| MSA, DCM | P1, good | unclear | nd | nd |
| MSA, anisole | P1, good | unclear | nd | nd |
| Oxalic acid, MeOH | P1, moderate | unclear | nd | nd |
| Oxalic acid, IPA | P1, good | needles | amorphous | 99.0 |
| Oxalic acid, acetone/water | P2, good | unclear | amorphous | 97.1 |
| ESA, IPA | P1, good | unclear | new form | 95.8 |
| ESA, DCM | P2, moderate | unclear | nd | nd |
| ESA, anisole | P2, good | unclear | new form | 90.5 |
| Fumaric acid, IPA | P1, good | rods/needles | yes (less crystalline) | 99.8 |
| Fumaric acid, acetone/water | P2, moderate | unclear | nd | nd |
| Benzoic acid, IPA | P1, moderate | unclear | nd | nd |
| Succinic acid, acetone/water | P1, moderate | unclear | amorphous | 98.0 |
| Cholesteryl sulfate, MeOH | P1, moderate | unclear | poorly crystalline | nd (insoluble) |
| Cholesteryl sulfate, MeCN/EG | P2, moderate | unclear | new form | nd (insoluble) |

P1 = Pattern 1; P2 = Pattern 2

Example 2. General Procedure for the Preparation of Crystalline Forms

MTP-131 was charged to a vial in a glovebag under nitrogen and slurried in the appropriate solvent at 20° C. A solution of the counterion was charged was added dropwise to the vial containing the material (homogeneity solvent dependent). The slurry was stirred at 27±7° C. to achieve dissolution. In some cases, a co-solvent such as water was added incremental to achieve dissolution. The solution was temperature cycled between 40 and 0° C. The material was isolated through filtration using a Buchner funnel, rinsed with the appropriate solvent and then dried under vacuum at ambient temperature for 58 h before characterization. A portion of the material was further dried at 40° C. for ca. 48 h and then analyzed by TG/DTA.

Example 3. Small-Scale Tosylate Salt Synthesis

The tosylate salt (500 mg scale) was prepared using IPA with water as the co-solvent to achieve dissolution.
Powder X-ray diffraction pattern and XRPD peaks with relative intensities of the crystalline tosylate form thus prepared are shown in FIG. 9 and Table 3, respectively.

Example 4. Further Small-Scale Fumarate Salt Synthesis

The fumarate salt was prepared on 35 mg scale.
Different ratios of fumaric acid were used as indicated in Table D.
For experiments yielding solid material were isolated by centrifugation and analyzed by XRPD.

TABLE D

Experimental Details for further Small-Scale Fumarate Reactions.

| | Initial Solvent | Eq. Fumaric Acid | Additional Solvent (Volume) | Temperature Cycling (h) |
|---|---|---|---|---|
| 1 | IPA | 3.1 | Water, 100 µL | 92 |
| 2 | IPA:water (7.55:1 v/v) | 3.1 | IPA:water (7.55:1 v/v), 250 µL | 92 |
| 3 | IPA | 3.1 | Water, 300 pL; IPA, 150 µL | 92 |
| 4 | IPA | 4.6 | Water, 250 µL | 16 |
| 5 | Acetone | 4.6 | Water, 250 µL | 16 |
| 6 | Acetonitrile | 4.6 | Water, 250 µL | 16 |
| 7 | 1-Butanol | 4.6 | Water, 400 µL; 1-butanol, 200 µL; IPA, 450 µL | 30 |
| 8 | 1-Propanol | 4.6 | Water, 250 µL | 16 |

After stirring at 20° C. for 2.5 h, slurries were fully dissolved through the addition of water, with further organic solvent added if separation occurred (Reactions 5 and 7). After temperature cycling overnight, solid material was isolated from Reactions 4-6 and 8. Pattern 3 was isolated from Reactions 1-4 and 5, with new patterns isolated from Reactions 6 and 8. After adding additional IPA to Reaction 7 and temperature cycling overnight, solid material corresponding to another new pattern was isolated.

Example 5. Preparation of Fumarate Pattern 3

The fumarate salt (500 mg scale) was prepared using IPA with water as the co-solvent to achieve dissolution.
After 1 h stirring at ambient temperature, mixing was poor as the material had precipitated to give a thick slurry. Aliquots of IPA were added until solvent composition was IPA-water (~4:1).

Stirred at ambient temperature (ca. 23° C.) for 17 h, then isolated through filtration using a Buchner funnel, rinsed with IPA and then dried under vacuum at ambient temperature for 22.5 h before characterization.

Example 6. Tosylate Salt

The following observations and results were made during characterization of the tosylate salt:
Tosylate Pattern 1 was crystalline by XRPD analysis, with no clearly defined morphology observed in the PLM analysis of the sample from methanol. Both plates and rods were observed in the PLM analysis of the sample from acetonitrile:ethylene glycol (90:10 v/v) and all samples were birefringent.
Pattern 1 is potentially a hydrated form, with loss of ca. 1.7% in the TGA from the outset to ca. 90° C. likely due to loss of water. This was followed by a further weight loss of 0.3% (90-200° C.) before the onset of decomposition.
Pattern 1 showed a small endothermic event in the DTA at ca. 70.5° C., associated with the initial weight loss. A further endotherm was observed at onset ca. 203.8° C. (peak at ca. 214.8° C.).
Tosylate Pattern 2 was crystalline by XRPD analysis, with birefringence and a needle-like morphology observed in the PLM analysis of the sample from IPA.
Pattern 2 is also potentially a hydrated form, with loss of ca. 1.2% in the TGA from the outset to ca. 80° C. likely due to loss of water. This is followed by a further weight loss of 0.1% (80-190° C.) before the onset of decomposition.
Pattern 2 showed an endothermic event in the DTA at onset ca. 217.1° C. (peak at ca. 226.8° C.).
XRPD analysis of samples after stability testing at 40° C./75% RH indicated that Pattern 1 (from methanol) improved in crystallinity after stability, while Pattern 2 (from IPA) converted to Pattern 1.
HPLC analysis of samples after stability testing at 40° C./75% RH indicated that Pattern 1
(from methanol) had a purity of 80.6%, while Pattern 1 (from IPA) had a purity of 98.9%.

Example 7. Mesylate Salt

The following observations and results were made during characterization of the mesylate salt:
Mesylate Pattern 1 was crystalline by XRPD analysis and birefringent by PLM analysis, with no clearly defined morphology observed in the samples from methanol, IPA, DCM or anisole. The particles were observed to be very small.

Pattern 1 is potentially a hydrate or solvate, with loss of ca. 3.8% in the TGA from the outset to ca. 110° C. This is followed by a further weight loss of 1.0% (110-220° C.) before the onset of decomposition. Further confirmation as to the nature of this solid form is required.

Pattern 1 showed a small endothermic event in the DTA at ca. 84.8° C., associated with the initial solvent loss. A further endotherm was observed at onset ca. 186.4° C. (peak at ca. 196.4° C.).

Further TG/DT analysis of Pattern 1 was carried out on samples isolated from IPA and DCM. Pattern 1 from IPA is potentially a hydrate or solvate, with loss of ca. 1.3% in the TGA from the outset to ca. 100° C. This is followed by a further weight loss of 2.0% (100-220° C.) before the onset of decomposition. Pattern 1 from IPA showed small endothermic events in the DTA at ca. 77.5° C. and ca. 164.9° C., associated with these solvent/water losses. A further endotherm was observed at onset ca. 191.1° C. (peak at ca. 194.9° C.).

Pattern 1 from DCM is potentially a hydrate or solvate, with loss of ca. 4.0% in the TGA from the outset to ca. 160° C. This is followed by a further weight loss of 1.0% (160-220° C.) before the onset of decomposition. Pattern 1 from DCM showed a small endothermic event in the DTA at ca. 178.0° C., associated with solvent loss. A further endotherm was observed at onset ca. 188.4° C. (peak at ca. 196.1° C.).

Mesylate Pattern 2 was crystalline by XRPD analysis and birefringent by PLM analysis, with no clearly defined morphology observed in the sample from acetone:water (90:10 v/v).

Pattern 2 is potentially a solvate/hydrate, with loss of ca. 5.3% in the TGA from the outset to ca. 120° C. This is followed by a further weight loss of 2.1% (120-175° C.) before the onset of decomposition. Further confirmation as to the nature of this solid form is required.

Pattern 2 showed a small endothermic event in the DTA at 62.1° C. and a further endothermic event at onset ca. 129.2° C. (peak at ca. 136.6° C.).

XRPD analysis of samples after stability testing at 40° C./75% RH indicated that both Pattern 1 (from methanol and IPA) and Pattern 2 (from acetone:water 90:10 v/v) lost crystallinity and converted to a different pattern after stability. A broad, poorly crystalline pattern was obtained in each case.

HPLC analysis of samples after stability testing at 40° C./75% RH indicated that the sample from methanol had a purity of 91.1%, the sample from IPA had a purity of 97.2% and the sample from acetone:water 90:10 v/v had a purity of 99.2%.

Example 8. Oxalate Salt

The following observations and results were made during characterization of the oxalate salt:

Oxalate Pattern 1 was crystalline by XRPD analysis and birefringent by PLM analysis. No clearly defined morphology was observed in the sample obtained from methanol, but needles were observed from IPA.

Pattern 1 is potentially a solvate/hydrate, with loss of ca. 7.7% in the TGA from the outset to ca. 90° C., followed by a further weight loss of 6.6% (90-160° C.) before the onset of decomposition.

Pattern 1 showed endothermic events in the DTA at onset ca. 53.0° C. (peak at ca. 69.5° C.), at onset ca. 134.3° C. (peak at ca. 137.6° C.) and at onset ca. 168.0° C. (peak at ca. 178.5° C.).

Oxalate Pattern 2 was crystalline by XRPD analysis and birefringent by PLM analysis, with no clearly defined morphology observed in the sample obtained from acetone:water (90:10 v/v).

Pattern 2 is potentially a solvate/hydrate, with loss of ca. 7.0% in the TGA from the outset to ca. 140° C. Further weight loss is likely associated with decomposition.

Pattern 2 showed a broad endothermic event in the DTA at onset ca. 185.4° C. (peak at ca. 203.5° C.), likely associated with decomposition.

XRPD analysis of samples after stability testing at 40° C./75% RH indicated that both Pattern 1 (from IPA) and Pattern 2 (from acetone:water (90:10 v/v)) lost all crystallinity and converted to amorphous material after stability HPLC analysis of samples after stability testing at 40° C./75% RH indicated that the sample from IPA had a purity of 99.0% and the sample from acetone:water (90:10 v/v) had a purity of 97.1%.

Example 9. Esylate Salt

The following observations and results were made during characterization of the esylate salt:

Esylate Pattern 1 was crystalline by XRPD analysis and birefringent by PLM analysis. No clearly defined morphology was observed in the sample from IPA; particles were small and there was some agglomeration observed.

Pattern 1 is potentially a hydrate or anhydrous form, with loss of ca. 3.0% in the TGA from the outset to ca. 90° C., followed by a further weight loss of 0.4% (90-200° C.) before the onset of decomposition. Further analysis would be required in order to establish the exact nature of the form.

Pattern 1 showed endothermic events in the DTA at onset ca. 78.6° C. (peak at ca. 80.5° C.), and at onset ca. 158.6° C. (peak at ca. 169.7° C.).

Esylate Pattern 2 was crystalline by XRPD analysis and birefringent by PLM analysis, with no clearly defined morphology observed in the samples obtained from dichloromethane or anisole.

Pattern 2 is potentially a hydrate or anhydrous form, with loss of ca. 3.4% in the TGA from the outset to ca. 90° C., followed by further weight losses of 0.2% (90-145° C.) and 0.6% (145-210° C.) before the onset of decomposition. Further analysis would be required in order to establish the exact nature of the form.

Pattern 2 showed a broad endothermic event in the DTA at onset ca. 43.0° C. (peak at ca. 61.6° C.) and further, overlapped endothermic events at onset ca. 154.3° C. (peaks at ca. 168.8° C. and at 181.8° C.).

XRPD analysis of samples after stability testing at 40° C./75% RH indicated that both Pattern 1 (from IPA) and Pattern 2 (from anisole) converted to a new pattern after stability. The sample from IPA lost crystallinity in this conversion, while the sample from anisole improved in crystallinity.

HPLC analysis of samples after stability testing at 40° C./75% RH indicated that the sample from IPA had a purity of 95.8% and the sample from anisole had a purity of 90.5%.

Example 10. Fumarate Salt

The following observations and results were made during characterization of the fumarate salt:

Fumarate Pattern 1 was crystalline by XRPD analysis and birefringent by PLM analysis. Both rod-like and needle-like morphology was observed in the sample from IPA.

Pattern 1 is potentially a solvate/hydrate, with loss of ca. 4.5% in the TGA from the outset to ca. 100° C. This is followed by a further weight loss of 2.0% (100-160° C.) before the onset of decomposition.

Pattern 1 showed endothermic events in the DTA at onset ca. 132.6° C. (peak at ca. 140.8° C.), and at onset ca. 183.1° C. (peak at ca. 198.5° C.).

Fumarate Pattern 2 was crystalline by XRPD analysis and birefringent by PLM analysis, with no clearly defined morphology observed in the sample obtained from acetone:water (90:10 v/v).

Pattern 2 is potentially a solvate/hydrate, with loss of ca. 2.6% in the TGA from the outset to ca. 50° C. This is followed by a further weight loss of 5.1% (50-150° C.) before the onset of decomposition.

Pattern 2 showed endothermic events in the DTA at onset ca. 137.3° C. (peak at ca. 147.1° C.) and at onset ca. 188.2° C. (peak at ca. 207.8° C.).

XRPD analysis of the sample after stability testing at 40° C./75% RH indicated that Pattern 1 (from IPA) lost some crystallinity but retained the same form after stability. Not enough material remained of Pattern 2 to carry out stability testing.

HPLC analysis of the sample after stability testing at 40° C./75% RH indicated that the sample from IPA had a purity of 99.8%.

Example 11. Benzoate Salt

The following observations and results were made during characterization of the benzoate salt:

Benzoate Pattern 1 was crystalline by XRPD analysis and birefringent by PLM analysis, with no clearly defined morphology observed in the sample from IPA.

Pattern 1 is potentially a solvate/hydrate, with loss of ca. 5.8% in the TGA from the outset to ca. 130° C. This is followed by further weight losses of 2.4% (130-180° C.) and 2.7% (180-240° C.) before the onset of decomposition.

Pattern 1 showed no events in the DTA until an endothermic event at ca. 245.5° C., likely associated with decomposition.

Not enough material remained of Pattern 1 to carry out stability testing.

Example 12. Succinate Salt

The following observations and results were made during characterization of the succinate salt:

Succinate Pattern 1 was crystalline by XRPD analysis and birefringent by PLM analysis, with no clearly defined morphology observed in the sample from acetone:water (90:10 v/v).

Pattern 1 is potentially a solvate/hydrate, with loss of ca. 8.3% in the TGA from the outset to ca. 145° C. This is followed by a further weight loss of 7.9% (145-240° C.), associated with the onset of decomposition.

Pattern 1 showed an endothermic event in the DTA at onset ca. 64.8° C. (peak at ca. 75.0° C.), with a small exothermic event at ca. 140.3° C. A further endothermic event at onset ca. 178.6° C. (peak at ca. 199.7° C.) is associated with the onset of decomposition.

XRPD analysis of the sample after stability testing at 40° C./75% RH indicated that Pattern 1 (from acetone:water (90:10 v/v)) lost crystallinity and became amorphous after stability.

HPLC analysis of the sample after stability testing at 40° C./75% RH indicated that the sample from acetone:water (90:10 v/v) had a purity of 98.0%.

Example 13. Cholesteryl Sulfate Salt

The following observations and results were made during characterization of the cholesteryl sulfate salt:

Cholesteryl sulfate Pattern 1 was crystalline by XRPD analysis and birefringent by PLM analysis with no clearly defined morphology observed in the sample from methanol.

Pattern 1 is potentially a hydrate or anhydrous form, with loss of ca. 2.9% in the TGA from the outset to ca. 200° C. Further weight loss is associated with the onset of decomposition. Further analysis would be required in order to establish the exact nature of the form.

Pattern 1 showed a small endothermic event in the DTA at 105.1° C. and a further endothermic event at onset ca. 204.0° C. (peak at ca. 215.3° C.).

Cholesteryl sulfate Pattern 2 was crystalline by XRPD analysis and birefringent by PLM analysis, with no clearly defined morphology observed in the sample obtained from acetonitrile:ethylene glycol (90:10 v/v).

Pattern 2 is potentially a solvate/hydrate, with loss of ca. 1.5% in the TGA from the outset to ca. 90° C. followed by a further weight loss of 8.1% (90-150° C.) before the onset of decomposition.

Pattern 2 showed endothermic events in the DTA at onset ca. 104.5° C. (peak at ca. 118.4° C.) and at ca. 205.1° C.

XRPD analysis of the sample after stability testing at 40° C./75% RH indicated that Pattern 1 (from methanol) lost crystallinity after stability, with only traces of the input pattern visible in the diffractogram. Pattern 2 (from acetonitrile:ethylene glycol (90:10 v/v)) converted to a different pattern after stability.

HPLC analysis of the samples after stability testing at 40° C./75% RH was unsuccessful due to the low solubility of the samples, even when DMSO was used as the diluent.

Example 14. Preparation of Tosylate Pattern 1

The following observations and results were obtained during preparation and characterization of the tosylate salt in the secondary salt screen:

IPA was used as the reaction solvent in the secondary salt screen, with the addition of water to favor conversion of Pattern 2 to Pattern 1.

After dissolving the slurry with water, a large amount of precipitate formed after stirring for 2 h at 25° C. XRPD analysis of a sample of this solid indicated that it was the desired Pattern 1 material.

XRPD analysis of a sample of the solid after diluting with IPA and temperature cycling for a further 64 h indicated that it was still the desired Pattern 1 material.

After isolation and drying at ambient temperature for 58 h, 0.64 g of material was obtained (88% yield, based on 3 eq. of tosylate).

The dried material was observed to remain Pattern 1 by XRPD analysis and was slightly birefringent by PLM analysis, with a rod-like morphology.

TG analysis after 24 h drying at ambient temperature showed a weight loss of ca. 1.1% from the outset up to ca. 90° C. No further weight loss was observed prior to the onset of decomposition.

DTA after 24 h drying at ambient temperature showed endothermic events at ca. 60.4° C. and at ca. 230.7° C., likely due to melting of the material.

TG analysis after 42 h drying at ambient temperature showed a weight loss of ca. 1.4% from the outset up to ca. 90° C. No further weight loss was observed prior to the onset of decomposition. (Note: 1 molar equivalent of water would correspond to ca. 1.55 wt %)

DTA after 42 h drying at ambient temperature showed an endothermic event at ca. 66.8° C. and at onset ca. 222.9° C. (peak at 231.1° C.), likely due to melting of the material.

TG analysis after 58 h drying at ambient temperature showed a weight loss of ca. 1.3% from the outset up to ca. 90° C. No further weight loss was observed prior to the onset of decomposition.

DTA after 58 h drying at ambient temperature showed an endothermic event at ca. 65.4° C. and at onset ca. 224.8° C. (peak at 230.2° C.), likely due to melting of the material.

TG analysis after 58 h drying at ambient temperature and 48 h drying at 40° C. showed a weight loss of ca. 1.3% from the outset up to ca. 90° C. No further weight loss was observed prior to the onset of decomposition.

DTA after 58 h drying at ambient temperature and 48 h drying at 40° C. showed an endothermic event at ca. 64.7° C. and at onset ca. 223.7° C. (peak at 230.5° C.), likely due to melting of the material.

DSC showed an endothermic event at onset ca. 108.3° C. (peak at ca. 138.6° C.), likely due to water loss, and a further endothermic event at onset ca. 224.3° C. (peak at ca. 232.6° C.), likely due to melting of the material.

The 1H NMR spectrum of the received material was consistent with a tosylate salt and suggested ca. 3 eq. of tosylate present.

DVS analysis of the tosylate salt showed it to be slightly hygroscopic, with a change in mass of ca. 1.3% between 20-90% RH.

Post-DVS XRPD analysis of the tosylate salt showed it remained Pattern 1 after the DVS experiment. The physical appearance of the post-DVS material was unchanged.

KF analysis of the tosylate salt gave a water content of ca. 2.1% (average of 3 samples run).

By HPLC analysis, the purity of the tosylate salt was 99.8%.

Example 15. Preparation of Fumarate Pattern 3

The following observations and results were obtained during preparation and characterization of the fumarate salt, Pattern 3 in the secondary salt screen:

Using Procedure 2, a large amount of precipitate formed after dissolving the slurry with water and temperature cycling for 14 h. XRPD analysis of a sample of this solid indicated that it was mostly amorphous.

XRPD analysis of a sample after recrystallizing using water, seeding with Pattern 1 material and temperature cycling for a further 19 h indicated that it was poorly crystalline Pattern 3.

XRPD analysis of samples after recrystallizing using water/IPA and stirring at ambient temperature for ca. 24 h indicated crystalline Pattern 3.

After isolation and drying at ambient temperature for 19 h, 0.37 g of material was obtained (59% yield, based on 3 eq. of fumarate).

The dried material was observed to have a different pattern to the isolated material by XRPD analysis, likely due to loss of solvent/water upon drying. This pattern was designated Pattern 4.

The fumarate salt was birefringent by PLM analysis, with a needle-like morphology.

TG analysis after 19 h drying showed a weight loss of ca. 5.2% from the outset up to ca. 100° C., followed by weight losses of ca. 0.5% between 100-140° C. and ca. 2.6% between 140-160° C., prior to the onset of decomposition. (Note: 3 molar equivalents of water would correspond to ca. 5.78 wt %).

DTA showed an endothermic event at ca. 63.8° C. and at onset ca. 147.3° C. (peak at 151.2° C.), likely due to loss of water.

DSC showed several overlapping endotherms at onset ca. 64.7° C. (peaks at ca. 81.3° C., 96.3° C. and 117.6° C.). A further endotherm was observed at onset ca. 144.7° C. (peak at ca. 153.4° C.).

The 1H NMR spectrum of the isolated material was consistent with a fumarate salt and suggested ca. 2.2 eq. of fumarate present. IPA was also visible in the spectrum.

DVS analysis of the fumarate salt showed it to be hygroscopic, with a change in mass of ca. 11.5% between 20-90% RH.

Post-DVS XRPD analysis of the fumarate salt showed it remained Pattern 4 after the DVS experiment, although loss of crystallinity was observed. The physical appearance of the post-DVS material was unchanged.

KF analysis of the fumarate salt gave a water content of ca. 7.5% (average of 3 samples run). As the TGA shows mass loss of ca. 8.3% before decomposition this loss is likely mostly water, with some IPA also present.

By HPLC analysis, the purity of the fumarate salt was 99.9%.

Procedure 3:

Using Procedure 3, a large amount of precipitate formed after dissolving the slurry with water and stirring at ambient temperature (ca. 23° C.) for 1 h. XRPD analysis of a sample of this solid indicated that it was poorly crystalline Pattern 3.

After recrystallizing using water/IPA and stirring at ambient temperature (ca. 23° C.) for 17 h, XRPD analysis of a sample indicated that it was crystalline Pattern 3.

After isolation and drying at ambient temperature for 22.5 h, 0.26 g of material was obtained (42% yield, based on 3 eq. of fumarate).

XRPD analysis of the dried material indicated that it was Pattern 4. This batch of material was used in the solubility and hydration studies.

Example 16. Stability Testing

The scaled-up tosylate and fumarate salts were subjected to 7-day stability testing at 40° C./75% RH, 80° C. and ambient temperature and light. The following observations and results were obtained during these stability tests:

Post-stability XRPD analysis of the tosylate samples indicated that input Pattern 1 was unchanged after stability testing.

Post-stability HPLC analysis of the tosylate samples indicated that there was a slight decrease (<0.5%) in purity after stability testing at 80° C. and ambient light/temperature. A decrease in purity of ca. 1.3% after stability testing at 40° C./75% RH was observed.

Post-stability XRPD analysis of the fumarate samples indicated that input Pattern 4 was unchanged at lower temperatures, with no significant crystallinity loss at 40° C./75% RH, or under ambient conditions. At 80° C., a loss of crystallinity was observed.

Post-stability HPLC analysis of the fumarate samples indicated that there was a slight decrease (<0.5%) in purity after stability testing at ambient light/temperature and a decrease in purity of ca. 2.4% after stability testing at 40° C./75% RH. However, a significant decrease in purity of ca. 17% was observed after stability testing at 80° C.

TABLE E

7 Day Stability Data for Tosylate and Fumarate Salts

| Salt | Stability Conditions | Purity by HPLC (%) |
| --- | --- | --- |
| Tosylate (99.8%) | 40° C./75% RH | 98.5 |
| | 80° C. | 99.4 |
| | Ambient temperature and light | 99.6 |
| Fumarate (99.9%) | 40° C./75% RH | 97.5 |
| | 80° C. | 83.0 |
| | Ambient temperature and light | 99.6 |

Example 17. Salt Disproportionation Studies

The scaled-up tosylate and fumarate salts were subjected to salt disproportionation studies at ambient temperature. The following observations and results were obtained during these disproportionation studies:

After stirring the tosylate salt at 20° C. in deionized water for 30 min, pH=2.58. After 20 h at 20° C., pH was re-measured and was found to be 2.53.

XRPD analysis of the post-slurry tosylate material indicated that there was no change to the input Pattern 1 material.

After stirring the fumarate salt at 20° C. in deionized water for 30 min, pH=3.50. After 20 h at 20° C., pH was re-measured and was found to be 3.48.

XRPD analysis of the post-slurry fumarate material indicated that the input Pattern 4 material had changed to a new pattern (designated Pattern 5), suggesting further hydrate formation.

Example 18. Hydration Studies

Hydration studies in IPA at 3 different water activities (aw=0.368, 0.608 and 0.911) were carried out using the scaled-up tosylate and fumarate salts at ambient temperature. The following observations and results were obtained during these hydration studies:

After stirring the tosylate salt at 20° C. for 25 h in each of the IPA/water mixtures prepared, XRPD analysis of the isolated solids indicated that input Pattern 1 was unchanged after hydration studies.

After stirring the fumarate salt at 20° C. for 24 h in each of the IPA/water mixtures prepared, XRPD analysis of the isolated solids indicated that input Pattern 4 had changed after the hydration studies. Pattern 3 was obtained at lower aw values (aw=0.368 and 0.608), while Pattern 5 was obtained at aw=0.911, suggesting further hydration occurred. The analysis was carried out on damp solids and it is likely that Pattern 3 would convert back to Pattern 4 after drying.

Example 19. Thermodynamic Solubility Studies

Thermodynamic solubility studies in buffers at 3 different pH values (pH=1.2, 4.5 and 6.8) were carried out using the scaled-up tosylate and fumarate salts at ambient temperature. The following observations and results were obtained during these thermodynamic solubility studies:

After creating slurries of the tosylate salt and stirring at 20° C. for ca. 15 min, pH values were checked and found to be 1.21, 4.23 and 6.55, respectively.

Adjusted tosylate slurries to pH 4.51 and 6.81, adding more tosylate salt to pH=4.5 reaction to saturate.

After stirring the tosylate salt at 20° C. for 22 h in each buffer solution, pH values checked again and found to be 1.22, 4.41 and 6.56, so adjusted final slurry to pH 6.76.

After stirring the tosylate salt at 20° C. for 24 h in each buffer solution, XRPD analysis of the isolated solids indicated that input Pattern 1 was unchanged after thermodynamic solubility studies. HPLC analysis of the solutions indicated that the solubility of the tosylate salt was relatively unchanged by pH, with each pH giving a concentration of ca. 25 mg/mL (see Table 10 for details).

After creating slurries of the fumarate salt and stirring at 20° C. for ca. 15 min, pH values were checked and found to be 3.36, 3.63 and 3.73, respectively.

Adjusted fumarate slurries to pH 1.26, 4.51 and 6.88, adding more fumarate salt to pH=4.5 and 6.8 reactions to saturate.

pH values for reactions which had more solid added were checked again and found to be 3.36 and 4.50, so pH was adjusted to 4.41 and 6.76. All material dissolved in pH 6.8 buffer solution, could not be saturated.

After stirring the fumarate salt at 20° C. for 22 h in each buffer solution, pH values checked again and found to be 1.48, 4.45 and 6.56, so adjusted first slurry to pH 1.17.

After stirring the fumarate salt at 20° C. for 24 h in each buffer solution, XRPD analysis of the isolated solids indicated that input Pattern 4 was changed by the thermodynamic solubility studies. pH 1.2 buffer solution resulted in isolation of fumaric acid only, while pH 4.5 buffer solution resulted in isolation of Pattern 5. No solid was isolated from pH 6.8 reaction.

HPLC analysis of the solutions indicated that the solubility of the fumarate salt increases as the pH increases, with solubility >173 mg/mL at pH 6.8.

TABLE F

Thermodynamic Solubility Data for Tosylate and Fumarate Salts

| Salt | Buffer Solution (pH) | Concentration by HPLC (mg/mL) | Solid Form |
| --- | --- | --- | --- |
| Tosylate | 1.2 | 23.8 | Pattern 1 |
| | 4.5 | 25.8 | Pattern 1 |
| | 6.8 | 24.3 | Pattern 1 |
| Fumarate | 1.2 | 35.1 | Fumaric acid |
| | 4.5 | 123.1 | Pattern 5 |

Example 20. Cholesteryl Sulfate Pattern 1 (Methanol)—XRPD Peak List

TABLE 1

| Pos. [°2θ] | Height [cts] | Rel. Int. |
|---|---|---|
| 4.9500 | 513.95 | 92.32 |
| 5.7914 | 307.76 | 55.28 |
| 8.5140 | 76.04 | 13.66 |
| 9.8145 | 76.19 | 13.68 |
| 10.5199 | 86.72 | 15.58 |
| 11.9028 | 157.46 | 28.28 |
| 12.3400 | 147.07 | 26.42 |
| 12.6450 | 148.79 | 26.73 |
| 13.1574 | 136.33 | 24.49 |
| 16.0665 | 556.71 | 100.00 |
| 16.7594 | 510.78 | 91.75 |
| 17.0428 | 268.80 | 48.28 |
| 19.0804 | 122.95 | 22.08 |
| 20.3368 | 52.81 | 9.49 |
| 20.7068 | 54.47 | 9.78 |
| 21.7397 | 56.11 | 10.08 |

Example 21. Cholesteryl Sulfate Pattern 2 (Acetonitrile:Ethylene Glycol (90:10 v/v))—XRPD Peak List

TABLE 2

| Pos. [°2θ] | Height [cts] | Rel. Int. |
|---|---|---|
| 7.4205 | 379.10 | 50.08 |
| 9.8832 | 111.44 | 14.72 |
| 12.4010 | 227.72 | 30.08 |
| 13.0698 | 476.92 | 63.00 |
| 13.3833 | 205.77 | 27.18 |
| 14.4079 | 157.67 | 20.83 |
| 15.0973 | 135.35 | 17.88 |
| 15.5537 | 408.19 | 53.92 |
| 16.2771 | 756.98 | 100.00 |
| 16.8114 | 138.31 | 18.27 |
| 17.1732 | 106.30 | 14.04 |
| 17.4697 | 127.72 | 16.87 |
| 17.7008 | 344.28 | 45.48 |
| 19.4681 | 157.41 | 20.79 |
| 19.8491 | 436.46 | 57.66 |
| 22.8297 | 52.91 | 6.99 |
| 29.9651 | 45.41 | 6.00 |
| 32.5913 | 40.20 | 5.31 |

Example 22. Tosylate Pattern 1 (Acetonitrile:Ethyleneglycol (90:10 v/v)) XRPD Peak List

TABLE 3

| Pos. [°2θ] | Height [cts] | Rel. Int. |
|---|---|---|
| 6.3236 | 859.74 | 30.00 |
| 7.1904 | 530.19 | 18.50 |
| 9.0662 | 300.72 | 10.49 |
| 11.1993 | 316.77 | 11.05 |
| 11.6515 | 1518.36 | 52.99 |
| 11.8245 | 302.27 | 10.55 |
| 12.2481 | 1314.64 | 45.88 |
| 12.7291 | 509.38 | 17.78 |
| 12.9196 | 384.25 | 13.41 |
| 13.4259 | 1529.40 | 53.37 |
| 13.9356 | 307.63 | 10.74 |
| 14.0866 | 204.08 | 7.12 |

TABLE 3-continued

| Pos. [°2θ] | Height [cts] | Rel. Int. |
|---|---|---|
| 14.3102 | 270.76 | 9.45 |
| 14.7230 | 964.06 | 33.64 |
| 15.3518 | 1622.95 | 56.64 |
| 15.7767 | 500.48 | 17.47 |
| 16.0824 | 764.78 | 26.69 |
| 16.6610 | 687.30 | 23.99 |
| 16.9655 | 1363.75 | 47.59 |
| 17.4222 | 287.09 | 10.02 |
| 18.1176 | 865.70 | 30.21 |
| 18.9399 | 814.95 | 28.44 |
| 19.5396 | 283.99 | 9.91 |
| 19.7829 | 437.17 | 15.26 |
| 20.0556 | 296.99 | 10.36 |
| 20.2220 | 1287.25 | 44.92 |
| 21.6820 | 331.11 | 11.55 |
| 22.4522 | 2865.51 | 100.00 |
| 22.7058 | 1681.25 | 58.67 |
| 23.1326 | 1392.27 | 48.59 |
| 23.3451 | 475.86 | 16.61 |
| 23.7455 | 393.03 | 13.72 |
| 24.2204 | 316.19 | 11.03 |
| 24.5976 | 227.62 | 7.94 |
| 24.7839 | 256.18 | 8.94 |
| 25.6635 | 465.16 | 16.23 |
| 25.9383 | 704.34 | 24.58 |
| 27.0486 | 161.20 | 5.63 |
| 27.7138 | 218.23 | 7.62 |
| 28.2876 | 111.69 | 3.90 |
| 28.5866 | 260.93 | 9.11 |
| 28.8350 | 162.33 | 5.67 |
| 29.4111 | 188.53 | 6.58 |
| 29.7366 | 126.04 | 4.40 |
| 30.9351 | 44.63 | 1.56 |
| 31.2970 | 64.72 | 2.26 |
| 31.8586 | 56.60 | 1.98 |
| 34.1666 | 162.54 | 5.67 |
| 34.7854 | 69.07 | 2.41 |

Example 23. Tosylate Pattern 2 (2-propanol): XRPD Peak List

TABLE 4

| Pos. [°2θ] | Height [cts] | Rel. Int. |
|---|---|---|
| 6.5048 | 2925.31 | 67.47 |
| 7.0412 | 810.71 | 18.70 |
| 9.0165 | 650.57 | 15.01 |
| 11.5522 | 1124.90 | 25.95 |
| 11.8465 | 1593.96 | 36.76 |
| 12.0031 | 2406.52 | 55.51 |
| 12.4973 | 199.54 | 4.60 |
| 13.0115 | 2587.33 | 59.68 |
| 13.2622 | 2635.53 | 60.79 |
| 14.2951 | 1029.41 | 23.74 |
| 14.4394 | 956.83 | 22.07 |
| 14.6700 | 675.49 | 15.58 |
| 15.0149 | 1928.22 | 44.47 |
| 15.7182 | 3392.71 | 78.25 |
| 15.8732 | 1501.57 | 34.63 |
| 16.0677 | 933.19 | 21.52 |
| 17.3224 | 3615.64 | 83.40 |
| 17.6596 | 808.05 | 18.64 |
| 18.0742 | 225.60 | 5.20 |
| 19.3625 | 2665.67 | 61.48 |
| 19.5565 | 1674.71 | 38.63 |
| 19.6954 | 1034.21 | 23.85 |
| 20.0052 | 813.69 | 18.77 |
| 20.5458 | 2193.23 | 50.59 |
| 21.1722 | 788.75 | 18.19 |
| 21.9749 | 706.83 | 16.30 |
| 22.4132 | 2019.52 | 46.58 |
| 22.7633 | 1338.07 | 30.86 |
| 23.1157 | 4335.55 | 100.00 |

TABLE 4-continued

| Pos. [°2θ] | Height [cts] | Rel. Int. |
|---|---|---|
| 23.4474 | 490.16 | 11.31 |
| 23.7123 | 1792.36 | 41.34 |
| 24.2578 | 1012.24 | 23.35 |
| 24.5249 | 179.58 | 4.14 |
| 25.0281 | 521.70 | 12.03 |
| 25.2220 | 518.22 | 11.95 |
| 25.4124 | 735.02 | 16.95 |
| 26.1017 | 617.07 | 14.23 |
| 26.4002 | 530.84 | 12.24 |
| 26.6640 | 415.81 | 9.59 |
| 27.2584 | 204.55 | 4.72 |
| 27.6862 | 544.26 | 12.55 |
| 28.2087 | 368.13 | 8.49 |
| 28.4358 | 551.21 | 12.71 |
| 28.6690 | 403.71 | 9.31 |
| 29.0632 | 210.51 | 4.86 |
| 29.7900 | 405.63 | 9.36 |
| 30.1856 | 453.96 | 10.47 |
| 31.7342 | 69.62 | 1.61 |
| 32.5306 | 175.56 | 4.05 |
| 34.2641 | 117.22 | 2.70 |

Example 24. Mesylate Pattern 1 (Dichloromethane): XRPD Peak List

TABLE 5

| Pos. [°2θ] | Height [cts] | Rel. Int. |
|---|---|---|
| 5.6855 | 550.41 | 14.15 |
| 6.0206 | 2660.22 | 68.38 |
| 10.3924 | 3890.21 | 100.00 |
| 10.9552 | 1726.69 | 44.39 |
| 11.1560 | 953.53 | 24.51 |
| 11.6500 | 900.93 | 23.16 |
| 12.0524 | 1678.78 | 43.15 |
| 13.5772 | 776.50 | 19.96 |
| 13.8529 | 388.77 | 9.99 |
| 14.7106 | 678.23 | 17.43 |
| 14.9409 | 2928.38 | 75.28 |
| 15.2690 | 644.99 | 16.58 |
| 15.7091 | 1223.57 | 31.45 |
| 15.9920 | 1083.26 | 27.85 |
| 17.0746 | 155.12 | 3.99 |
| 17.5076 | 883.72 | 22.72 |
| 17.9935 | 688.61 | 17.70 |
| 18.2959 | 949.30 | 24.40 |
| 18.5258 | 438.92 | 11.28 |
| 18.7728 | 1576.09 | 40.51 |
| 19.6638 | 1736.88 | 44.65 |
| 20.4019 | 3047.78 | 78.34 |
| 20.8566 | 1106.70 | 28.45 |
| 21.2027 | 1108.07 | 28.48 |
| 21.3736 | 3408.70 | 87.62 |
| 21.6173 | 1442.13 | 37.07 |
| 22.0030 | 1007.70 | 25.90 |
| 22.1468 | 952.47 | 24.48 |
| 22.4678 | 1464.52 | 37.65 |
| 22.9236 | 1346.02 | 34.60 |
| 23.4098 | 190.08 | 4.89 |
| 24.1636 | 795.75 | 20.46 |
| 24.6355 | 626.92 | 16.12 |
| 24.8676 | 300.92 | 7.74 |
| 25.2453 | 286.57 | 7.37 |
| 25.4632 | 287.25 | 7.38 |
| 25.9375 | 1191.81 | 30.64 |
| 26.4465 | 1452.00 | 37.32 |
| 27.2385 | 416.92 | 10.72 |
| 27.8576 | 510.92 | 13.13 |
| 28.1594 | 703.92 | 18.09 |
| 28.6842 | 202.85 | 5.21 |
| 29.1886 | 351.92 | 9.05 |
| 30.2331 | 173.49 | 4.46 |
| 30.8093 | 221.03 | 5.68 |

TABLE 5-continued

| Pos. [°2θ] | Height [cts] | Rel. Int. |
|---|---|---|
| 32.2440 | 218.36 | 5.61 |
| 32.6305 | 193.59 | 4.98 |
| 33.2034 | 126.92 | 3.26 |
| 33.6754 | 134.92 | 3.47 |
| 34.5344 | 31.92 | 0.82 |

Example 25. Mesylate Pattern 2 (Acetone:Water (90:10 v/v)): XRPD Peak List

TABLE 6

| Pos. [°2θ] | Height [cts] | Rel. Int. |
|---|---|---|
| 3.2104 | 975.97 | 68.56 |
| 4.3126 | 813.06 | 57.12 |
| 5.9916 | 946.70 | 66.51 |
| 7.4447 | 164.30 | 11.54 |
| 9.3645 | 243.64 | 17.12 |
| 9.6885 | 336.45 | 23.64 |
| 9.9966 | 111.19 | 7.81 |
| 10.3209 | 187.08 | 13.14 |
| 11.8020 | 216.19 | 15.19 |
| 12.0313 | 464.41 | 32.63 |
| 12.3878 | 434.07 | 30.49 |
| 12.7870 | 736.05 | 51.71 |
| 13.6046 | 239.65 | 16.84 |
| 14.3857 | 279.19 | 19.61 |
| 14.5904 | 598.83 | 42.07 |
| 14.9160 | 239.19 | 16.80 |
| 15.1627 | 226.19 | 15.89 |
| 15.7759 | 561.39 | 39.44 |
| 15.9359 | 474.05 | 33.30 |
| 16.3636 | 263.96 | 18.54 |
| 17.5056 | 812.69 | 57.09 |
| 18.0062 | 222.19 | 15.61 |
| 18.4116 | 596.47 | 41.90 |
| 18.9363 | 1037.27 | 72.87 |
| 19.4525 | 669.71 | 47.05 |
| 19.7728 | 447.25 | 31.42 |
| 20.1145 | 373.21 | 26.22 |
| 20.6143 | 1423.42 | 100.00 |
| 21.3512 | 684.84 | 48.11 |
| 22.1408 | 299.87 | 21.07 |
| 22.7308 | 820.20 | 57.62 |
| 23.2392 | 635.60 | 44.65 |
| 23.8175 | 633.78 | 44.52 |
| 24.0397 | 550.19 | 38.65 |
| 24.8469 | 492.27 | 34.58 |
| 25.4521 | 384.31 | 27.00 |
| 26.0833 | 384.19 | 26.99 |
| 26.6795 | 195.49 | 13.73 |
| 27.1575 | 113.19 | 7.95 |
| 27.8454 | 145.62 | 10.23 |
| 28.7187 | 183.33 | 12.88 |
| 29.7607 | 99.03 | 6.96 |
| 31.1650 | 92.04 | 6.47 |
| 32.1555 | 64.60 | 4.54 |
| 33.2176 | 88.18 | 6.19 |

Example 26. Oxalate Pattern 1 (2-propanol): XRPD Peak List

TABLE 7

| Pos. [°2θ] | Height [cts] | Rel. Int. |
|---|---|---|
| 4.9532 | 1449.82 | 100.00 |
| 6.1637 | 198.63 | 13.70 |
| 7.2943 | 1236.55 | 85.29 |
| 7.7207 | 90.75 | 6.26 |

TABLE 7-continued

| Pos. [°2θ] | Height [cts] | Rel. Int. |
|---|---|---|
| 8.3148 | 116.52 | 8.04 |
| 9.8933 | 275.73 | 19.02 |
| 10.0378 | 341.64 | 23.56 |
| 12.2572 | 389.69 | 26.88 |
| 13.1795 | 436.58 | 30.11 |
| 13.3769 | 989.08 | 68.22 |
| 13.9612 | 300.49 | 20.73 |
| 14.5695 | 143.19 | 9.88 |
| 14.8668 | 290.57 | 20.04 |
| 15.0420 | 384.10 | 26.49 |
| 16.1696 | 466.54 | 32.18 |
| 16.4614 | 357.10 | 24.63 |
| 17.2938 | 581.79 | 40.13 |
| 18.0668 | 527.73 | 36.40 |
| 18.6224 | 398.01 | 27.45 |
| 19.4090 | 282.71 | 19.50 |
| 19.6513 | 143.92 | 9.93 |
| 20.1142 | 481.12 | 33.18 |
| 20.4050 | 236.98 | 16.35 |
| 20.6432 | 109.39 | 7.55 |
| 21.3207 | 655.65 | 45.22 |
| 22.0879 | 222.23 | 15.33 |
| 22.5352 | 735.64 | 50.74 |
| 22.8692 | 1366.32 | 94.24 |
| 23.3140 | 516.04 | 35.59 |
| 24.0468 | 258.86 | 17.85 |
| 24.3692 | 542.51 | 37.42 |
| 24.7043 | 756.10 | 52.15 |
| 25.7054 | 166.45 | 11.48 |
| 26.1300 | 189.65 | 13.08 |
| 26.6847 | 340.50 | 23.49 |
| 27.4517 | 354.35 | 24.44 |
| 28.5093 | 90.89 | 6.27 |
| 29.3658 | 143.23 | 9.88 |
| 29.8396 | 139.91 | 9.65 |
| 30.2682 | 96.42 | 6.65 |
| 31.3451 | 94.72 | 6.53 |
| 31.6554 | 117.78 | 8.12 |
| 33.2878 | 48.96 | 3.38 |
| 34.2219 | 129.90 | 8.96 |

Example 27. Oxalate Pattern 2 (Acetone:Water (90:10 v/v)): XRPD Peak List

TABLE 8

| Pos. [°2θ] | Height [cts] | Rel. Int. |
|---|---|---|
| 3.8204 | 1023.49 | 74.65 |
| 4.2694 | 1006.07 | 73.38 |
| 5.6244 | 367.95 | 26.84 |
| 6.5112 | 296.13 | 21.60 |
| 6.9639 | 495.46 | 36.14 |
| 8.1270 | 1093.19 | 79.74 |
| 9.0666 | 199.42 | 14.55 |
| 10.3663 | 393.99 | 28.74 |
| 10.7413 | 205.63 | 15.00 |
| 11.3178 | 123.75 | 9.03 |
| 11.7667 | 96.25 | 7.02 |
| 12.3780 | 297.43 | 21.69 |
| 13.0244 | 156.89 | 11.44 |
| 13.6355 | 398.52 | 29.07 |
| 14.4623 | 337.59 | 24.62 |
| 14.8263 | 177.63 | 12.96 |
| 15.3745 | 252.52 | 18.42 |
| 15.7939 | 185.74 | 13.55 |
| 16.4008 | 358.23 | 26.13 |
| 16.9166 | 290.61 | 21.20 |
| 17.3729 | 249.95 | 18.23 |
| 17.6682 | 438.94 | 32.02 |
| 18.1633 | 935.58 | 68.24 |
| 18.3587 | 513.22 | 37.43 |
| 19.0634 | 774.23 | 56.47 |
| 19.8595 | 594.91 | 43.39 |

TABLE 8-continued

| Pos. [°2θ] | Height [cts] | Rel. Int. |
|---|---|---|
| 20.3863 | 720.10 | 52.52 |
| 20.7089 | 1370.99 | 100.00 |
| 21.1449 | 567.18 | 41.37 |
| 22.3294 | 980.33 | 71.51 |
| 22.7660 | 691.29 | 50.42 |
| 23.1962 | 575.17 | 41.95 |
| 23.5383 | 572.83 | 41.78 |
| 23.9992 | 539.12 | 39.32 |
| 24.5505 | 555.75 | 40.54 |
| 24.9379 | 667.00 | 48.65 |
| 25.6244 | 614.75 | 44.84 |
| 26.9282 | 433.69 | 31.63 |
| 28.5609 | 105.52 | 7.70 |
| 29.4356 | 100.05 | 7.30 |

Example 28. Esylate Pattern 1 (2-Propanol):XRPD Peak List

TABLE 9

| Pos. [°2θ] | Height [cts] | Rel. Int. |
|---|---|---|
| 5.4182 | 2523.05 | 94.32 |
| 5.7226 | 212.08 | 7.93 |
| 9.4519 | 452.55 | 16.92 |
| 9.7709 | 1461.39 | 54.63 |
| 10.8340 | 1561.38 | 58.37 |
| 11.0000 | 596.90 | 22.31 |
| 11.7890 | 856.82 | 32.03 |
| 13.3227 | 284.21 | 10.62 |
| 13.5503 | 332.12 | 12.42 |
| 13.9236 | 430.32 | 16.09 |
| 14.3536 | 747.32 | 27.94 |
| 14.6610 | 494.56 | 18.49 |
| 14.7960 | 345.01 | 12.90 |
| 15.0602 | 766.95 | 28.67 |
| 15.5639 | 1009.54 | 37.74 |
| 15.7577 | 340.61 | 12.73 |
| 16.2767 | 220.92 | 8.26 |
| 17.1600 | 869.09 | 32.49 |
| 17.4509 | 539.09 | 20.15 |
| 17.6937 | 828.03 | 30.95 |
| 18.1813 | 551.23 | 20.61 |
| 18.8180 | 1248.82 | 46.68 |
| 18.9824 | 921.79 | 34.46 |
| 19.6693 | 1256.96 | 46.99 |
| 20.5851 | 440.66 | 16.47 |
| 21.0850 | 2675.13 | 100.00 |
| 21.4834 | 1003.94 | 37.53 |
| 21.7565 | 1053.26 | 39.37 |
| 22.0457 | 598.68 | 22.38 |
| 22.3107 | 1111.79 | 41.56 |
| 23.1703 | 390.24 | 14.59 |
| 23.7448 | 761.15 | 28.45 |
| 23.9081 | 518.70 | 19.39 |
| 24.4576 | 669.04 | 25.01 |
| 24.9599 | 180.89 | 6.76 |
| 25.5780 | 445.56 | 16.66 |
| 25.9086 | 549.74 | 20.55 |
| 26.6417 | 432.04 | 16.15 |
| 27.2891 | 219.88 | 8.22 |
| 27.5817 | 513.64 | 19.20 |
| 28.5785 | 121.48 | 4.54 |
| 28.9965 | 198.67 | 7.43 |
| 29.5971 | 63.81 | 2.39 |
| 30.1716 | 75.23 | 2.81 |
| 30.3897 | 125.06 | 4.67 |
| 31.0846 | 78.32 | 2.93 |

Example 29. Esylate Pattern 2 (Anisole): XRPD Peak List

TABLE 10

| Pos. [°2θ] | Height [cts] | Rel. Int. |
|---|---|---|
| 5.4123 | 986.96 | 48.69 |
| 9.6642 | 668.83 | 32.99 |
| 9.9532 | 408.46 | 20.15 |
| 10.7777 | 726.81 | 35.85 |
| 10.9908 | 799.06 | 39.42 |
| 11.8302 | 446.75 | 22.04 |
| 13.3865 | 252.22 | 12.44 |
| 13.9832 | 249.01 | 12.28 |
| 14.5130 | 731.84 | 36.10 |
| 15.0235 | 640.93 | 31.62 |
| 15.6073 | 474.86 | 23.43 |
| 15.9886 | 701.76 | 34.62 |
| 17.2884 | 778.18 | 38.39 |
| 17.7412 | 619.42 | 30.56 |
| 18.7012 | 824.19 | 40.66 |
| 19.5647 | 937.99 | 46.27 |
| 20.0217 | 500.05 | 24.67 |
| 21.0255 | 2027.09 | 100.00 |
| 21.3918 | 819.86 | 40.45 |
| 22.0785 | 718.65 | 35.45 |
| 22.8159 | 382.14 | 18.85 |
| 23.6802 | 462.10 | 22.80 |
| 24.0516 | 632.10 | 31.18 |
| 25.8493 | 371.20 | 18.31 |
| 26.9534 | 273.69 | 13.50 |
| 27.7402 | 172.31 | 8.50 |
| 28.1612 | 167.16 | 8.25 |
| 29.2755 | 127.69 | 6.30 |
| 30.5014 | 61.30 | 3.02 |

Example 30. Fumarate Pattern 1 (2-propanol): XRPD Peak List

TABLE 11

| Pos. [°2θ] | Height [cts] | Rel. Int. |
|---|---|---|
| 3.6528 | 2721.00 | 100.00 |
| 5.3346 | 401.76 | 14.77 |
| 6.1921 | 208.30 | 7.66 |
| 7.1693 | 749.52 | 27.55 |
| 7.2584 | 398.16 | 14.63 |
| 7.9555 | 181.24 | 6.66 |
| 8.2989 | 210.29 | 7.73 |
| 9.2514 | 50.60 | 1.86 |
| 10.5913 | 111.17 | 4.09 |
| 11.1450 | 749.78 | 27.56 |
| 12.0332 | 984.10 | 36.17 |
| 12.7127 | 293.05 | 10.77 |
| 13.1965 | 569.63 | 20.93 |
| 13.5693 | 214.22 | 7.87 |
| 13.8163 | 306.41 | 11.26 |
| 14.3773 | 502.19 | 18.46 |
| 14.6066 | 328.44 | 12.07 |
| 15.3422 | 429.47 | 15.78 |
| 15.5476 | 423.35 | 15.56 |
| 15.9810 | 889.19 | 32.68 |
| 16.6013 | 379.65 | 13.95 |
| 17.5327 | 244.32 | 8.98 |
| 17.8949 | 857.50 | 31.51 |
| 18.2706 | 629.17 | 23.12 |
| 19.0516 | 721.07 | 26.50 |
| 19.3988 | 568.32 | 20.89 |
| 19.8836 | 128.89 | 4.74 |
| 20.2075 | 281.33 | 10.34 |
| 20.3963 | 232.83 | 8.56 |
| 20.7842 | 396.46 | 14.57 |
| 21.1854 | 981.38 | 36.07 |
| 21.8139 | 347.14 | 12.76 |

TABLE 11-continued

| Pos. [°2θ] | Height [cts] | Rel. Int. |
|---|---|---|
| 22.0119 | 356.63 | 13.11 |
| 22.4021 | 210.78 | 7.75 |
| 22.6620 | 465.25 | 17.10 |
| 22.9995 | 1733.03 | 63.69 |
| 23.2815 | 829.33 | 30.48 |
| 23.5370 | 509.46 | 18.72 |
| 23.9934 | 492.05 | 18.08 |
| 24.6748 | 1605.41 | 59.00 |
| 24.8788 | 1430.78 | 52.58 |
| 25.7236 | 1394.90 | 51.26 |
| 26.0766 | 544.72 | 20.02 |
| 26.8205 | 498.71 | 18.33 |
| 27.8212 | 471.32 | 17.32 |
| 28.5683 | 563.10 | 20.69 |
| 28.9477 | 276.52 | 10.16 |
| 29.3638 | 462.18 | 16.99 |
| 30.7259 | 388.33 | 14.27 |
| 32.1373 | 247.81 | 9.11 |

Example 31. Fumarate Pattern 2 (Acetone:Water (90:10 v/v)): XRPD Peak List

TABLE 12

| Pos. [°2θ] | Height [cts] | Rel. Int. |
|---|---|---|
| 4.2283 | 814.45 | 93.20 |
| 5.2902 | 418.95 | 47.94 |
| 5.7064 | 189.90 | 21.73 |
| 7.0087 | 103.69 | 11.87 |
| 7.2740 | 88.69 | 10.15 |
| 8.4471 | 125.02 | 14.31 |
| 10.2953 | 253.66 | 29.03 |
| 10.4698 | 121.69 | 13.93 |
| 11.1043 | 142.69 | 16.33 |
| 11.2764 | 457.42 | 52.34 |
| 11.6690 | 474.89 | 54.34 |
| 12.0243 | 312.69 | 35.78 |
| 12.3661 | 439.60 | 50.30 |
| 12.6972 | 410.41 | 46.96 |
| 13.0211 | 360.84 | 41.29 |
| 13.2807 | 409.51 | 46.86 |
| 14.8277 | 449.89 | 51.48 |
| 15.4615 | 354.89 | 40.61 |
| 15.8235 | 312.69 | 35.78 |
| 16.0773 | 278.69 | 31.89 |
| 16.9930 | 478.20 | 54.72 |
| 17.2436 | 561.53 | 64.26 |
| 18.1053 | 374.04 | 42.80 |
| 19.5434 | 216.62 | 24.79 |
| 20.7010 | 868.87 | 99.43 |
| 21.1934 | 354.94 | 40.62 |
| 21.9721 | 221.69 | 25.37 |
| 22.2605 | 256.69 | 29.37 |
| 22.6296 | 476.69 | 54.55 |
| 23.6035 | 873.89 | 100.00 |
| 23.7351 | 738.81 | 84.54 |
| 24.0613 | 490.71 | 56.15 |
| 24.4738 | 567.73 | 64.97 |
| 24.9772 | 542.00 | 62.02 |
| 25.5868 | 252.89 | 28.94 |
| 26.0270 | 293.74 | 33.61 |
| 27.2637 | 172.10 | 19.69 |
| 27.9596 | 217.37 | 24.87 |
| 28.5769 | 248.86 | 28.48 |
| 30.7356 | 73.69 | 8.43 |
| 31.2491 | 124.49 | 14.25 |

Example 32. Fumarate Pattern 3 (2-propanol/Water (Re-Preparations)): XRPD Peak List

TABLE 13

| Pos. | Height | Rel. |
|---|---|---|
| 4.6078 | 1598.29 | 100.00 |
| 4.7247 | 702.13 | 43.93 |
| 5.6369 | 90.25 | 5.65 |
| 5.7945 | 429.87 | 26.90 |
| 6.9083 | 392.40 | 24.55 |
| 7.2036 | 260.42 | 16.29 |
| 7.4378 | 61.20 | 3.83 |
| 9.2520 | 317.93 | 19.89 |
| 9.3801 | 258.93 | 16.20 |
| 10.0352 | 411.00 | 25.72 |
| 10.3048 | 49.93 | 3.12 |
| 11.1685 | 1150.19 | 71.96 |
| 11.4467 | 511.93 | 32.03 |
| 11.7464 | 234.39 | 14.66 |
| 12.7059 | 133.93 | 8.38 |
| 13.1603 | 736.16 | 46.06 |
| 13.3277 | 641.44 | 40.13 |
| 13.6611 | 593.75 | 37.15 |
| 14.2278 | 408.21 | 25.54 |
| 14.6322 | 1171.55 | 73.30 |
| 14.9188 | 384.93 | 24.08 |
| 15.0644 | 561.47 | 35.13 |
| 15.7469 | 676.52 | 42.33 |
| 15.9535 | 507.66 | 31.76 |
| 16.2032 | 678.88 | 42.48 |
| 16.3240 | 547.82 | 34.28 |
| 16.6769 | 329.75 | 20.63 |
| 17.4243 | 429.52 | 26.87 |
| 18.2889 | 699.16 | 43.74 |
| 18.8043 | 697.95 | 43.67 |
| 19.2960 | 874.40 | 54.71 |
| 19.5746 | 1017.59 | 63.67 |
| 19.9329 | 1062.60 | 66.48 |
| 20.2723 | 876.82 | 54.86 |
| 20.5228 | 1501.47 | 93.94 |
| 21.1443 | 770.54 | 48.21 |
| 21.5244 | 426.96 | 26.71 |
| 21.7014 | 707.54 | 44.27 |
| 22.0764 | 276.93 | 17.33 |
| 22.3112 | 634.93 | 39.73 |
| 22.3752 | 708.93 | 44.36 |
| 22.6648 | 541.01 | 33.85 |
| 22.8586 | 880.24 | 55.07 |
| 23.1084 | 959.94 | 60.06 |
| 23.2825 | 1037.93 | 64.94 |
| 23.5664 | 839.66 | 52.53 |
| 23.9441 | 420.93 | 26.34 |
| 24.1708 | 1003.05 | 62.76 |
| 24.2438 | 1135.70 | 71.06 |
| 24.5667 | 960.38 | 60.09 |
| 24.7979 | 626.93 | 39.22 |
| 25.2094 | 1204.78 | 75.38 |
| 25.5564 | 859.76 | 53.79 |
| 26.3596 | 605.93 | 37.91 |
| 26.4901 | 804.07 | 50.31 |
| 26.8577 | 710.95 | 44.48 |
| 27.3567 | 818.89 | 51.24 |
| 27.6722 | 410.93 | 25.71 |
| 28.0031 | 379.93 | 23.77 |
| 28.3434 | 638.30 | 39.94 |
| 28.6121 | 378.12 | 23.66 |
| 29.0080 | 437.12 | 27.35 |
| 29.5671 | 326.99 | 20.46 |
| 30.6297 | 327.67 | 20.50 |
| 31.2974 | 414.54 | 25.94 |
| 31.9650 | 372.80 | 23.32 |
| 32.3013 | 217.89 | 13.63 |
| 33.4812 | 144.06 | 9.01 |
| 33.9277 | 154.89 | 9.69 |
| 34.2253 | 139.09 | 8.70 |

Example 33. Fumarate Pattern 4 (2-propanol/Water (Scale-Up)): XRPD Peak List

TABLE 14

| Pos. [°2θ] | Height [cts] | Rel. Int. |
|---|---|---|
| 4.8468 | 300.55 | 46.00 |
| 7.2009 | 154.02 | 23.57 |
| 9.2287 | 237.04 | 36.28 |
| 9.8752 | 104.03 | 15.92 |
| 11.3790 | 573.80 | 87.82 |
| 12.3753 | 158.81 | 24.31 |
| 13.1003 | 208.76 | 31.95 |
| 13.3414 | 399.37 | 61.13 |
| 14.0505 | 653.36 | 100.00 |
| 14.4103 | 194.23 | 29.73 |
| 14.9682 | 205.60 | 31.47 |
| 15.5626 | 147.16 | 22.52 |
| 16.0210 | 407.61 | 62.39 |
| 16.2253 | 421.58 | 64.52 |
| 16.5208 | 189.43 | 28.99 |
| 16.8847 | 140.67 | 21.53 |
| 17.3260 | 190.98 | 29.23 |
| 18.0436 | 155.62 | 23.82 |
| 18.5063 | 215.33 | 32.96 |
| 19.5667 | 509.39 | 77.97 |
| 19.8049 | 496.12 | 75.93 |
| 20.4746 | 198.51 | 30.38 |
| 21.3412 | 286.69 | 43.88 |
| 21.6458 | 400.04 | 61.23 |
| 21.8878 | 323.73 | 49.55 |
| 22.4062 | 336.53 | 51.51 |
| 22.9397 | 499.51 | 76.45 |
| 23.2065 | 497.08 | 76.08 |
| 23.6258 | 468.15 | 71.65 |
| 23.8043 | 304.27 | 46.57 |
| 24.2839 | 509.97 | 78.05 |
| 24.5292 | 587.59 | 89.93 |
| 24.9422 | 271.15 | 41.50 |
| 25.6526 | 466.21 | 71.36 |
| 26.2095 | 247.47 | 37.88 |
| 26.5712 | 391.53 | 59.93 |
| 26.8039 | 269.49 | 41.25 |
| 27.3245 | 242.24 | 37.08 |
| 27.9402 | 292.13 | 44.71 |
| 28.3452 | 197.75 | 30.27 |
| 29.7807 | 187.95 | 28.77 |
| 30.4185 | 177.79 | 27.21 |
| 32.4348 | 153.96 | 23.56 |
| 33.9687 | 84.19 | 12.88 |

Example 34. Fumarate Pattern 5 (Pattern 4 after Slurrying in Water): XRPD Peak List

TABLE 15

| Pos. [°2θ] | Height [cts] | Rel. Int. |
|---|---|---|
| 5.2173 | 220.55 | 20.66 |
| 6.5788 | 368.80 | 34.54 |
| 10.4657 | 144.23 | 13.51 |
| 11.9526 | 279.79 | 26.21 |
| 12.2981 | 647.12 | 60.61 |
| 12.9633 | 131.78 | 12.34 |
| 13.1469 | 479.18 | 44.88 |
| 13.6532 | 355.99 | 33.35 |
| 13.9226 | 103.85 | 9.73 |
| 14.0801 | 106.90 | 10.01 |
| 14.8387 | 127.52 | 11.94 |
| 15.2947 | 229.73 | 21.52 |
| 15.7415 | 182.38 | 17.08 |
| 16.0705 | 365.39 | 34.23 |
| 17.0800 | 148.83 | 13.94 |
| 17.8037 | 173.34 | 16.24 |
| 18.0998 | 187.12 | 17.53 |

TABLE 15-continued

| Pos. [°2θ] | Height [cts] | Rel. Int. |
|---|---|---|
| 19.2649 | 130.59 | 12.23 |
| 19.6536 | 485.96 | 45.52 |
| 20.4686 | 317.43 | 29.73 |
| 20.9891 | 623.39 | 58.39 |
| 21.5138 | 280.59 | 26.28 |
| 22.3786 | 233.51 | 21.87 |
| 23.1604 | 615.28 | 57.63 |
| 24.0181 | 580.97 | 54.42 |
| 24.7153 | 601.56 | 56.35 |
| 25.0063 | 550.78 | 51.59 |
| 25.3823 | 980.84 | 91.87 |
| 26.0374 | 1067.59 | 100.00 |
| 26.3551 | 541.45 | 50.72 |
| 27.5053 | 631.24 | 59.13 |
| 28.0100 | 468.63 | 43.90 |
| 28.7269 | 530.89 | 49.73 |
| 31.3366 | 242.78 | 22.74 |
| 32.4594 | 166.76 | 15.62 |

Example 35. Fumarate Pattern 6 (Acetonitrile During Re-Preparations): XRPD Peak List

TABLE 16

| Pos. [°2θ] | Height [cts] | Rel. Int. |
|---|---|---|
| 6.6183 | 167.28 | 12.44 |
| 7.3884 | 246.01 | 18.30 |
| 7.6111 | 259.01 | 19.26 |
| 8.2981 | 533.31 | 39.66 |
| 8.8993 | 303.39 | 22.56 |
| 10.0751 | 355.47 | 26.44 |
| 11.1019 | 442.91 | 32.94 |
| 11.5582 | 131.47 | 9.78 |
| 11.8344 | 584.24 | 43.45 |
| 12.2224 | 200.75 | 14.93 |
| 12.9751 | 524.10 | 38.98 |
| 13.4040 | 681.11 | 50.65 |
| 13.8874 | 390.10 | 29.01 |
| 14.2668 | 353.00 | 26.25 |
| 14.4971 | 388.85 | 28.92 |
| 15.0582 | 391.06 | 29.08 |
| 15.7548 | 421.12 | 31.32 |
| 16.3188 | 693.31 | 51.56 |
| 17.3388 | 354.15 | 26.34 |
| 17.9628 | 380.24 | 28.28 |
| 18.5415 | 806.29 | 59.96 |
| 18.9064 | 452.13 | 33.63 |
| 19.4667 | 197.47 | 14.69 |
| 19.7556 | 249.47 | 18.55 |
| 20.1836 | 381.08 | 28.34 |
| 20.7747 | 485.66 | 36.12 |
| 21.5446 | 910.06 | 67.68 |
| 22.2369 | 954.05 | 70.95 |
| 22.6652 | 512.47 | 38.11 |
| 23.0991 | 996.00 | 74.07 |
| 23.6074 | 772.71 | 57.47 |
| 23.8948 | 969.03 | 72.07 |
| 24.1368 | 1344.60 | 100.00 |
| 24.5986 | 1088.47 | 80.95 |
| 25.2568 | 845.47 | 62.88 |
| 25.9952 | 1088.47 | 80.95 |
| 26.9499 | 765.80 | 56.95 |
| 27.4845 | 598.47 | 44.51 |
| 27.8343 | 616.98 | 45.89 |
| 28.8828 | 718.59 | 53.44 |
| 29.2983 | 529.41 | 39.37 |
| 29.6677 | 397.47 | 29.56 |
| 30.1333 | 438.47 | 32.63 |
| 30.7281 | 355.12 | 26.41 |
| 31.5937 | 297.97 | 22.16 |
| 32.9662 | 297.45 | 22.12 |
| 33.8294 | 357.74 | 26.61 |

Example 36. Fumarate Pattern 7 (1-butanol During Re-Preparations): XRPD Peak List

TABLE 17

| Pos. [°2θ] | Height [cts] | Rel. Int. |
|---|---|---|
| 5.2074 | 268.12 | 33.24 |
| 6.5759 | 404.19 | 50.11 |
| 10.4268 | 127.44 | 15.80 |
| 11.9087 | 131.25 | 16.27 |
| 12.2972 | 298.81 | 37.05 |
| 12.8749 | 71.33 | 8.84 |
| 13.0948 | 244.23 | 30.28 |
| 13.6525 | 304.82 | 37.79 |
| 15.2610 | 169.55 | 21.02 |
| 15.7084 | 213.10 | 26.42 |
| 16.0248 | 319.57 | 39.62 |
| 16.4827 | 138.83 | 17.21 |
| 17.0200 | 192.29 | 23.84 |
| 17.7452 | 374.39 | 46.42 |
| 18.0663 | 356.50 | 44.20 |
| 19.2467 | 306.47 | 38.00 |
| 19.6260 | 691.53 | 85.74 |
| 20.4182 | 523.72 | 64.93 |
| 20.9504 | 806.57 | 100.00 |
| 21.1080 | 425.98 | 52.81 |
| 21.4534 | 378.56 | 46.94 |
| 22.2977 | 291.42 | 36.13 |
| 23.1512 | 675.69 | 83.77 |
| 23.9912 | 498.57 | 61.81 |
| 24.6413 | 358.91 | 44.50 |
| 24.9511 | 330.70 | 41.00 |
| 25.3280 | 703.69 | 87.24 |
| 25.9830 | 803.85 | 99.66 |
| 26.2805 | 402.66 | 49.92 |
| 27.4563 | 341.45 | 42.33 |
| 28.6746 | 215.20 | 26.68 |
| 29.6573 | 79.39 | 9.84 |
| 31.2290 | 55.54 | 6.89 |
| 32.3846 | 115.96 | 14.38 |

Example 37. Fumarate Pattern 8 (1-propanol During Re-Preparations): XRPD Peak List

TABLE 18

| Pos. [°2θ] | Height [cts] | Rel. Int. |
|---|---|---|
| 4.7133 | 245.00 | 17.67 |
| 7.0625 | 304.40 | 21.95 |
| 7.8327 | 461.97 | 33.31 |
| 9.4373 | 496.45 | 35.80 |
| 10.8320 | 66.07 | 4.76 |
| 11.2560 | 445.24 | 32.10 |
| 11.5530 | 251.70 | 18.15 |
| 12.1400 | 140.07 | 10.10 |
| 12.4180 | 370.12 | 26.69 |
| 13.2125 | 717.58 | 51.74 |
| 13.6676 | 285.64 | 20.60 |
| 14.1438 | 152.07 | 10.97 |
| 14.5314 | 276.64 | 19.95 |
| 14.8391 | 408.01 | 29.42 |
| 15.5031 | 163.07 | 11.76 |
| 15.6570 | 224.07 | 16.16 |
| 15.9242 | 298.95 | 21.56 |
| 16.2469 | 212.07 | 15.29 |
| 16.7975 | 366.37 | 26.42 |
| 18.0638 | 471.80 | 34.02 |
| 18.2986 | 344.07 | 24.81 |
| 18.6074 | 480.32 | 34.63 |
| 18.9236 | 393.71 | 28.39 |
| 19.0681 | 270.07 | 19.47 |
| 19.8194 | 287.71 | 20.75 |
| 20.2669 | 556.94 | 40.16 |
| 21.3752 | 584.86 | 42.17 |

TABLE 18-continued

| Pos. [°2θ] | Height [cts] | Rel. Int. |
|---|---|---|
| 21.6758 | 434.07 | 31.30 |
| 21.9446 | 671.16 | 48.39 |
| 22.6951 | 747.22 | 53.88 |
| 23.2295 | 486.07 | 35.05 |
| 23.6142 | 575.07 | 41.47 |
| 24.0109 | 597.00 | 43.05 |
| 24.4314 | 1382.12 | 99.66 |
| 25.2281 | 315.07 | 22.72 |
| 25.5842 | 1386.85 | 100.00 |
| 26.1514 | 271.07 | 19.55 |
| 26.7925 | 471.07 | 33.97 |
| 27.1916 | 319.07 | 23.01 |
| 28.1339 | 392.84 | 28.33 |
| 28.5109 | 507.45 | 36.59 |
| 29.2877 | 309.00 | 22.28 |
| 29.7222 | 174.07 | 12.55 |
| 30.6360 | 158.05 | 11.40 |
| 31.3505 | 190.37 | 13.73 |
| 32.6032 | 78.07 | 5.63 |
| 32.9347 | 116.91 | 8.43 |
| 33.8939 | 121.17 | 8.74 |

Example 38. Benzoate Pattern 1 (2-propanol):XRPD Peak List

TABLE 19

| Pos. [°2θ] | Height [cts] | Rel. Int. |
|---|---|---|
| 5.0941 | 297.32 | 88.69 |
| 10.2223 | 204.91 | 61.12 |
| 11.8691 | 118.15 | 35.24 |
| 13.2023 | 335.24 | 100.00 |
| 13.7755 | 152.50 | 45.49 |
| 13.9773 | 333.43 | 99.46 |
| 14.6467 | 79.62 | 23.75 |
| 15.9075 | 105.86 | 31.58 |
| 16.7186 | 110.67 | 33.01 |
| 20.4020 | 333.47 | 99.47 |
| 21.9198 | 189.30 | 56.47 |
| 23.0969 | 155.88 | 46.50 |
| 23.5325 | 274.39 | 81.85 |
| 24.4800 | 164.22 | 48.99 |
| 25.2794 | 134.00 | 39.97 |

Example 39. Succinate Pattern 1 (Acetone: Water (90:10 v/v)): XRPD Peak List

TABLE 20

| Pos. [°2θ] | Height [cts] | Rel. Int. |
|---|---|---|
| 4.1731 | 1536.07 | 100.00 |
| 5.1086 | 286.72 | 18.67 |
| 6.5676 | 392.68 | 25.56 |
| 7.9847 | 195.87 | 12.75 |
| 9.9321 | 359.08 | 23.38 |
| 10.3453 | 201.93 | 13.15 |
| 11.9442 | 155.73 | 10.14 |
| 13.1111 | 175.20 | 11.41 |
| 14.0979 | 247.70 | 16.13 |
| 14.5776 | 178.59 | 11.63 |
| 14.8894 | 146.58 | 9.54 |

TABLE 20-continued

| Pos. [°2θ] | Height [cts] | Rel. Int. |
|---|---|---|
| 15.4458 | 148.77 | 9.69 |
| 16.0064 | 120.74 | 7.86 |
| 17.5761 | 211.01 | 13.74 |
| 18.0178 | 481.64 | 31.36 |
| 18.5153 | 181.50 | 11.82 |
| 18.9551 | 172.30 | 11.22 |
| 19.2662 | 76.74 | 5.00 |
| 19.9186 | 168.28 | 10.96 |
| 20.3646 | 146.23 | 9.52 |
| 20.8102 | 173.87 | 11.32 |
| 21.1557 | 110.74 | 7.21 |
| 22.1676 | 196.95 | 12.82 |
| 22.3940 | 214.45 | 13.96 |
| 22.8184 | 164.74 | 10.72 |
| 23.2383 | 98.74 | 6.43 |
| 23.3762 | 186.57 | 12.15 |
| 24.1177 | 306.10 | 19.93 |
| 25.1899 | 125.90 | 8.20 |
| 25.5494 | 116.29 | 7.57 |
| 26.0776 | 68.02 | 4.43 |
| 27.5686 | 85.74 | 5.58 |

Example 40. Preparation of Tosylate Pattern 2

MTP-131 tosylate (35 mg) was dissolved in the minimum quantity of methanol in a 20 mL clear glass vial and tBME (approx. 300 μL) added until slight turbidity was noticed. This vial was capped and temperature cycled between 5 and 30° C. After one week, lath-like crystals were noted to have grown below the solution meniscus, that appeared suitable for interrogation by single crystal X-ray diffraction.

Example 41. Single Crystal X-ray Analysis (SXRD) of Tosylate Pattern 2

A colourless fragment of a lath (0.46×0.07×0.03 mm) was used in the single crystal diffraction study. The crystal was coated with Paratone oil and data collected on a Rigaku Oxford Diffraction (Dual Source) SuperNova diffractometer using mirror monochromated Cu Kα ($\lambda$=1.54184 Å, 40 kV/40 mA) radiation at 120(1) K using an Oxford Cryosystems 700+ low temperature device and Atlas CCD plate detector (Rigaku Oxford Diffraction). A total of 2672 frames were collected for a hemisphere of reflections using a ω strategy calculated by CrysAlisPro (Rigaku Oxford Diffraction 1.171.38.43h, 2015) over the Θ range 3.14-77.17° with 1° step size and 2 sec/frame exposure. Frames were integrated using CrysAlisPro (Rigaku Oxford Diffraction 1.171.38.43h, 2015) to a monoclinic cell using a moving average background, yielding a total of 52633 reflections, of which 17979 were independent (I>2σ(I)). Data were integrated to 2Θmax=154.34° (95.3% completeness), and fixed to 2Θfull=98.1° (98.1% completeness). Absorption corrections were applied using SADABS (Bruker 2001. Bruker AXS Inc., Madison, Wis., USA) using a multi-scan model (absorption coefficient=1.732 mm-1).

The OLEX2 graphical software package was used as an interface for phase determination and structure refinement. Data were solved using direct methods (SHELXS97) and developed by full least squares refinement on F2 (SHELXL97) in the monoclinic space-group P21 (E2-1=0.731). A search for higher metric symmetry using the ADDSYMM routine of PLATON was attempted, but failed to uncover any higher order symmetry. All non-hydrogen atoms were located in the Fourier map and their positions refined prior to describing their thermal movement of all non-hydrogen atoms anisotropically. Within the asymmetric unit, one complete, crystallographically independent MTP-131 formula unit, three associated p-tolyl-counterions, one fully occupied water molecule and one fully occupied methanol molecule were found. No disorder was modelled in the final structure. All hydrogen atoms were placed in calculated positions using a riding model with fixed Uiso at 1.2 times for all CH and CH2 groups, and 1.5 times for all CH3 and OH groups. The Flack parameter was refined to 0.017(10) for 4760 select quotients. Note: The Flack parameter is used to determine chirality of the crystal studied, the value should be near 0, a value of 1 means that the stereochemistry is wrong and the model should be inverted. A value of 0.5 means that the crystal consists of a racemic mixture of the two enantiomers. The highest residual Fourier peak was found to be 0.39 e.Å$^{-3}$ approx. 0.87 Å from O(9), and the deepest Fourier hole was found to be −0.45 e.Å$^{-3}$ approx. 0.71 Å from S(3).

Crystal Data $C_{54}H_{79}N_9O_{16}S_3$ (M=1206.44 g/mol): monoclinic, space group P21 (no. 4), a=7.98250(10) Å, b=26.9673(4) Å, c=14.5556(3) Å, β=104.770(2)°, V=3029.80(9) Å3, Z=2, T=120.01(10) K, μ (CuKα)=1.732 mm-1, Dcalc=1.322 g/cm3, 52633 reflections measured (6.28°≤2 θ≤154.348°), 12237 unique (Rint=0.0753, Rsigma=0.0723) which were used in all calculations. The final R1 was 0.0512 (I>2a(I)) and wR2 was 0.1325 (all data).

Example 42. Structural Features of Tosylate Pattern 2

Sample Features Include:

The unit cell dimensions of the collected structure were found to be as follows:

Monoclinic P21

| a = 7.98250(10) Å | α = 90° |
| b = 26.9673(4) Å | β = 104.770(2)° |
| c = 14.5556(3) Å | γ = 90° |

Volume=3029.80(9) A3

Z=2, Z'=1

The asymmetric unit was found to contain one complete, crystallographically independent MTP-131 formula unit, three associated p-tolulenesulfonate counterions, one fully occupied advantageous water molecule and one fully occupied methanol molecule, as shown in Figure.

The final refinement parameters were as follows:

R1 [I>2σ(I)]=5.12%

GooF (Goodness of fit)=1.029 wR2 (all data)=13.25%

Rint=7.53%

Figure 34:
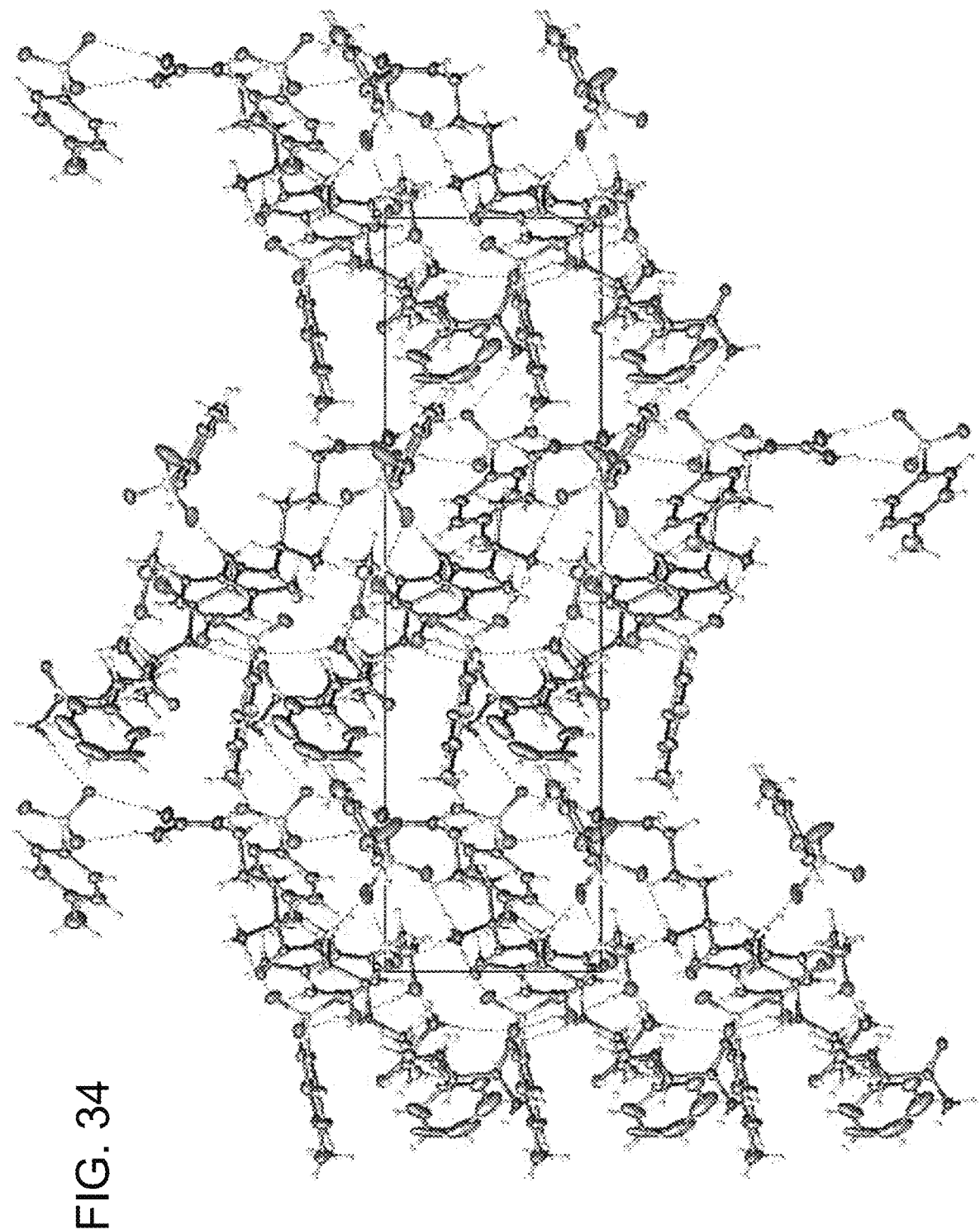
FIG. 34 depicts a view of unit cell c axis of MTP-131, Pattern 2 containing complete molecules. All atoms are shown with thermal ellipsoids set at the 50% probability level.

The model is suitable to confirm the connectivity and stereochemistry of the parent MTP-131 molecule, as shown below:

Calculated from the above structure, and using FIG. 30 or FIG. 34 as references, the chiral centers present in the analyzed MTP-131 tosylate, Pattern 2 crystal are summarized below. Note: Numbering in this structure is not according to systematic IUPAC guidelines.

C5—R
C7—S
C18—S
C24—S

Protonation of the arginine side-chain was confirmed by inspection of the guanidinium bond lengths, where two were found to be near identical, measuring C(1)-N(1) 1.338(6) A/C(1)-N(3) 1.336(6) A, while C(1)-N(2) was found to measure 1.322(6) A. Nitrogen atoms N(4) and N(7) were also found to be quaternary.

The structure of MTP-131 tosylate, Pattern 2 showed the stoichiometric hydrated and solvated nature of the form wherein one fully occupied water molecule and one fully occupied methanol molecule per MTP-131 formula unit were found.

No notable π . . . π interactions were observed in the structure implying packing within the structure is predominately stabilized by hydrogen-bonding between MTP-131, tosylate-counterions and solvent molecules, alongside a number of weak intermolecular forces (namely between short-atom contacts).

Figure 35:
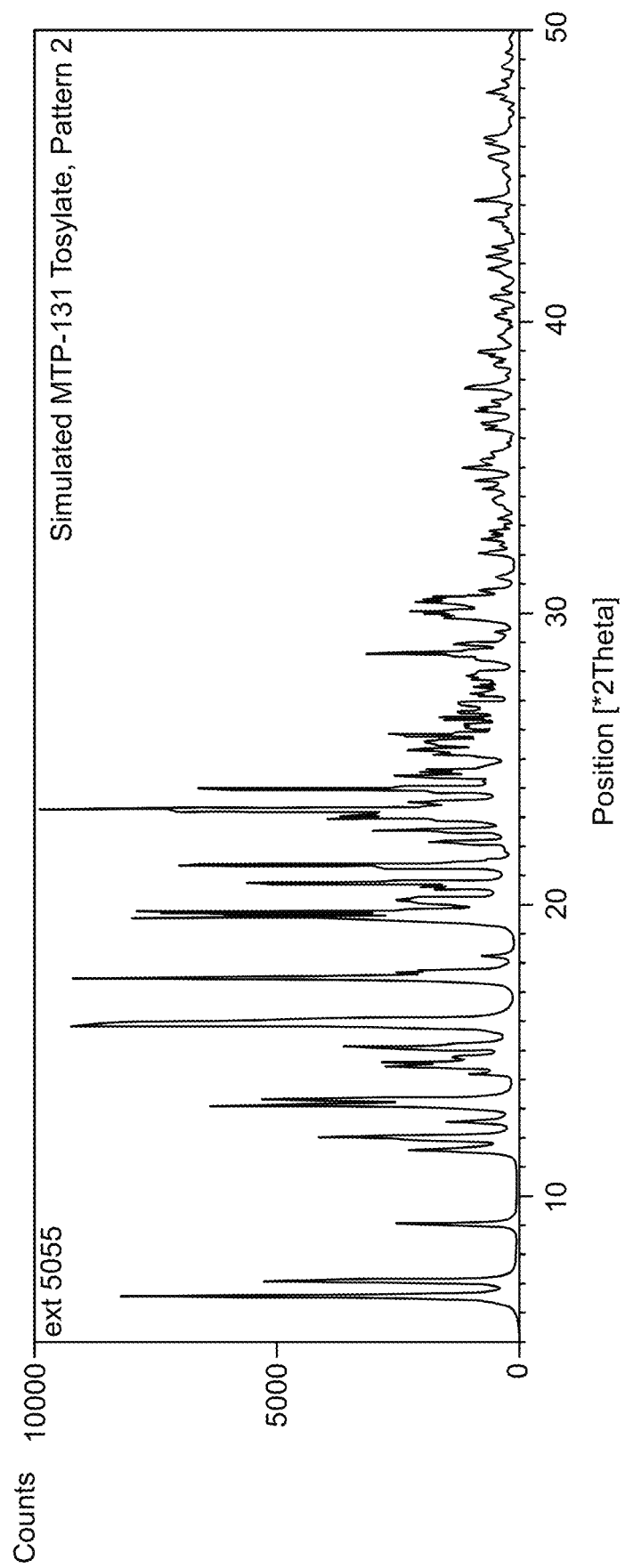
FIG. 35 depicts a simulated XRPD 2θ diffractogram of MTP-131 tosylate, Pattern 2.

The p-tolyl-counteranions were found to offer a complex hydrogen bonding network between adjacent MTP-131 parent molecules. The crystallized solvent molecules were also found to be integral hydrogen bond donors and acceptors with moderate strength and found within the same pocket, as shown in FIG. 35.

Key separations were found to be as following:

| H(5A) . . . O(9) | 1.963(4) Å |
| O(9) . . . H(16)$^i$ | 2.138(6) Å |
| O(16)$^i$ . . . H(7B) | 2.062(4) Å |

| | | |
|---|---|---|
| H(7A) ... O(15) | 1.836(3) Å | |
| H(15) ... O(2)$^i$ | 1.918(3) Å | |

Symmetry code: (i) +x, +y, −1+z.

Figure 30:
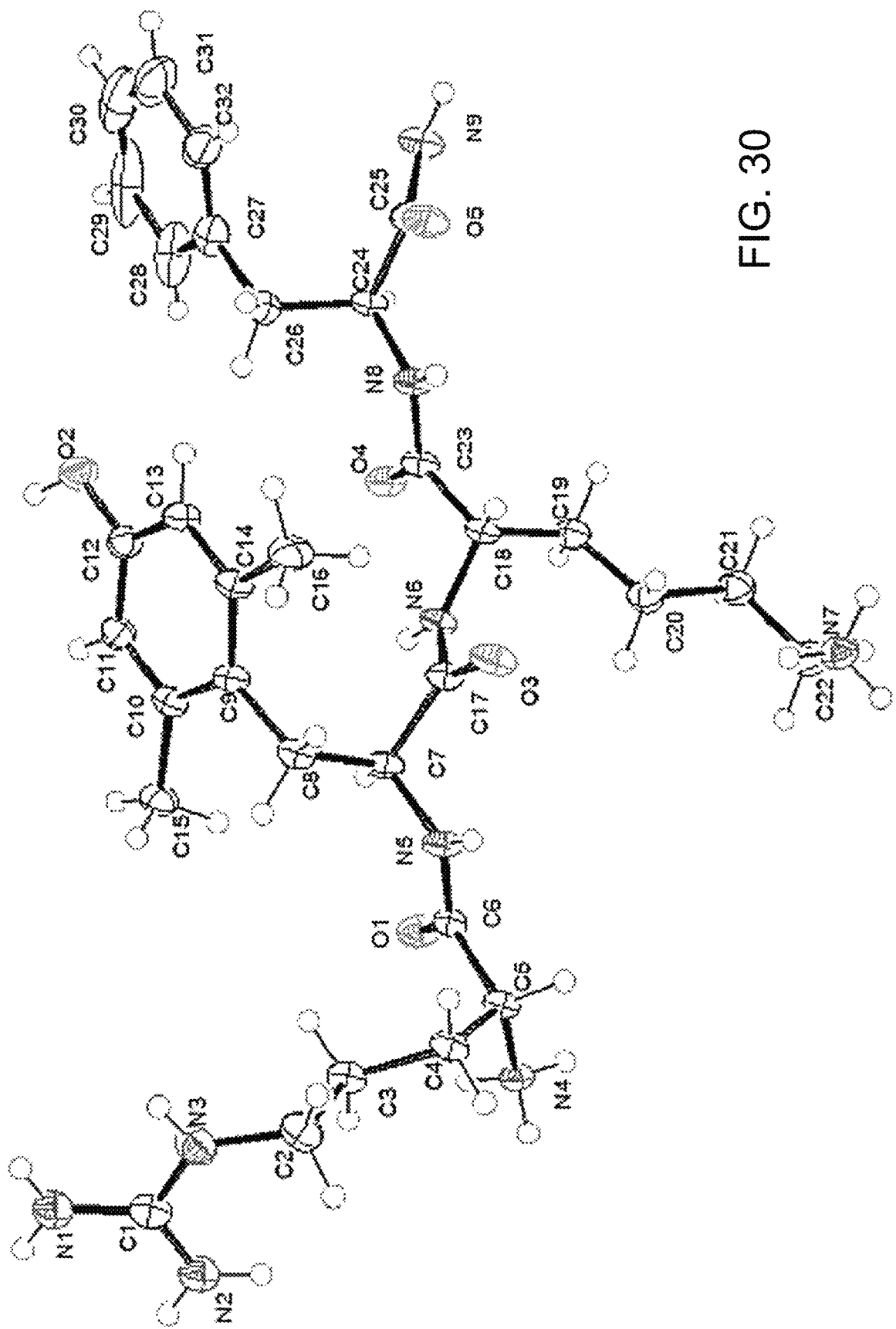
FIG. 30 depicts an ORTEP view of MTP-131 parent molecule with atom labels. All non-hydrogen atoms are shown with thermal ellipsoids set at the 50% probability level.
Figure 31:
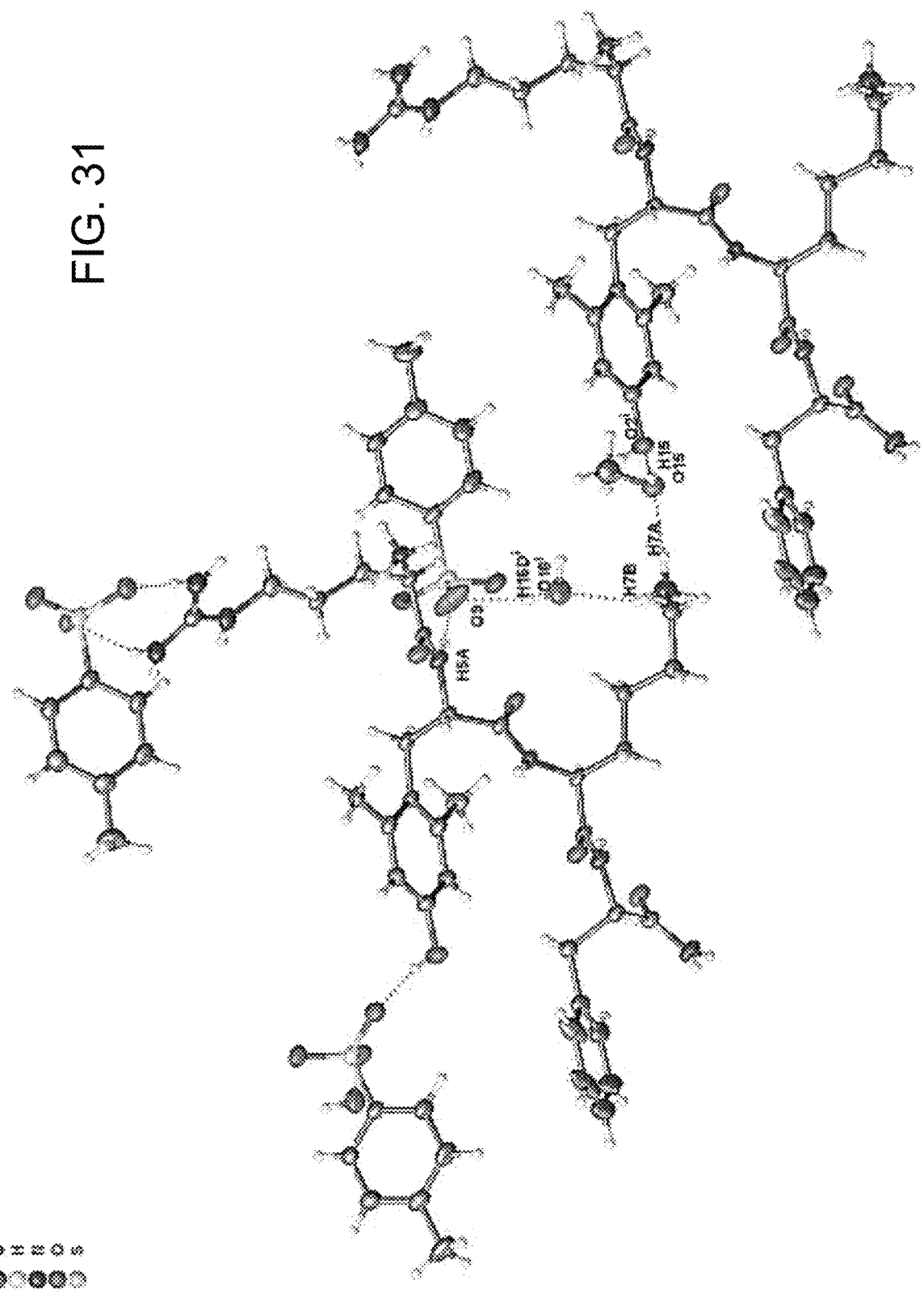
FIG. 31 depicts Hydrogen bond clashing between adjacent hydrogen atoms of parent MTP-131, Pattern 2 molecules. All non-hydrogen atoms are shown with thermal ellipsoids set at the 50% probability level. (Symmetry Code: (i) +x, +y, −1+z).
Figure 32:
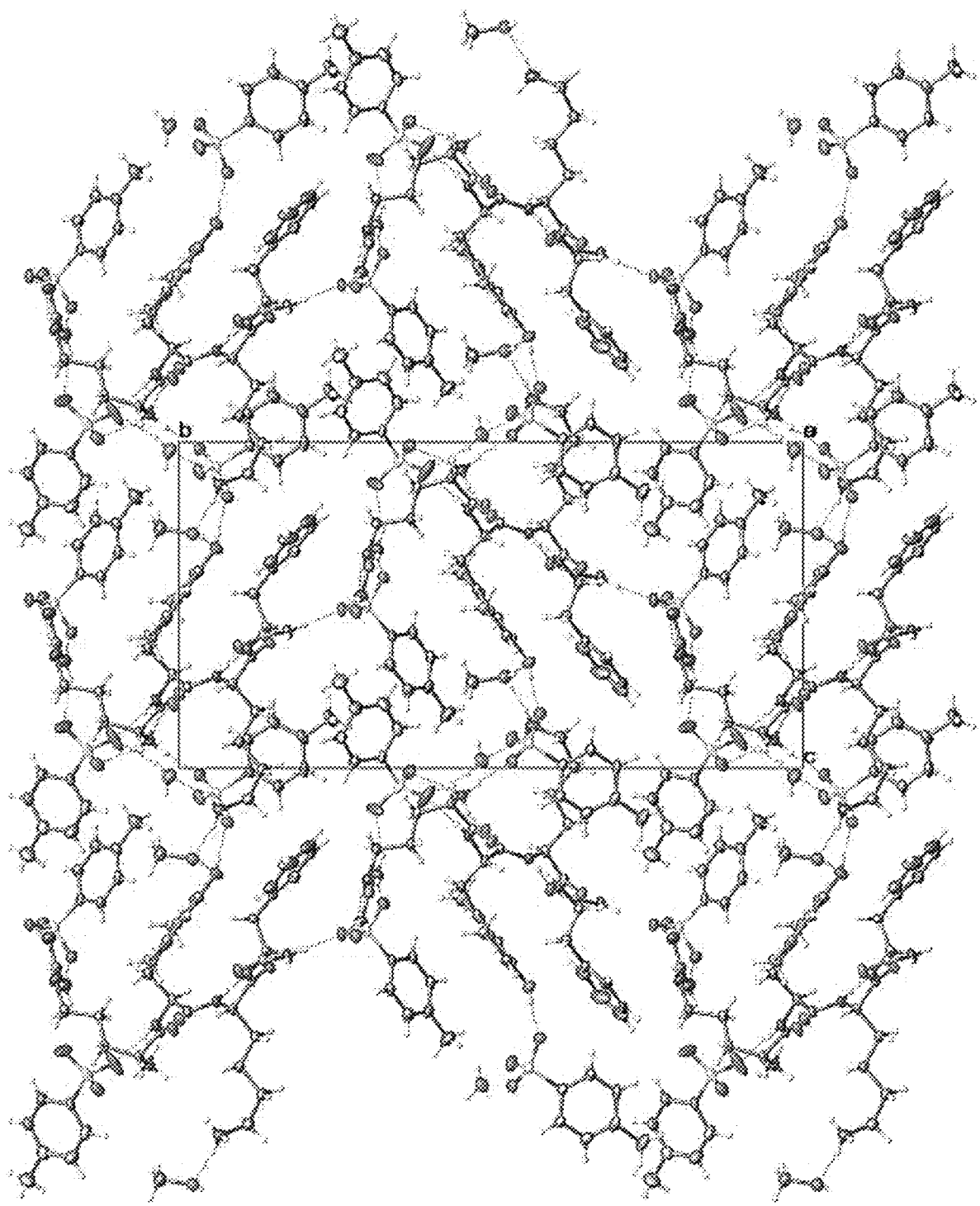
FIG. 32 depicts a view of unit cell a axis of MTP-131, Pattern 2 containing complete molecules. All atoms are shown with thermal ellipsoids set at the 50% probability level.
Figure 33:
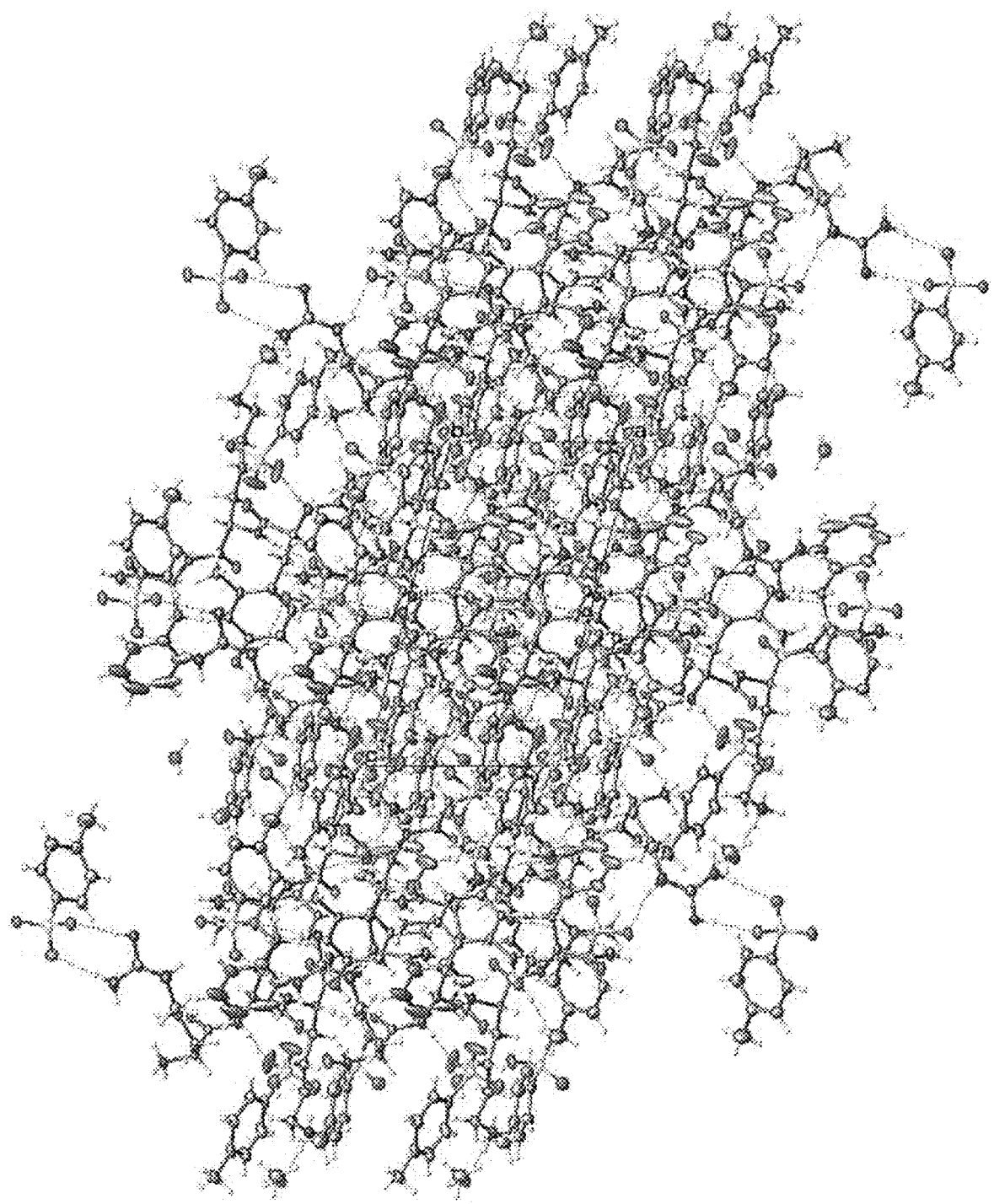
FIG. 33 depicts a view of unit cell a axis of MTP-131, Pattern 2 containing complete molecules. All atoms are shown with thermal ellipsoids set at the 50% probability level.
Figure 36:
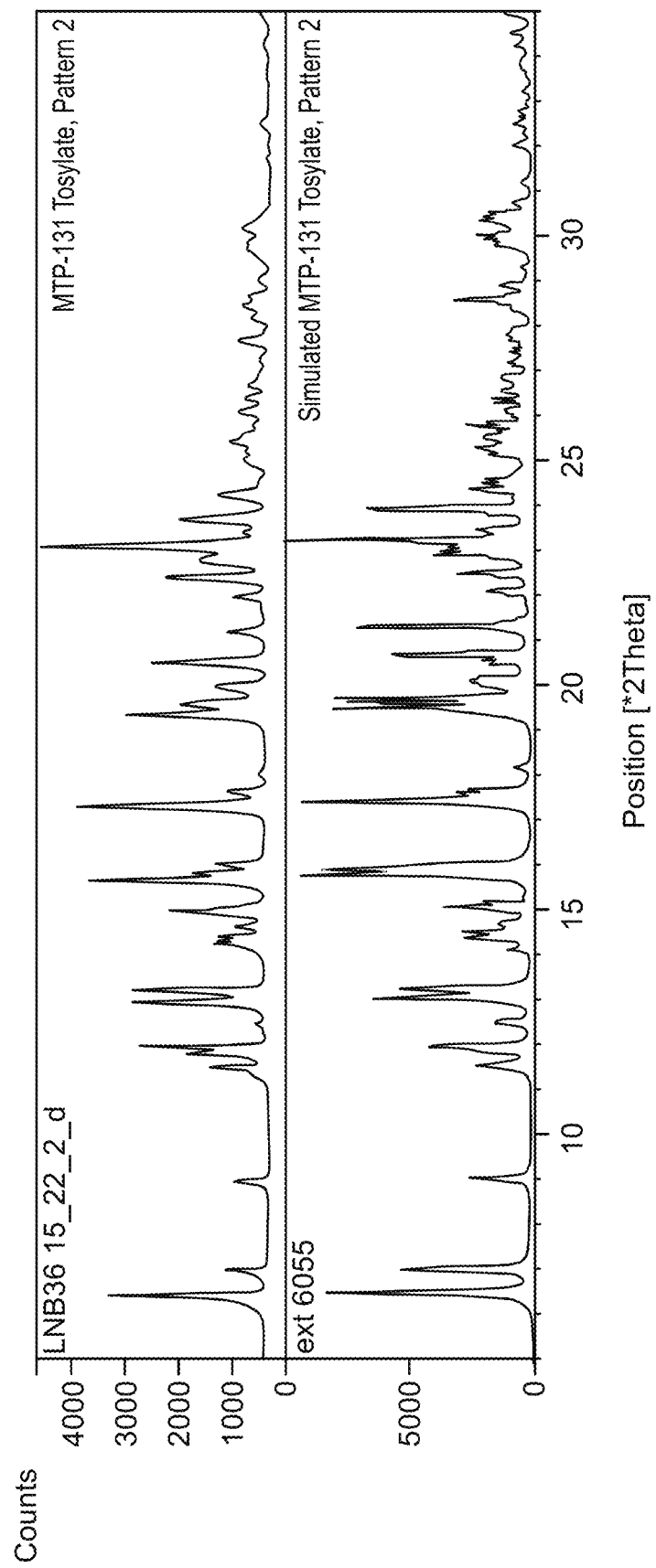
FIG. 36 depicts a comparison of MTP-131 tosylate, Pattern 2, and simulated MTP-131 tosylate, Pattern 2 XRPD 2θ diffractograms.

When viewed along unit cell axes a, b and c, the structure was found to be tightly packed as shown in FIG. 30-FIG. 32 and confirmed in the calculated density 1.322 g·cm$^{-3}$ A simulated XRPD diffractogram has been calculated (FIG. 35) and compared to experimental (room temperature) data (FIG. 36). Excellent overlap has been observed between simulated diffractogram and previously prepared MTP-131 tosylate, Pattern 2.

TABLE 21

Crystallographic parameters and refinement indicators of MTP-131, Pattern 2. MTP-131, Form 2

| | |
|---|---|
| Empirical formula | $C_{54}H_{79}N_9O_{16}S_3$ |
| Formula weight | 1206.44 |
| Temperature/K | 120(1) |
| Crystal system | monoclinic |
| Space group | P2$_1$ |
| a/Å | 7.98250(10) |
| b/Å | 26.9673(4) |
| c/Å | 14.5556(3) |
| α/° | 90 |
| β/° | 104.770(2) |
| γ/° | 90 |
| Volume/Å$^3$ | 3029.80(9) |
| Z, Z' | 2 |
| $\rho_{calc}$ g/cm$^3$ | 1.322 |
| μ/mm$^{-1}$ | 1.732 |
| F(000) | 1284.0 |
| Crystal size/mm$^3$ | 0.463 × 0.072 × 0.026 |
| Radiation | CuKα (λ = 1.54178) |
| 2Θ range for data collection/° | 6.28 to 154.348 |
| Index ranges | −7 ≤ h ≤ 10, −31 ≤ k ≤ 33, −18 ≤ l ≤ 18 |
| Reflections collected | 52633 |
| Independent reflections | 12237 [R$_{int}$ = 0.0753, R$_{sigma}$ = 0.0723] |
| Data/restraints/parameters | 12237/1/752 |
| S | 1.029 |
| Final R indexes [F$^2$ > 2σ (F$^2$)] | R$_1$ = 0.0512, wR$_2$ = 0.1300 |
| Final R indexes [all data] | R$_1$ = 0.0552, wR$_2$ = 0.1325 |
| Δρmax, Δρmin/e Å$^{-3}$, | 0.39/−0.44 |
| Flack Parameter | 0.017(1) |

R$_1$ = (Σ |F$_o$| − |F$_c$|)/Σ |F$_o$|); wR$_2$ = {Σ [w(F$_o^2$ − F$_c^2$)$^2$]/Σ [w(F$_o^2$)$^2$]}$^{1/2}$;
S = {Σ [w(F$_o^2$ − F$^2$)$^2$]/(n − p)}$^{1/2}$

TABLE 22

Fractional Atomic Coordinates (×104) and Equivalent Isotropic Displacement Parameters (Å2 × 103) for MTP-131 tosylate, Pattern 2. Ueq is defined as ⅓ of the trace of the orthogonalised UIJ tensor.

| Atom | x | y | z | U(eq) |
|---|---|---|---|---|
| C1 | 9503(5) | 6963.4(17) | 3816(3) | 28.9(3) |
| N1 | 10146(5) | 7079.7(16) | 4732(3) | 32.5(8) |
| O1 | 5861(4) | 4987.9(11) | 2263(2) | 27.2(6) |
| C2 | 6822(5) | 6839.7(16) | 2510(3) | 29.4(8) |
| N2 | 10557(5) | 6828.9(15) | 3292(3) | 32.2(8) |
| O2 | 1490(4) | 4398.6(13) | 6762(2) | 31.9(6) |
| C3 | 6619(5) | 6281.6(15) | 2338(3) | 24.8(7) |
| N3 | 7784(5) | 6976.1(15) | 3469(3) | 30.9(7) |
| O3 | −168(3) | 5093.1(12) | 1954(2) | 29.8(6) |
| S3 | 3799.0(11) | 4395.8(3) | 9238.4(7) | 24.6(2) |
| C4 | 5260(5) | 6186.8(14) | 1413(3) | 23.2(7) |
| N4 | 6703(4) | 5467.6(13) | 854(2) | 22.5(6) |
| O4 | 141(4) | 3549.1(11) | 3848(2) | 27.0(6) |
| C5 | 5087(4) | 5642.4(14) | 1102(3) | 21.0(7) |
| N5 | 3228(4) | 5358.2(12) | 2070(2) | 22.3(6) |
| O5 | −5744(3) | 4048.4(11) | 3720(2) | 28.1(6) |
| C6 | 4764(5) | 5291.5(14) | 1873(3) | 20.5(7) |
| N6 | 866(4) | 4395.0(12) | 2787(2) | 20.6(6) |
| C7 | 2779(4) | 5102.6(14) | 2860(3) | 20.2(7) |
| N7 | −2201(4) | 4333.4(16) | −1288(3) | 32.6(8) |
| C8 | 2689(5) | 5482.9(14) | 3642(3) | 22.9(7) |
| N8 | −2519(4) | 3897.3(13) | 3628(2) | 23.0(6) |
| C9 | 2389(5) | 5226.8(14) | 4514(3) | 22.1(7) |
| N9 | −6023(4) | 3256.3(13) | 4168(3) | 28.5(7) |
| C10 | 3792(5) | 5021.4(15) | 5187(3) | 23.9(7) |
| C11 | 3525(5) | 4748.9(16) | 5951(3) | 26.2(8) |
| C12 | 1855(5) | 4678.8(16) | 6043(3) | 25.4(8) |
| O12 | 4092(4) | 4220.7(12) | 8334(2) | 29.6(6) |
| C13 | 454(5) | 4900.0(16) | 5405(3) | 24.9(7) |
| O13 | 5290(4) | 4664.6(12) | 9799(2) | 34.2(7) |
| C14 | 713(5) | 5182.0(15) | 4650(3) | 23.8(7) |
| O14 | 2180(4) | 4669.7(13) | 9101(3) | 36.3(7) |
| C15 | 5625(5) | 5107.5(17) | 5114(3) | 27.9(8) |
| C16 | −834(5) | 5451.4(18) | 4027(3) | 31.5(9) |
| O16 | −430(5) | 5146.7(14) | 9754(3) | 40.7(8) |
| C17 | 1016(5) | 4856.4(14) | 2487(3) | 21.2(7) |
| C18 | −797(4) | 4135.8(14) | 2564(3) | 20.3(7) |
| C19 | −1000(5) | 3770.2(15) | 1729(3) | 24.6(7) |
| C20 | −941(5) | 4024.7(15) | 600(3) | 24.8(7) |
| C21 | −1383(6) | 3669.7(16) | −44(3) | 29.1(8) |
| C22 | −1094(5) | 3887.9(17) | −951(3) | 29.8(8) |
| C23 | −976(5) | 3838.9(15) | 3428(3) | 22.6(7) |
| C24 | −3108(5) | 3596.7(15) | 4322(3) | 22.0(7) |
| C25 | −5095(5) | 3647.4(15) | 4042(3) | 21.5(7) |
| C26 | −2348(5) | 3798.9(16) | 5343(3) | 27.3(8) |
| C27 | −2746(6) | 3489.8(16) | 6123(3) | 31.7(9) |
| C28 | −1527(10) | 3160(2) | 6653(4) | 52.8(15) |
| C29 | −2004(15) | 2876(2) | 7392(4) | 80(3) |
| C30 | −3581(16) | 2929(3) | 7574(5) | 83(3) |
| C31 | −4723(12) | 3246(2) | 7061(5) | 75(3) |
| C32 | −4336(8) | 3526(2) | 6341(4) | 43.7(12) |
| C47 | 3629(5) | 3858.2(16) | 9898(3) | 25.6(8) |
| C48 | 3889(6) | 3895.8(17) | 10876(3) | 30.6(8) |
| C49 | 3674(6) | 3477.5(19) | 11391(3) | 36(1) |
| C50 | 3206(6) | 3020.3(18) | 10950(4) | 35.8(10) |
| C51 | 2967(7) | 2988.3(18) | 9969(4) | 38.7(10) |
| C52 | 3179(6) | 3406.8(17) | 9437(3) | 32.5(9) |
| C53 | 2946(8) | 2574(2) | 11523(5) | 52.3(15) |
| S1 | 14930.6(12) | 6993.9(3) | 5046.6(7) | 25.4(2) |
| O6 | 13742(4) | 7393.6(11) | 5151(2) | 28.8(6) |
| O7 | 16715(4) | 7174.5(12) | 5203(2) | 32.3(6) |
| O8 | 14317(4) | 6722.6(12) | 4148(2) | 32.8(6) |
| C33 | 14888(5) | 6578.1(14) | 5970(3) | 25.9(8) |
| C34 | 16126(6) | 6614.0(17) | 6840(3) | 31.1(9) |
| C35 | 15932(6) | 6325.9(18) | 7602(3) | 35.8(10) |
| C36 | 14542(6) | 6000.2(18) | 7501(3) | 35.0(9) |
| C37 | 13340(6) | 6989.2(16) | 6628(4) | 33.5(9) |
| C38 | 13491(5) | 6253.2(16) | 5858(3) | 29.4(8) |
| C39 | 14376(9) | 5893(2) | 8341(4) | 53.5(14) |
| S2 | −132.1(12) | 6467.2(4) | 562.3(8) | 30.6(2) |
| O9 | 985(5) | 6038.4(19) | 890(4) | 71/(17) |
| O10 | −54(8) | 6850.6(19) | 1273(5) | 68.9(16) |
| O11 | −1891(4) | 6304.2(13) | 117(2) | 33.5(7) |
| C40 | 664(5) | 6738.5(14) | −343(3) | 24.7(8) |
| C41 | 1520(6) | 7192.3(17) | −208(3) | 29.9(8) |
| C42 | 2088(6) | 7403.2(18) | −947(4) | 33.5(9) |
| C43 | 1786(6) | 7173.7(18) | −1833(4) | 33.2(9) |
| C44 | 964(6) | 6716(2) | −1952(4) | 39.6(11) |
| C45 | 418(6) | 6497.1(18) | −1218(4) | 35.8(10) |
| C46 | 2282(7) | 7421(2) | −2658(4) | 46.3(12) |
| O15 | −1385(4) | 4777.5(13) | −2797(2) | 32.7(6) |
| C54 | −1062(8) | 5297(2) | −2634(4) | 45 1(11) |

TABLE 23

Anisotropic Displacement Parameters (Å2 × 103) for MTP-131 Tosylate, Pattern 2. The Anisotropic displacement factor exponent takes the form: $-2\pi2$ [h2a*2U11 + 2hka*b*U12+].

| Atom | $U_{11}$ | $U_{22}$ | $U_{33}$ | $U_{23}$ | $U_{13}$ | $U_{12}$ |
|---|---|---|---|---|---|---|
| C1 | 27.4 (19) | 26 (2) | 34 (2) | 1.1 (16) | 9.3 (16) | −3.6 (16) |
| N1 | 24.8 (16) | 41 (2) | 32.6 (18) | −4.5 (15) | 9.5 (14) | −4.1 (14) |
| O1 | 19.6 (12) | 27.7 (15) | 36.0 (15) | 8.5 (12) | 10.1 (11) | 5.5 (10) |
| C2 | 28 (2) | 22 (2) | 37 (2) | −1.8 (16) | 6.1 (16) | −0.4 (15) |
| N2 | 26.4 (17) | 38 (2) | 34.0 (18) | −3.3 (15) | 10.4 (14) | −6.0 (14) |
| O2 | 27.1 (14) | 38.3 (17) | 30.2 (14) | 9.9 (13) | 7.2 (11) | −2.5 (12) |
| C3 | 21.2 (17) | 21.1 (19) | 32.7 (19) | 1.6 (15) | 8.0 (15) | −0.2 (13) |
| N3 | 26.5 (16) | 29.7 (18) | 36.7 (18) | −7.9 (15) | 8.5 (14) | −3.4 (14) |
| O3 | 16.8 (12) | 26.5 (15) | 44.4 (17) | 11.0 (12) | 5.0 (11) | −0.6 (10) |
| S3 | 20.4 (4) | 22.5 (4) | 31.7 (4) | 1.9 (3) | 8.4 (3) | −0.2 (3) |
| C4 | 18.9 (16) | 16.8 (18) | 33.7 (19) | 2.6 (14) | 6.8 (14) | −1.6 (13) |
| N4 | 18.8 (14) | 24.7 (16) | 26.1 (15) | 2.6 (12) | 9.4 (12) | −0.7 (12) |
| O4 | 21.0 (13) | 26.6 (15) | 35.0 (15) | 7.7 (11) | 9.8 (11) | 1.9 (10) |
| C5 | 15.4 (15) | 19.8 (18) | 28.1 (18) | 1.4 (14) | 5.8 (13) | −1.8 (12) |
| N5 | 15.9 (14) | 19.5 (15) | 32.6 (17) | 6.3 (12) | 8.2 (12) | 0.9 (11) |
| O5 | 18.1 (12) | 22.0 (14) | 44.8 (17) | 6.8 (12) | 9.1 (11) | 2.9 (10) |
| C6 | 18.6 (16) | 18.3 (17) | 25.1 (17) | 0.2 (13) | 6.7 (13) | −3.2 (13) |
| N6 | 13.7 (13) | 17.6 (15) | 29.7 (14) | 3.2 (12) | 3.9 (11) | −0.3 (11) |
| C7 | 14.8 (15) | 16.3 (16) | 30.7 (18) | 2.8 (14) | 7.9 (13) | 1.1 (13) |
| N7 | 24.6 (16) | 47 (2) | 28.8 (16) | 2.6 (15) | 10.8 (13) | 0.8 (15) |
| C8 | 18.3 (16) | 19.7 (18) | 30.7 (19) | 1.5 (14) | 6.3 (14) | −1.2 (13) |
| N8 | 16.3 (14) | 21.1 (15) | 33.0 (16) | 4.9 (13) | 9.0 (12) | 1.3 (11) |
| C9 | 18.7 (17) | 19.7 (18) | 29.3 (19) | −0.5 (14) | 8.7 (14) | −1.9 (13) |
| N9 | 18.7 (15) | 21.7 (17) | 46 (2) | 5.6 (14) | 9.4 (14) | −1.0 (12) |
| C10 | 16.6 (17) | 23.2 (19) | 31.9 (19) | −2.1 (15) | 6.2 (14) | −1.3 (13) |
| C11 | 22.0 (18) | 26 (2) | 28.2 (18) | 1.0 (15) | 3.3 (14) | 1.4 (14) |
| C12 | 24.5 (18) | 25.6 (19) | 26.6 (18) | 3.5 (15) | 7.6 (14) | −1.6 (14) |
| O12 | 23.3 (13) | 34.5 (16) | 32.5 (15) | 1.8 (12) | 9.8 (11) | −0.5 (11) |
| C13 | 17.8 (17) | 28 (2) | 29.5 (18) | 3.4 (15) | 7.5 (14) | −1.7 (14) |
| O13 | 36.8 (16) | 27.5 (16) | 38.2 (16) | −3.3 (12) | 9.4 (13) | −11.1 (12) |
| C14 | 15.8 (17) | 24.1 (19) | 31.0 (19) | 1.3 (15) | 5.3 (14) | 0.0 (13) |
| O14 | 29.6 (15) | 31.2 (17) | 53.8 (19) | 11.2 (14) | 21.2 (14) | 10.2 (13) |
| C15 | 17.1 (17) | 31 (2) | 35 (2) | −2.2 (17) | 7.2 (15) | 0.4 (15) |
| C16 | 16.0 (17) | 41 (2) | 38 (2) | 9.6 (18) | 7.2 (15) | 6.0 (16) |
| O16 | 37.0 (17) | 40.7 (19) | 47.0 (19) | −9.1 (15) | 15.4 (15) | 1.6 (14) |
| C17 | 18.0 (16) | 17.7 (18) | 28.7 (18) | 1.9 (14) | 7.4 (14) | −0.5 (13) |
| C18 | 12.5 (15) | 19.0 (17) | 30.1 (18) | 1.2 (14) | 6.6 (13) | −2.0 (12) |
| C19 | 22.3 (17) | 22.8 (19) | 30.0 (19) | −2.1 (15) | 9.0 (14) | −3.7 (14) |
| C20 | 25.3 (18) | 21.5 (19) | 28.1 (18) | −1.6 (15) | 7.8 (14) | −2.0 (14) |
| C21 | 29 (2) | 28 (2) | 32 (2) | −3.8 (16) | 10.0 (16) | −3.4 (16) |
| C22 | 29 (2) | 31 (2) | 32 (2) | −3.4 (16) | 12.5 (16) | −1.2 (16) |
| C23 | 19.0 (17) | 18.5 (18) | 31.7 (19) | 11 (14) | 8.8 (14) | −2.8 (13) |
| C24 | 14.5 (16) | 22.5 (18) | 29.5 (18) | 2.6 (14) | 6.7 (13) | 0.0 (13) |
| O25 | 16.2 (17) | 21.5 (18) | 27.8 (17) | 4.2 (14) | 7.1 (13) | 1.6 (13) |
| O26 | 24.9 (18) | 27 (2) | 30.3 (19) | 2.0 (16) | 7.0 (15) | −2.1 (15) |
| O27 | 45 (2) | 20 (2) | 30 (2) | −1.2 (16) | 8.8 (18) | −2.0 (17) |
| C28 | 87 (4) | 32 (3) | 32 (2) | −2 (2) | 1 (3) | 21 (3) |
| C29 | 174 (9) | 16 (3) | 30 (3) | 4.3 (19) | −7 (4) | 10 (4) |
| C30 | 159 (9) | 54 (4) | 40 (3) | −14 (3) | 36 (5) | −55 (5) |
| O31 | 104 (6) | 89 (6) | 41 (3) | −12 (4) | 35 (4) | −55 (5) |
| C32 | 55 (3) | 44 (3) | 36 (2) | −9 (2) | 20 (2) | −16 (2) |
| C47 | 21.2 (17) | 24.5 (19) | 31.6 (19) | 4.3 (15) | 8.0 (14) | −2.5 (14) |
| C48 | 32 (2) | 28 (2) | 31 (2) | 2.5 (16) | 7.2 (16) | −3.7 (16) |
| C49 | 35 (2) | 37 (3) | 36 (2) | 8.1 (19) | 7.1 (18) | −6.9 (18) |
| C60 | 28 (2) | 31 (2) | 47 (3) | 12.9 (19) | 7.5 (18) | −2.4 (16) |
| C51 | 43 (2) | 20 (2) | 52 (3) | 2.0 (19) | 11 (2) | −4.2 (18) |
| C52 | 38 (2) | 24 (2) | 36 (2) | 0.1 (17) | 11.6 (18) | −5.2 (17) |
| C53 | 49 (3) | 39 (3) | 64 (3) | 23 (3) | 5 (3) | −13 (2) |
| S1 | 23.6 (4) | 20.0 (4) | 34.3 (5) | −2.5 (4) | 10.4 (3) | −1.5 (3) |
| O6 | 25.2 (14) | 17.9 (13) | 44.8 (16) | −1.0 (12) | 11.5 (12) | 1.5 (11) |
| O7 | 25.7 (14) | 30.2 (16) | 44.0 (17) | −3.6 (13) | 14.3 (13) | −6.0 (12) |
| O8 | 36.6 (16) | 29.3 (16) | 32.8 (15) | −6.1 (12) | 9.3 (13) | −2.7 (12) |
| C33 | 27.4 (19) | 17.2 (18) | 35 (2) | −0.7 (15) | 10.8 (16) | 2.5 (14) |
| C34 | 25.9 (19) | 28 (2) | 38 (2) | −2.5 (17) | 5.4 (17) | −1.7 (15) |
| C35 | 37 (2) | 32 (2) | 36 (2) | 1.7 (18) | 4.8 (18) | 1.6 (16) |
| C36 | 40 (2) | 27 (2) | 38 (2) | 6.8 (18) | 8.8 (18) | 3.8 (17) |
| C37 | 36 (2) | 21 (2) | 44 (2) | −0.4 (17) | 10.6 (18) | −3.6 (16) |
| C38 | 29 (2) | 20.8 (19) | 38 (2) | −2.1 (16) | 6.7 (16) | −3.6 (15) |
| C39 | 66 (4) | 47 (3) | 47 (3) | 17 (3) | 12 (3) | −4 (3) |
| S2 | 23.1 (4) | 28.2 (5) | 37.7 (5) | 11.5 (4) | 2.7 (4) | −5.4 (4) |
| O9 | 24.7 (17) | 64 (3) | 118 (4) | 64 (3) | 2 (2) | 4.4 (17) |
| O10 | 117 (4) | 65 (3) | 34.3 (18) | −14.0 (18) | 37 (2) | −54 (3) |
| O11 | 21.5 (13) | 39.0 (18) | 40.5 (17) | 8.4 (13) | 8.9 (12) | −5.8 (12) |
| C40 | 20.2 (17) | 17.4 (18) | 38 (2) | 5.5 (15) | 10.3 (15) | 0.7 (14) |

TABLE 23-continued

Anisotropic Displacement Parameters (Å2 × 103) for MTP-131 Tosylate, Pattern 2. The Anisotropic displacement factor exponent takes the form: −2π2 [h2a*2U11 + 2hka*b*U12+].

| Atom | $U_{11}$ | $U_{22}$ | $U_{33}$ | $U_{23}$ | $U_{13}$ | $U_{12}$ |
|---|---|---|---|---|---|---|
| C41 | 30 (2) | 27 (2) | 34 (2) | 1.4 (16) | 9.4 (16) | −6.1 (16) |
| C42 | 37 (2) | 25 (2) | 42 (2) | 3.6 (18) | 15.4 (18) | −6.4 (17) |
| C43 | 25.4 (19) | 34 (2) | 45 (2) | −0.3 (19) | 18.1 (18) | 3.2 (16) |
| C44 | 38 (2) | 43 (3) | 44 (3) | −13 (2) | 21 (2) | −8 (2) |
| C45 | 34 (2) | 27 (2) | 52 (3) | −9.1 (19) | 22 (2) | −5.7 (17) |
| C46 | 46 (3) | 55 (3) | 47 (3) | 8 (2) | 28 (2) | 3 (2) |
| O15 | 28.2 (14) | 34.7 (17) | 36.4 (16) | 1.9 (13) | 10.5 (12) | 2.2 (12) |
| C54 | 54 (3) | 36 (3) | 45 (3) | −1 (2) | 12 (2) | 0 (2) |

TABLE 24

Bond Lengths for MTP-131 Tosylate, Pattern 2.

| Atom | Atom | Length/A |
|---|---|---|
| C1 | N1 | 1.338(6) |
| C1 | N2 | 1.322(6) |
| C1 | N3 | 1.336(6) |
| O1 | C6 | 1.227(5) |
| C2 | C3 | 1.527(6) |
| C2 | N3 | 1.459(6) |
| O2 | C12 | 1.381(5) |
| C3 | C4 | 1.520(5) |
| O3 | C17 | 1.237(5) |
| S3 | O12 | 1.472(3) |
| S3 | O13 | 1.453(3) |
| S3 | O14 | 1.457(3) |
| S3 | C47 | 1.763(4) |
| C4 | C5 | 1.532(5) |
| N4 | C5 | 1.501(5) |
| O4 | C23 | 1.225(5) |
| C5 | C6 | 1.538(5) |
| N5 | C6 | 1.341(5) |
| N5 | C7 | 1.460(5) |
| O5 | C25 | 1.238(5) |
| N6 | C17 | 1.334(5) |
| N6 | C18 | 1.461(4) |
| C7 | C8 | 1.548(5) |
| C7 | C17 | 1.525(5) |
| N7 | C22 | 1.498(6) |
| C8 | C9 | 1.515(5) |
| N8 | C23 | 1.345(5) |
| N8 | C24 | 1.462(5) |
| C9 | C10 | 1.400(6) |
| C9 | C14 | 1.407(5) |
| N9 | C25 | 1.328(5) |
| C10 | C11 | 1.395(6) |
| C10 | C15 | 1.511(5) |
| C11 | C12 | 1.387(6) |
| C12 | C13 | 1.392(6) |
| C13 | C14 | 1.395(6) |
| C14 | C16 | 1.518(5) |
| C18 | C19 | 1.541(5) |
| C18 | C23 | 1.529(5) |
| C19 | C20 | 1.527(6) |
| C20 | C21 | 1.526(6) |
| C21 | C22 | 1.515(6) |
| C24 | C25 | 1.540(5) |
| C24 | C26 | 1.555(6) |
| C26 | C27 | 1.506(6) |
| C27 | C28 | 1.396(7) |
| C27 | C32 | 1.388(8) |
| C28 | C29 | 1.449(11) |
| C29 | C30 | 1.359(15) |
| C30 | C31 | 1.330(15) |
| C31 | C32 | 1.390(8) |
| C47 | C48 | 1.390(6) |
| C47 | C52 | 1.392(6) |
| C48 | C49 | 1.389(6) |
| C49 | C50 | 1.396(7) |
| C50 | C51 | 1.394(8) |
| C50 | C53 | 1.509(7) |
| C51 | C52 | 1.403(7) |
| S1 | O6 | 1.469(3) |
| S1 | O7 | 1.468(3) |
| S1 | O8 | 1.469(3) |
| S1 | C33 | 1.757(4) |
| C33 | C34 | 1.397(6) |
| C33 | C38 | 1.395(6) |
| C34 | C35 | 1.395(7) |
| C35 | C36 | 1.393(7) |
| C36 | C37 | 1.386(7) |
| C36 | C39 | 1.509(7) |
| C37 | C38 | 1.388(7) |
| S2 | O9 | 1.464(4) |
| S2 | O10 | 1.453(5) |
| S2 | O11 | 1.456(3) |
| S2 | C40 | 1.761(4) |
| C40 | C41 | 1.391(6) |
| C40 | C45 | 1.399(7) |
| C41 | C42 | 1.391(6) |
| C42 | C43 | 1.395(7) |
| C43 | C44 | 1.388(7) |
| C43 | C46 | 1.511(7) |
| C44 | C45 | 1.385(7) |
| O15 | C54 | 1.432(6) |

TABLE 25

Bond Angles for MTP-131 Tosylate, Pattern 2.

| Atom | Atom | Atom | Angle/° |
|---|---|---|---|
| N2 | C1 | N1 | 120.0 (4) |
| N2 | C1 | N3 | 122.2 (4) |
| N3 | C1 | N1 | 117.8 (4) |
| N3 | C2 | C3 | 114.4 (4) |
| C4 | C3 | C2 | 109.4 (3) |
| C1 | N3 | C2 | 126.5 (4) |
| O12 | S3 | C47 | 105.9 (2) |
| O13 | S3 | 12 | 111.59 (18) |
| O13 | S3 | 14 | 113.3 (2) |
| O13 | S3 | C47 | 105.7 (2) |
| O14 | S3 | 12 | 112.1 (2) |
| O14 | S3 | C47 | 107.64 (19) |
| C3 | C4 | C5 | 114.4 (3) |
| C4 | C5 | C6 | 113.2 (3) |
| N4 | C5 | C4 | 110.7 (3) |
| N4 | C5 | C6 | 107.2 (3) |
| C6 | N5 | C7 | 121.8 (3) |
| O1 | C6 | C5 | 121.0 (3) |
| O1 | C6 | N5 | 125.0 (4) |
| N5 | C6 | C5 | 113.9 (3) |
| C17 | N6 | C18 | 121.7 (3) |
| N5 | C7 | C8 | 109.5 (3) |

TABLE 25-continued

Bond Angles for MTP-131 Tosylate, Pattern 2.

| Atom | Atom | Atom | Angle/° |
|---|---|---|---|
| N5 | C7 | C17 | 108.3 (3) |
| C17 | C7 | C8 | 109.8 (3) |
| C9 | C8 | C7 | 111.2 (3) |
| C23 | N8 | C24 | 123.9 (3) |
| C10 | C9 | C8 | 119.8 (3) |
| C10 | C9 | C14 | 119.1 (4) |
| C14 | C9 | C8 | 121.0 (3) |
| C9 | 10 | C15 | 120.4 (4) |
| C11 | 10 | C9 | 120.6 (3) |
| C11 | 10 | C15 | 118.9 (4) |
| C12 | C11 | C10 | 119.7 (4) |
| O2 | C12 | C11 | 122.8 (4) |
| O2 | C12 | C13 | 116.8 (3) |
| C11 | C12 | C13 | 120.4 (4) |
| C12 | C13 | C14 | 120.2 (4) |
| C9 | C14 | C16 | 122.2 (4) |
| C13 | C14 | C9 | 119.7 (4) |
| C13 | C14 | C16 | 118.1 (3) |
| O3 | C17 | N6 | 124.6 (3) |
| O3 | C17 | C7 | 119.1 (3) |
| N6 | C17 | C7 | 116.2 (3) |
| N6 | C18 | C19 | 112.8 (3) |
| N6 | C18 | C23 | 109.7 (3) |
| C23 | C18 | C19 | 107.5 (3) |
| C20 | C19 | C18 | 112.9 (3) |
| C21 | C20 | C19 | 112.2 (3) |
| C22 | C21 | C20 | 113.7 (4) |
| N7 | C22 | C21 | 112.8 (3) |
| O4 | C23 | N8 | 123.9 (4) |
| O4 | C23 | C18 | 122.4 (4) |
| N8 | C23 | C18 | 113.6 (3) |
| N8 | C24 | C25 | 105.0 (3) |
| N8 | C24 | C26 | 110.5 (3) |
| C25 | C24 | C26 | 110.2 (3) |
| O5 | C25 | N9 | 123.5 (3) |
| O5 | C25 | C24 | 118.7 (3) |
| N9 | C25 | C24 | 117.8 (3) |
| C27 | C26 | C24 | 114.9 (3) |
| C28 | C27 | C26 | 121.1 (5) |
| C32 | C27 | C26 | 121.0 (4) |
| C32 | C27 | C28 | 117.9 (5) |
| C27 | C28 | C29 | 118.0 (7) |
| C30 | C29 | C28 | 121.4 (7) |
| C31 | C30 | C29 | 119.6 (6) |
| C30 | C31 | C32 | 121.4 (8) |
| C27 | C32 | C31 | 121.7 (7) |
| C48 | C47 | S3 | 119.1 (3) |
| C48 | C47 | C52 | 120.7 (4) |
| C52 | C47 | S3 | 120.2 (3) |
| C49 | C48 | C47 | 119.2 (4) |
| C48 | C49 | C50 | 121.6 (5) |
| C49 | C50 | C53 | 120.6 (5) |
| C51 | C50 | C49 | 118.4 (4) |
| C51 | C50 | C53 | 120.9 (5) |
| C50 | C51 | C52 | 120.8 (5) |
| C47 | C52 | C51 | 119.3 (4) |
| O6 | S1 | C33 | 104.48 (18) |
| O7 | S1 | O6 | 111.57 (18) |
| O7 | S1 | O8 | 113.15 (19) |
| O7 | S1 | C33 | 107.5 (2) |
| O8 | S1 | O6 | 112.32 (19) |
| O8 | S1 | C33 | 107.2 (2) |
| C34 | C33 | S1 | 120.1 (3) |
| C38 | C33 | S1 | 118.9 (3) |
| C38 | C33 | C34 | 120.6 (4) |
| C35 | C34 | C33 | 119.1 (4) |
| C36 | C35 | C34 | 121.0 (4) |
| C35 | C36 | C39 | 119.5 (5) |
| C37 | C36 | C35 | 118.7 (4) |
| C37 | C36 | C39 | 121.7 (5) |
| C36 | C37 | C38 | 121.7 (4) |
| C37 | C38 | C33 | 118.9 (4) |
| O9 | S2 | C40 | 105.4 (2) |
| O10 | S2 | O9 | 114.7 (4) |
| O10 | S2 | O11 | 113.1 (3) |
| O10 | S2 | C40 | 106.2 (2) |
| O11 | S2 | O9 | 110.2 (2) |
| O11 | S2 | C40 | 106.47 (19) |
| C41 | C40 | S2 | 121.2 (3) |
| C41 | C40 | C45 | 119.2 (4) |
| C45 | C40 | S2 | 119.6 (3) |
| C42 | C41 | C40 | 119.7 (4) |
| C41 | C42 | C43 | 121.3 (4) |
| C42 | C43 | C46 | 121.4 (5) |
| C44 | C43 | C42 | 118.3 (4) |
| C44 | C43 | C46 | 120.3 (5) |
| C45 | C44 | C43 | 121.0 (5) |
| C44 | C45 | C40 | 120.4 (4) |

TABLE 26

Torsion Angles for MTP-131 Tosylate, Pattern 2.

| A | B | C | D | Angle/° |
|---|---|---|---|---|
| N1 | C1 | N3 | C2 | −176.7 (4) |
| C2 | C3 | C4 | C5 | 173.3 (3) |
| N2 | C1 | N3 | C2 | 1.5 (7) |
| O2 | C12 | C13 | C14 | −178.9 (4) |
| C3 | C2 | N3 | C1 | 77.9 (6) |
| C3 | C4 | C5 | N4 | −66.2 (4) |
| C3 | C4 | C5 | C6 | 54.2 (4) |
| N3 | C2 | C3 | C4 | 166.6 (3) |
| S3 | C47 | C48 | C49 | 177.0 (3) |
| S3 | C47 | C52 | C51 | −176.9 (4) |
| C4 | C5 | C6 | O1 | −112.4 (4) |
| C4 | C5 | C6 | N5 | 66.6 (4) |
| N4 | C5 | C6 | O1 | 10.0 (5) |
| N4 | C5 | C6 | N5 | −171.0 (3) |
| N5 | C7 | C8 | C9 | −174.8 (3) |
| N5 | C7 | C17 | O3 | −44.7 (4) |
| N5 | C7 | C17 | N6 | 136.6 (3) |
| C6 | N5 | C7 | C8 | 111.1 (4) |
| C6 | N5 | C7 | C17 | −129.3 (4) |
| N6 | C18 | C19 | C20 | −61.9 (4) |
| N6 | C18 | C23 | O4 | −51.9 (5) |
| N6 | C18 | C23 | N8 | 133.2 (3) |
| C7 | N5 | C6 | O1 | 6.6 (6) |
| C7 | N5 | C6 | C5 | −172.4 (3) |
| C7 | C8 | C9 | C10 | 82.5 (4) |
| C7 | C8 | C9 | C14 | −96.1 (4) |
| C8 | C7 | C17 | O3 | 74.8 (5) |
| C8 | C7 | C17 | N6 | −103.9 (4) |
| C8 | C9 | C10 | C11 | −174.7 (4) |
| C8 | C9 | C10 | C15 | 7.6 (6) |
| C8 | C9 | C14 | C13 | 173.3 (4) |
| C8 | C9 | C14 | C16 | −9.6 (6) |
| N8 | C24 | C25 | O5 | −35.1 (5) |
| N8 | C24 | C25 | N9 | 145.4 (4) |
| N8 | C24 | C26 | C27 | −174.9 (3) |
| C9 | C10 | C11 | C12 | 0.3 (6) |
| C10 | C9 | C14 | C13 | −5.3 (6) |
| C10 | C9 | C14 | C16 | 171.7 (4) |
| C10 | C11 | C12 | O2 | 177.6 (4) |
| C10 | C11 | C12 | C13 | −3.4 (6) |
| C11 | C12 | C13 | C14 | 2.0 (6) |
| C12 | C13 | C14 | C9 | 2.4 (6) |
| C12 | C13 | C14 | C16 | −174.8 (4) |
| O12 | S3 | C47 | C48 | 160.1 (3) |
| O12 | S3 | C47 | C52 | −22.2 (4) |
| O12 | S3 | C47 | C48 | 41.5 (4) |
| O12 | S3 | C47 | C52 | −140.7 (4) |
| C14 | C9 | C10 | C11 | 4.0 (6) |
| C14 | C9 | C10 | C15 | −173.8 (4) |
| O14 | S3 | C47 | C48 | −79.8 (4) |
| O14 | S3 | C47 | C52 | 97.9 (4) |
| C15 | C10 | C11 | C12 | 178.1 (4) |
| C17 | N6 | C18 | C19 | 99.9 (4) |
| C17 | N6 | C18 | C23 | −140.2 (4) |

TABLE 26-continued

Torsion Angles for MTP-131 Tosylate, Pattern 2.

| A | B | C | D | Angle/° |
|---|---|---|---|---|
| C17 | C7 | C8 | C9 | 66.4 (4) |
| C18 | N6 | C17 | O3 | −5.0 (6) |
| C18 | N6 | C17 | C7 | 173.6 (3) |
| C18 | C19 | C20 | C21 | −172.4 (3) |
| C19 | C18 | C23 | O4 | 71.2 (5) |
| C19 | C18 | C23 | N8 | −103.7 (4) |
| C19 | C20 | C21 | C22 | −171.8 (3) |
| C20 | C21 | C22 | N7 | −61.7 (5) |
| C23 | N8 | C24 | C25 | −158.7 (4) |
| C23 | N8 | C24 | C26 | 82.4 (5) |
| C23 | C18 | C19 | C20 | 177.0 (3) |
| C24 | N8 | C23 | O4 | −4.8 (6) |
| C24 | N8 | C23 | C18 | 170.1 (3) |
| C24 | C26 | C27 | C28 | 100.0 (5) |
| C24 | C26 | C27 | C32 | −80.4 (5) |
| C25 | C24 | C26 | C27 | 69.4 (5) |
| C26 | C24 | C25 | O5 | 83.9 (4) |
| C26 | C24 | C25 | N9 | −95.6 (4) |
| C26 | C27 | C28 | C29 | 179.9 (4) |
| C26 | C27 | C32 | C31 | −179.7 (5) |
| C27 | C28 | C29 | C30 | −0.6 (9) |
| C28 | C27 | C32 | C31 | −0.1 (8) |
| C28 | C29 | C30 | C31 | 0.5 (10) |
| C29 | C30 | C31 | C32 | −0.2 (10) |
| C30 | C31 | C32 | C27 | 0.0 (10) |
| C32 | C27 | C28 | C29 | 0.3 (7) |
| C47 | C48 | C49 | C50 | 0.0 (7) |
| C48 | C47 | C52 | C51 | 0.8 (7) |
| C48 | C49 | C50 | C51 | 0.6 (7) |
| C48 | C49 | C50 | C53 | −178.8 (5) |
| C49 | C50 | C51 | C52 | −0.5 (7) |
| C50 | C51 | C52 | C47 | −0.1 (7) |
| C52 | C47 | C48 | C49 | −0.7 (7) |
| C53 | C50 | C51 | C52 | 178.8 (5) |
| S1 | C33 | C34 | C35 | 171.4 (3) |
| S1 | C33 | C38 | C37 | −171.9 (3) |
| O6 | S1 | C33 | C34 | −93.9 (4) |
| O6 | S1 | C33 | C38 | 78.7 (4) |
| O7 | S1 | C33 | C34 | 24.8 (4) |
| O7 | S1 | C33 | C38 | −162.6 (3) |
| O8 | S1 | C33 | C34 | 146.7 (3) |
| O8 | S1 | C33 | C38 | −40.7 (4) |
| C33 | C34 | C35 | C36 | 1.0 (7) |
| C34 | C33 | C38 | C37 | 0.7 (6) |
| C34 | C35 | C36 | C37 | −0.5 (7) |
| C34 | C35 | C36 | C39 | 179.8 (5) |
| C35 | C36 | C37 | C38 | 0.0 (7) |
| C36 | C37 | C38 | C33 | −0.1 (7) |
| C38 | C33 | C34 | C35 | −1.1 (6) |
| C39 | C36 | C37 | C38 | 179.7 (5) |
| S2 | C40 | C41 | C42 | −178.1 (4) |
| S2 | C40 | C45 | C44 | 177.0 (4) |
| O9 | S2 | C40 | C41 | −109.5 (4) |
| O9 | S2 | C40 | C45 | 71.2 (4) |
| O10 | S2 | C40 | C41 | 12.7 (5) |
| O10 | S2 | C40 | C45 | −166.7 (4) |
| O11 | S2 | C40 | C41 | 133.5 (4) |
| O11 | S2 | C40 | C45 | −45.8 (4) |
| C40 | C41 | C42 | C43 | 1.4 (7) |
| C41 | C40 | C45 | C44 | −2.4 (7) |
| C41 | C42 | C43 | C44 | −2.7 (7) |
| C41 | C42 | C43 | C46 | 175.3 (5) |
| C42 | C43 | C44 | C45 | 1.5 (7) |
| C43 | C44 | C45 | C40 | 1.0 (8) |
| C45 | C40 | C41 | C42 | 1.2 (6) |
| C46 | C43 | C44 | C45 | −176.5 (5) |

TABLE 27

Hydrogen Atom Coordinates (Å × 10⁴) and Isotropic Displacement Parameters (Å² × 10³) for MTP-131 Tosylate, Pattern 2.

| Atom | x | y | z | U(eq) |
|---|---|---|---|---|
| H1A | 11245.32 | 7066.87 | 4979.6 | 39 |
| H1B | 9460.92 | 7167.19 | 5072.65 | 39 |
| H2A | 7407.71 | 6978.75 | 2061.35 | 35 |
| H2B | 5678.96 | 6988.1 | 2381.78 | 35 |
| H2C | 10141.74 | 6745.9 | 2707.92 | 39 |
| H2D | 11658.15 | 6824.44 | 3535.93 | 39 |
| H2 | 2357.75 | 4379.12 | 7205.77 | 48 |
| H3A | 7717.66 | 6139.45 | 2303.32 | 30 |
| H3B | 6270.67 | 6125.63 | 2860.46 | 30 |
| H3 | 7185.9 | 7074.64 | 3848.91 | 37 |
| H4A | 5545.5 | 6382.18 | 914.69 | 28 |
| H4B | 4146.6 | 6301.27 | 1483.26 | 28 |
| H4C | 6448.25 | 5212.88 | 453.9 | 27 |
| H4D | 7475.93 | 5372.51 | 1380.22 | 27 |
| H4E | 7141.43 | 5713.7 | 581.17 | 27 |
| H5 | 4114.12 | 5612.97 | 537.26 | 25 |
| H5A | 2487.02 | 5556.72 | 1722.91 | 27 |
| H6 | 1770.53 | 4246.24 | 3120.35 | 25 |
| H7 | 3655.23 | 4850.32 | 3119.99 | 24 |
| H7A | −1943.9 | 4457.65 | −1801.68 | 39 |
| H7B | −2005.94 | 4561.59 | −831.16 | 39 |
| H7C | −3312.76 | 4245.65 | −1431.11 | 39 |
| H8A | 3763.61 | 5668.69 | 3818.25 | 27 |
| H8B | 1753.94 | 5715.13 | 3396.7 | 27 |
| H8 | −3200.02 | 4124.91 | 3330.78 | 28 |
| H9A | −7135.56 | 3273.76 | 4023.6 | 34 |
| H9B | −5511.79 | 2985.59 | 4394.76 | 34 |
| H11 | 4463.15 | 4614.87 | 6397.35 | 31 |
| H13 | −658.63 | 4859.62 | 5483.54 | 30 |
| H15A | 5757.19 | 4973.63 | 4525.77 | 42 |
| H15B | 6420.71 | 4946.46 | 5635.22 | 42 |
| H15C | 5860.02 | 5456.96 | 5136.08 | 42 |
| H16A | −543.84 | 5793.7 | 3971.44 | 47 |
| H16B | −1797.68 | 5428.73 | 4306.7 | 47 |
| H16C | −1138.7 | 5302.18 | 3407.42 | 47 |
| H16D | −66.12 | 5377.61 | 10152.89 | 61 |
| H16E | −132.02 | 5207.14 | 9244.45 | 61 |
| H18 | −1732.19 | 4381.06 | 2403.6 | 24 |
| H19A | −80.45 | 3525.52 | 1887.97 | 30 |
| H19B | −2094.76 | 3596.94 | 1637.67 | 30 |
| H20A | −1756.24 | 4298.51 | 681.83 | 30 |
| H20B | 208.5 | 4159.53 | 861.33 | 30 |
| H21A | −680.52 | 3373.29 | 115.92 | 35 |
| H21B | −2587.52 | 3571.84 | −157.42 | 35 |
| H22A | 115.08 | 3980.68 | −843.57 | 36 |
| H22B | −1340.77 | 3636.77 | −1444.2 | 36 |
| H24 | −2772.96 | 3249.33 | 4280.77 | 26 |
| H26A | −1099.65 | 3824.01 | 5454.71 | 33 |
| H26B | −2792.63 | 4130.95 | 5380.63 | 33 |
| H28 | −441.83 | 3124.52 | 6535.07 | 63 |
| H29 | −1213.38 | 2652.38 | 7749.48 | 96 |
| H30 | −3861.13 | 2745.33 | 8054.93 | 99 |
| H31 | −5802.4 | 3279.66 | 7186.87 | 90 |
| H32 | −5163.73 | 3744.07 | 5996.13 | 52 |
| H48 | 4201.74 | 4197.16 | 11182.46 | 37 |
| H49 | 3847.4 | 3502.52 | 12046.16 | 43 |
| H51 | 2664.51 | 2686.16 | 9664.29 | 46 |
| H52 | 3020.91 | 3382.69 | 8783.17 | 39 |
| H53A | 3576.36 | 2618.08 | 12173.34 | 78 |
| H53B | 3360.44 | 2282.36 | 11271.36 | 78 |
| H53C | 1735.19 | 2535.85 | 11487.56 | 78 |
| H34 | 17066.6 | 6826.98 | 6909.77 | 37 |
| H35 | 16742.25 | 6351.6 | 8185.52 | 43 |
| H37 | 12408.74 | 5752.62 | 6556.43 | 40 |
| H38 | 12673.65 | 6227.11 | 5276.34 | 35 |
| H39A | 14220.34 | 5908.42 | 8837.68 | 80 |
| H39B | 15406.58 | 5499.26 | 8568.07 | 80 |
| H39C | 13393.65 | 5476.6 | 8149.6 | 80 |
| H41 | 1711.37 | 7354.12 | 6 | 36 |
| H42 | 2681.46 | 7703.19 | −848.11 | 40 |
| H44 | 776.35 | 6553.74 | −2533.29 | 47 |
| H45 | −114.62 | 6187.87 | −1306.81 | 43 |
| H46A | 1257.07 | 7536.27 | −3107.11 | 69 |
| H46B | 2872.15 | 7186.42 | −2960.85 | 69 |

TABLE 27-continued

Hydrogen Atom Coordinates (Å × 104) and Isotropic Displacement Parameters (Å2 × 103) for MTP-131 Tosylate, Pattern 2.

| Atom | x | y | z | U(eq) |
|---|---|---|---|---|
| H46C | 3033.29 | 7696.61 | −2429.21 | 69 |
| H15 | −524.45 | 4644.58 | −2896.74 | 49 |
| H54A | −1102.04 | 5458.59 | −3226.65 | 68 |
| H54B | 60.96 | 5343.02 | −2207.44 | 68 |
| H54C | −1929.74 | 5436.02 | −2359.74 | 68 |

TABLE 28

MTP-131 tosylate, Pattern 2 simulated XRPD 2θ diffractogram.

| No. | Pos. [°2θ] | FWHM | d-spacing [Å] | Height [cts] | Area [cts*°2θ] | Relative Intensity [%] |
|---|---|---|---|---|---|---|
| 1 | 6.5499 | 0.120 | 1361.24 | 13.4840 | 8507.75 | 84.60 |
| 2 | 7.0786 | 0.096 | 680.42 | 12.4779 | 5315.76 | 52.86 |
| 3 | 9.0752 | 0.096 | 328.28 | 9.7367 | 2564.66 | 25.50 |
| 4 | 11.5768 | 0.096 | 294.80 | 7.6377 | 2303.15 | 22.90 |
| 5 | 11.9091 | 0.072 | 232.29 | 7.4253 | 2419.71 | 24.06 |
| 6 | 12.0299 | 0.096 | 541.85 | 7.3510 | 4233.19 | 42.09 |
| 7 | 12.5679 | 0.120 | 248.93 | 7.0375 | 1555.79 | 15.47 |
| 8 | 13.1228 | 0.096 | 821.13 | 6.7412 | 6415.1 | 63.79 |
| 9 | 13.3092 | 0.096 | 698.76 | 6.6472 | 5459.09 | 54.28 |
| 10 | 14.1871 | 0.096 | 131.66 | 6.2377 | 1028.61 | 10.23 |
| 11 | 14.4172 | 0.072 | 266.65 | 6.1387 | 2777.57 | 27.62 |
| 12 | 14.5545 | 0.096 | 365.94 | 6.0811 | 2858.91 | 28.43 |
| 13 | 14.7572 | 0.144 | 251.09 | 5.9981 | 1307.76 | 13.00 |
| 14 | 15.1094 | 0.120 | 592.42 | 5.8590 | 3702.59 | 36.82 |
| 15 | 15.8496 | 0.096 | 1217.01 | 5.5870 | 9507.91 | 94.54 |
| 16 | 15.9777 | 0.072 | 830.34 | 5.5425 | 8649.42 | 86.01 |
| 17 | 17.4741 | 0.120 | 1497.64 | 5.0711 | 9360.24 | 93.08 |
| 18 | 17.7285 | 0.072 | 232.80 | 4.9989 | 2425.04 | 24.11 |
| 19 | 19.5391 | 0.096 | 1024.46 | 4.5396 | 8003.59 | 79.59 |
| 20 | 19.7411 | 0.096 | 1016.14 | 4.4936 | 7938.61 | 78.94 |
| 21 | 20.0464 | 0.072 | 205.14 | 4.4258 | 2136.84 | 21.25 |
| 22 | 20.1613 | 0.144 | 479.44 | 4.4009 | 2497.07 | 24.83 |
| 23 | 20.5588 | 0.072 | 191.56 | 4.3167 | 1995.47 | 19.84 |
| 24 | 20.7283 | 0.120 | 924.72 | 4.2817 | 5779.52 | 57.47 |
| 25 | 21.3456 | 0.096 | 910.95 | 4.1593 | 7116.77 | 70.77 |
| 26 | 22.1097 | 0.120 | 304.25 | 4.0172 | 1901.53 | 18.91 |
| 27 | 22.5050 | 0.096 | 391.10 | 3.9476 | 3055.44 | 30.38 |
| 28 | 22.9420 | 0.096 | 506.23 | 3.8734 | 3954.95 | 39.33 |
| 29 | 23.2455 | 0.120 | 1609.04 | 3.8235 | 10056.52 | 100.00 |
| 30 | 23.4775 | 0.120 | 365.65 | 3.7862 | 2285.33 | 22.72 |
| 31 | 23.9349 | 0.120 | 1080.26 | 3.7149 | 6751.62 | 67.14 |
| 32 | 24.3856 | 0.096 | 331.44 | 3.6472 | 2589.41 | 25.75 |
| 33 | 24.5609 | 0.096 | 259.52 | 3.6216 | 2027.48 | 20.16 |
| 34 | 25.1486 | 0.072 | 167.93 | 3.5383 | 1749.28 | 17.39 |
| 35 | 25.2940 | 0.096 | 295.35 | 3.5183 | 2307.4 | 22.94 |
| 36 | 25.5145 | 0.096 | 247.46 | 3.4883 | 1933.3 | 19.22 |
| 37 | 25.6168 | 0.072 | 185.57 | 3.4747 | 1933.05 | 19.22 |
| 38 | 25.8367 | 0.096 | 349.62 | 3.4456 | 2731.41 | 27.16 |
| 39 | 26.1158 | 0.144 | 208.44 | 3.4094 | 1085.62 | 10.80 |
| 40 | 26.3529 | 0.096 | 210.87 | 3.3792 | 1647.39 | 16.38 |
| 41 | 26.5878 | 0.096 | 163.87 | 3.3499 | 1280.27 | 12.73 |
| 42 | 26.8797 | 0.096 | 163.85 | 3.3142 | 1280.09 | 12.73 |
| 43 | 27.7376 | 0.072 | 105.35 | 3.2136 | 1097.43 | 10.91 |
| 44 | 28.4171 | 0.072 | 123.79 | 3.1383 | 1289.49 | 12.82 |
| 45 | 28.5966 | 0.096 | 411.07 | 3.1190 | 3211.5 | 31.93 |
| 46 | 28.9173 | 0.096 | 172.59 | 3.0851 | 1348.36 | 13.41 |
| 47 | 29.8379 | 0.072 | 153.78 | 2.9920 | 1601.87 | 15.93 |

What is claimed is:

1. A crystalline form of a mesylate salt of Compound I,

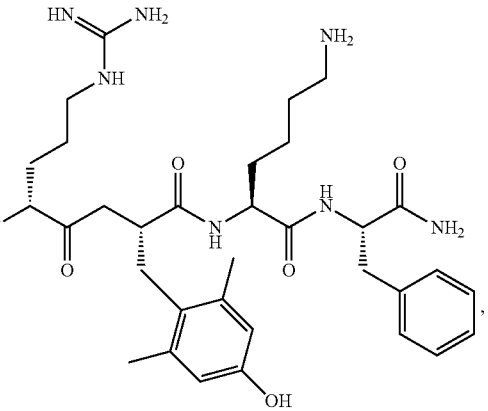

(I)

wherein said crystalline form has characteristic peaks in its XRPD pattern at values of two theta (° 2θ) of: 6.0, 10.4, 11.0, 12.0, 14.9, 19.3, 20.4, and 21.4.

2. The crystalline form of claim 1, wherein said crystalline form has characteristic peaks in its XRPD pattern at values of two theta (° 2θ) of: 6.0, 10.4, 11.0, 12.0, 14.9, 15.7, 18.8, 19.3, 20.4, 20.8, 21.2, 21.4, 21.6, 22.0, 22.5, 22.9, 25.9, and 26.4.

3. A crystalline form of a mesylate salt of Compound I,

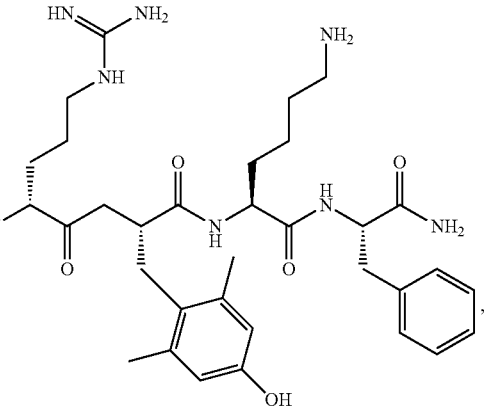

(I)

wherein said crystalline form has characteristic peaks in its XRPD pattern at values of two theta (° 2θ) of: 3.2, 4.3, 6.0, 12.8, 17.5, 18.9, 20.6, 21.4, and 22.7.

4. The crystalline form of claim 3, wherein said crystalline form has characteristic peaks in its XRPD pattern at values of two theta (° 2θ) of: 3.2, 4.3, 6.0, 12.0, 12.4, 12.8, 14.6, 15.8, 15.9, 17.5, 18.4, 18.9, 19.4, 19.8, 20.1, 20.6, 21.4, 22.7, 23.2, 23.8, 24.8, 25.4, and 26.1.

5. A composition, comprising a crystalline form of claim 1.

6. A process for making a pharmaceutical composition comprising Compound I,
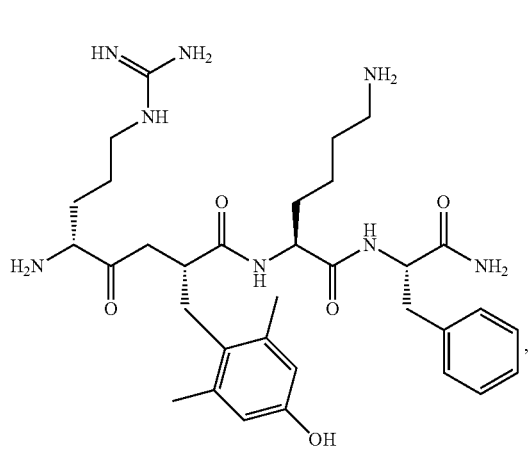
comprising dissolving a crystalline form of claim 1.
7. A composition, comprising a crystalline form of claim 3.
8. A process for making a pharmaceutical composition comprising Compound I,
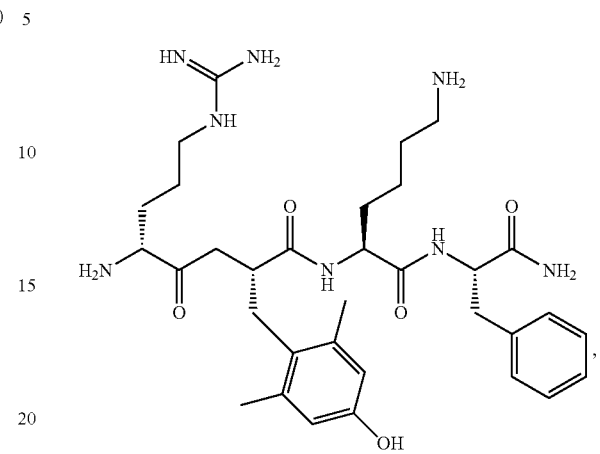
comprising dissolving a crystalline form of claim 3.
* * * * *

UNITED STATES PATENT AND TRADEMARK OFFICE
CERTIFICATE OF CORRECTION

Page 1 of 4

PATENT NO.         : 11,555,053 B2
APPLICATION NO.    : 16/866164
DATED              : January 17, 2023
INVENTOR(S)        : Scott M. Duncan et al.

It is certified that error appears in the above-identified patent and that said Letters Patent is hereby corrected as shown below:

In the Specification

At Column 3, Lines 5-22:

"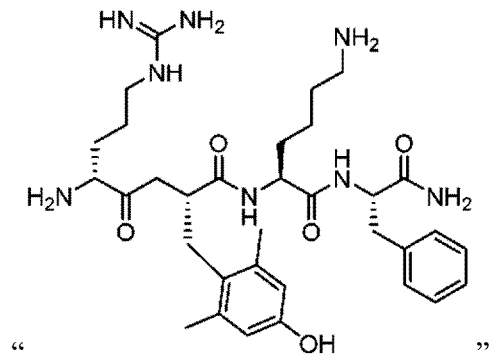"

Should read:

--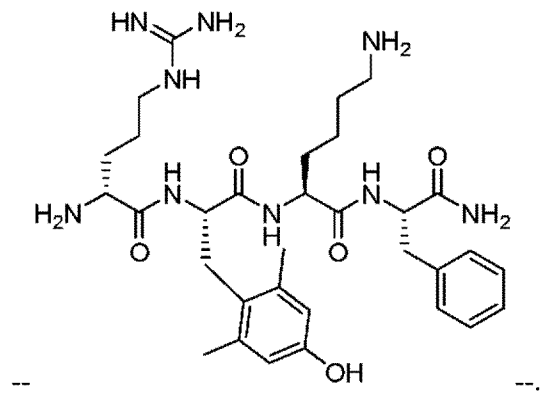--.

Signed and Sealed this
First Day of August, 2023

Katherine Kelly Vidal
*Director of the United States Patent and Trademark Office*

CERTIFICATE OF CORRECTION (continued)
U.S. Pat. No. 11,555,053 B2

In the Claims

In Claim 1, at Column 64, Lines 5-23:

"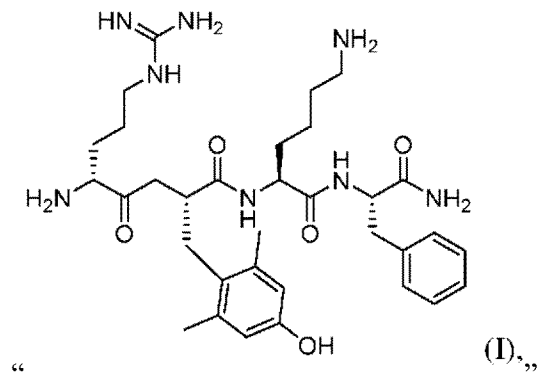

Should read:

--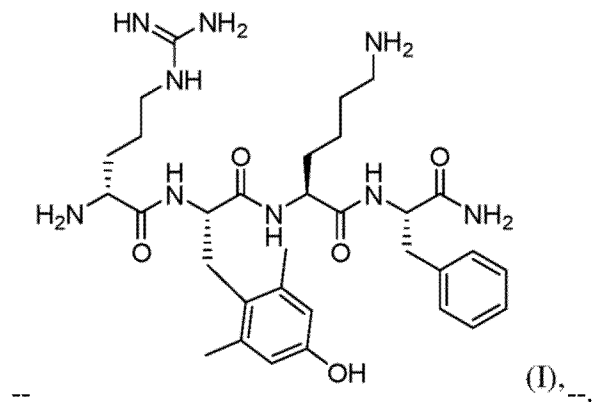--.

In Claim 3, at Column 64, Lines 37-53:

"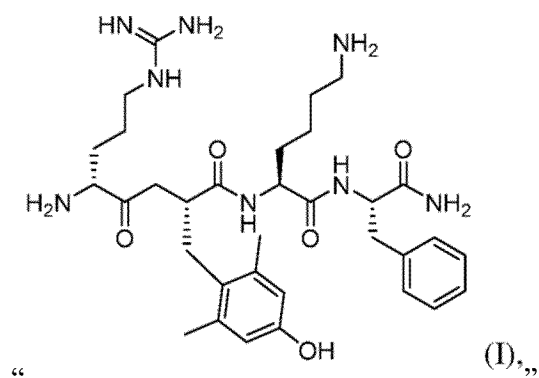

Should read:
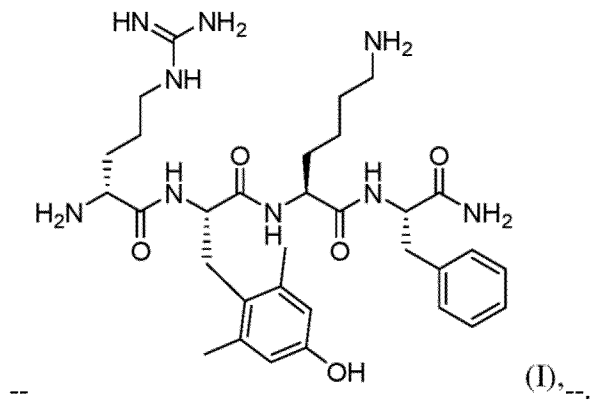
-- (I), --.
In Claim 6, at Column 65, Lines 5-21:
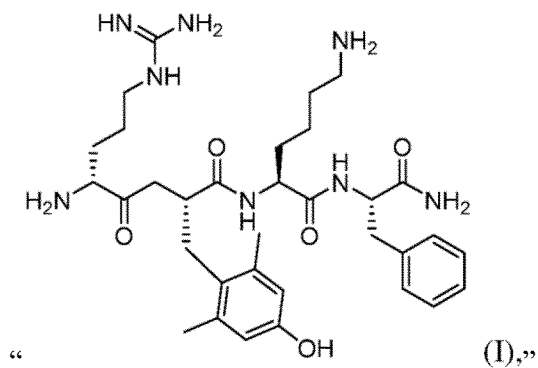
" (I),"
Should read:
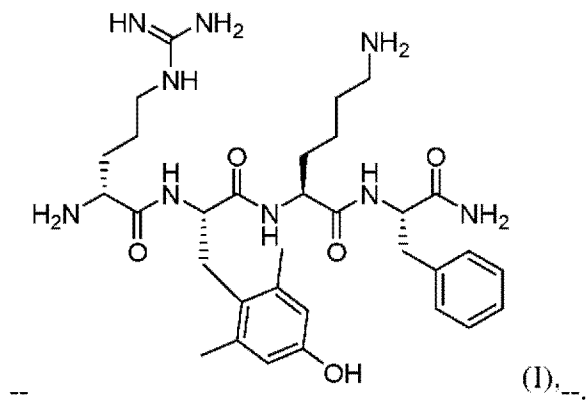
-- (I), --.

CERTIFICATE OF CORRECTION (continued)
U.S. Pat. No. 11,555,053 B2

In Claim 8, at Column 66, Lines 5-22:

" 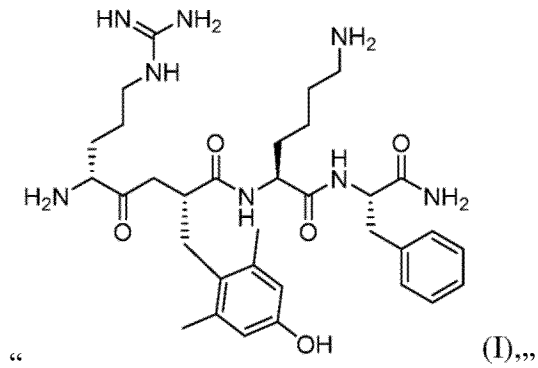 (I),"

Should read:

-- 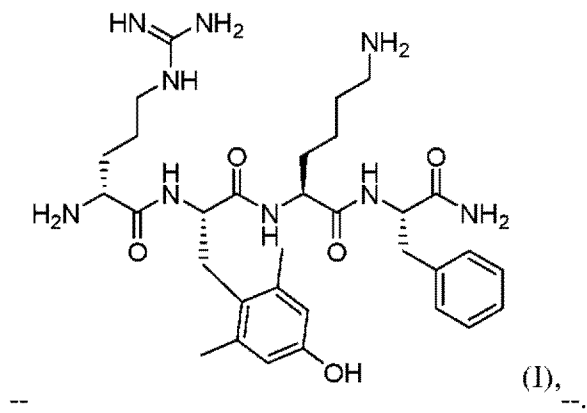 (I), --.